United States Patent [19]

Ikuina et al.

[11] Patent Number: 5,728,709
[45] Date of Patent: Mar. 17, 1998

[54] ALKYL AND ARALKYL-SUBSTITUTED PYRROLOCARBAZOLE DERIVATIVES THAT STIMULATE PLATELET PRODUCTION

[75] Inventors: Yoji Ikuina; Chikara Murakata, both of Shizuoka; Yutaka Saitoh, Machida; Yukimasa Shiotsu, Shizuoka; Takako Iida, Machida; Tatsuya Tamaoki, Shizuoka; Kinya Yamashita, Mishima; Shiro Akinaga, Shizuoka, all of Japan

[73] Assignee: Kyowa Hakko Kogyo Co., Ltd., Tokyo, Japan

[21] Appl. No.: 737,194

[22] PCT Filed: Mar. 7, 1996

[86] PCT No.: PCT/JP96/00557

§ 371 Date: Nov. 8, 1996

§ 102(e) Date: Nov. 8, 1996

[87] PCT Pub. No.: WO96/28447

PCT Pub. Date: Sep. 19, 1996

[30] Foreign Application Priority Data

Mar. 9, 1995 [JP] Japan ..................... 7-049441

[51] Int. Cl.⁶ ................. A61K 31/41; A61K 31/44; C07D 487/04
[52] U.S. Cl. ................. 514/279; 514/232.8; 514/338; 514/410; 544/142; 546/41; 546/276.7; 548/423
[58] Field of Search ..................... 514/279, 410, 514/232.8, 338; 548/423; 546/41, 276.7; 544/142

[56] References Cited

U.S. PATENT DOCUMENTS 4,912,107  3/1990  Kleinschroth et al. ........... 514/232.5
5,166,204  11/1992  Nagai et al. ..................... 514/232.8

FOREIGN PATENT DOCUMENTS 02142791  5/1990  Japan.
04178387  6/1992  Japan.
04230385  8/1992  Japan.

OTHER PUBLICATIONS

Bio. & Medicinal Chem. Letters, vol. 5, No. 11 (1995) 1167–69.

*Primary Examiner*—Johann Richter
*Assistant Examiner*—Laura L. Stockton
*Attorney, Agent, or Firm*—Fitzpatrick, Cella, Harper & Scinto

[57] ABSTRACT

Described herein is a pyrrolocarbazole derivative and a pharmaceutically acceptable salt thereof having the following formula (I):

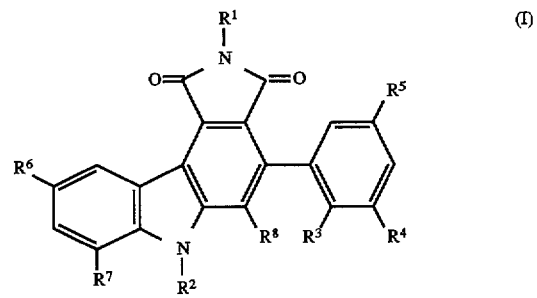

wherein $R^1$ is lower alkyl or aralkyl; $R^2$ is hydrogen, substituted or unsubstituted lower alkyl, lower alkenyl, or substituted or unsubstituted aralkyl; $R^3$, $R^4$, $R^5$, $R^6$ and $R^7$ may be the same or different, and are hydrogen, halogen, nitro, substituted or unsubstituted lower alkanoyl, $NR^9R^{10}$, or $OR^{11}$; $R^8$ is hydrogen or is combined with $R^3$ to form —$CONR^{12}$—; and when $R^1$ is benzyl; $R^2$, $R^3$, $R^4$, $R^5$, $R^6$, $R^7$ and $R^8$ are not simultaneously hydrogen. A compound of the present invention stimulates platelet production and is useful for treatment of thrombocytopenia.

13 Claims, No Drawings

ALKYL AND ARALKYL-SUBSTITUTED PYRROLOCARBAZOLE DERIVATIVES THAT STIMULATE PLATELET PRODUCTION This application is a 371 PCT/JP96/00557 filed Mar. 7, 1996.

1. Technical Field

The present invention relates to novel pyrrolocarbazole derivatives and pharmaceutically acceptable salts thereof useful as a therapeutic agent for thrombocytopenia.

2. Background Art

A decrease of platelets in number due to various hematopoietic disorders causes serious symptoms including a bleeding tendency. At present, platelet transfusion is considered to be effective against a decrease in platelets. However, a sufficient amount of platelets is not always supplied. Other than platelet transfusion, interleukin (IL) 6, IL-11, c-Mpl ligand and indolocarbazole derivatives are known to stimulate platelet production (Blood, 75, 1602 (1990); Blood, 81, 901 (1993); Nature, 369, 533 (1994); and WO94/06799).

Pyrrolocarbazole derivatives are known to have inhibiting activity against protein kinase C and antitumor activity (JP,2-142791,A and JP,4-178387,A).

However, it is unknown any type of pyrrolocarbazole derivatives stimulate platelet production.

DISCLOSURE OF THE INVENTION

The present invention relates to pyrrolocarbazole derivatives represented by Formula (I) and pharmaceutically acceptable salts thereof:

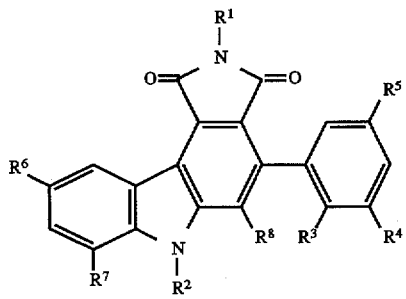

wherein $R^1$ is lower alkyl or aralkyl; $R^2$ is hydrogen, substituted or unsubstituted lower alkyl, lower alkenyl, or substituted or unsubstituted aralkyl; $R^3$, $R^4$, $R^5$, $R^6$ and $R^7$ may be the same or different, and are hydrogen, halogen, nitro, substituted or unsubstituted lower alkanoyl, $NR^9R^{10}$ {wherein $R^9$ and $R^{10}$ may be the same or different, and are hydrogen, substituted or unsubstituted lower alkyl, substituted or unsubstituted lower alkanoyl, aroyl, lower alkoxycarbonyl, aralkyloxycarbonyl or an amine acid residue in which a hydroxyl group in a carboxylic acid is removed (an amine group of the amine acid may be protected by a protective group)} or $OR^{11}$ (wherein $R^{11}$ is hydrogen, substituted or unsubstituted lower alkyl, substituted or unsubstituted lower alkanoyl, aroyl, or substituted or unsubstituted aralkyl, or heteroaralkyl); $R^8$ is hydrogen or is combined with $R^3$ to form —$CONR^{12}$— (wherein $R^{12}$ is hydrogen or substituted or unsubstituted lower alkyl); and when $R^1$ is benzyl, $R^2$, $R^3$, $R^4$, $R^5$, $R^6$, $R^7$ and $R^8$ are not simultaneously hydrogen.

Hereinafter, compounds represented by Formula (I) are referred to as Compound (I). The same shall apply to compounds represented by other formulae.

In the definitions of the groups in Compound (I), the lower alkyl means a straight-chain or branched alkyl group having 1 to 6 carbon atoms such as methyl, ethyl, propyl, isopropyl, butyl, iso-butyl, sec-butyl, tert-butyl, pentyl, neopentyl and hexyl. The substituted lower alkyl has 1 to 3 substituents, which may be the same or different, and, for example, are hydroxyl, halogen, lower alkanoyl, lower alkoxy, carboxy, lower alkoxycarbonyl, p-toluenesulfonyloxy, $NR^{13}R^{14}$ {wherein $R^{13}$ and $R^{14}$ may be the or different, and are hydrogen, lower alkyl, cycloalkyl, or aralkyloxycarbonyl, or $R^{13}$ and $R^{14}$ are combined together to form a heterocyclic group containing N therein (the heterocyclic group may contain an oxgen atom, a sulfur atom, or another nitrogen atom)}, $CONR^{15}R^{16}$ {wherein $R^{15}$ and $R^{16}$ may be the same or different, and are hydrogen or lower alkyl, or $R^{15}$ and $R^{16}$ are combined together to form a heterocyclic group having N therein (the heterocyclic group may contain an oxygen atom, sulfur atom or another nitrogen atom)}, $NR^{17}R^{18}R^{19}Hal$ {wherein $R^{17}$ and $R^{18}$ may be the same or different, and are hydrogen or lower alkyl, or $R^{17}$ and $R^{18}$ are combined together to form a heterocyclic group having N therein (the heterocyclic group may contain an oxygen atom, a sulfur atom, or another nitrogen atom); $R^{19}$ is lower alkyl; and Hal is a chlorine, bromine, or iodine atom}, trimethylsilylethoxy, or the like. The alkyl moiety of the lower alkyl, lower alkoxy, and lower alkoxycarbonyl has the same meaning as the lower alkyl defined above. The cycloalkyl means a group having 3 to 6 carbon atoms such as cyclopropyl, cyclobutyl, cyclopentyl and cyclohexyl. Examples of the M-containing heterocyclic group are pyrrolidinyl, morpholino, thiomorpholino, N-methylpiperazinyl, pyrazolidinyl, piperidino, piperazinyl, homopiperazinyl, indolyl and isoindolyl. The lower alkanoyl has the same meaning as the lower alkanoyl defined below, and the aralkyl moiety in the aralkyl oxycarbonyl has the same meaning as the aralkyl defined below.

The lower alkenyl means a group having 2 to 6 carbon atoms such as vinyl, allyl, butenyl, pentenyl, hexenyl, pentadienyl and hexadienyl.

The aralkyl and the aralkyl moiety in aralkyloxycarbonyl mean a group having 7 to 15 carbon atoms such as benzyl, phenethyl, benzhydryl and naphthylmethyl. The substituted lower aralkyl has 1 to 3 substituents, which may be the same or different, and are, for example, halogen, nitro, amino, lower alkylamino, or di-lower-alkylamino. The lower alkyl in the lower alkylamino and the di-lower-alkylamino have the same meaning as the lower alkyl defined above.

The heteroaralkyl means a group having 5 to 14 carbon atoms such as picolyl and quinaldyl.

The lower alkanoyl means a straight-chain or branched alkanoyl group having 1 to 6 carbon atoms such as formyl, acetyl, propionyl, butyryl, isobutyryl, valeryl, isovaleryl, pivaloyl and hexanoyl. The substituted lower alkanoyl has 1 to 3 substituents, which may be the same or different, and are, for example, halogen or $NR^{20}R^{21}$ (wherein $R^{20}$ and $R^{21}$ have the same meanings as $R^{13}$ and $R^{14}$ defined above).

The aroyl means a group having 7 to 15 carbon atoms such as benzoyl and naphthoyl.

The lower alkyl moiety in the lower alkoxycarbonyl has the same meaning as the lower alkyl defined above.

The halogen and the halogen moiety in a substituent of the above-mentioned lower alkyl or lower alkanoyl may be the same or different, and are fluorine, chlorine, bromine, or iodine.

The amino acid means glycine, alanine, proline, glutamic acid, lysine, serine, cysteine, phenylalanine, tyrosine, or the like. The amino protective group for the amino acid means those which are generally used for peptide syntheses, for example, benzyloxycarbonyl and t-butoxycarbonyl.

The substituted or unsubstituted lower alkyl in $R^{12}$ has the same meaning as the above-mentioned substituted or unsubstituted lower alkyl.

The pharmaceutically acceptable salts of Compounds (I) include pharmaceutically acceptable acid addition salts, metal salts, ammonium salts, organic amine addition salts and amino acid addition salts. The acid addition salts include inorganic salts such as hydrochloride, sulfate and phosphate, and organic salts, such as acetate, maleate, fumarate, tartrate, citrate, lactate, aspartate and glutamate. The metal salts include alkali metal salts such as sodium salt and potassium salt, alkaline earth metal salts such as magnesium salt and calcium salt, aluminum salt and zinc salt. The ammonium salts include ammonium salt and tetramethyl ammonium salt. The organic amine addition salts include salts with morpholine and piperidine. The amino acid addition salts include salts with lysine, glycine, and phenylalanine.

The process for producing Compound (I) is explained below.

In the following reaction steps, structural formulae, tables, and the like, the symbols Me, Et, n-Pr, i-Pr, n-Bu, allyl, Bn, Ac, Bz, Boc, Z, and Ts stand for methyl, ethyl, n-propyl, isopropyl, n-butyl, allyl, benzyl, acetyl, benzoyl, t-butoxycarbonyl, benzyloxycarbonyl, and p-toluenesulfonyl, respectively. In addition, each of the groups in each of the steps has the same meaning as defined above, unless otherwise specified.

Compound (I) can be prepared according to the following reaction steps.

In the following process, when a defined group changes under reaction conditions or is not suitable for carrying out the process, the desired compound can be obtained by using protection/deprotection method for functional groups generally employed in organic synthetic chemistry (see, for example, Protective Groups in Organic Synthesis, T. W. Greene, John Wiley & Sons Inc. (1981)). In addition, the order of reaction steps, for example, the introduction of a substituent, may be changed, if necessary.

Process 1

Compound (Ia), which is Compound (I) in which $R^2$ and $R^8$ are hydrogen, can be obtained by the following step.

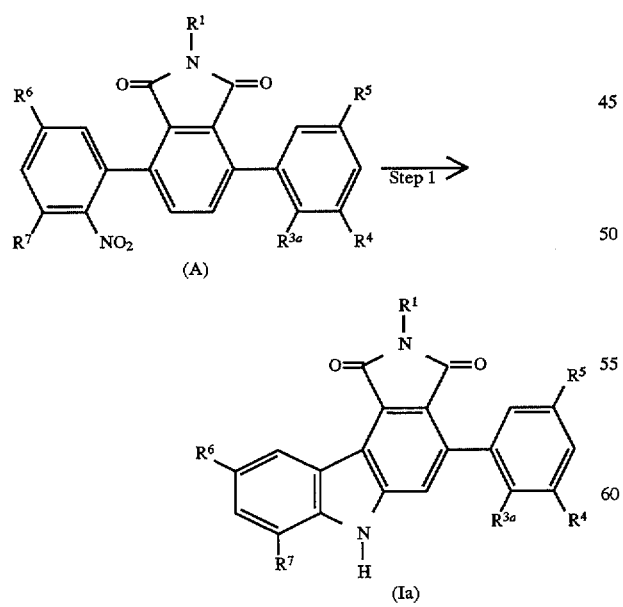

In the formulae, $R^1$, $R^4$, $R^5$, $R^6$ and $R^7$ are the same meanings as defined above; and $R^{3a}$ has the same meaning as $R^3$ defined above, except that —$NR^{12}CO$— (wherein $R^{12}$ is the same meaning as defined above), which is formed together with $R^8$, is not included in the definition.

Step 1

Compound (Ia) can be obtained by reacting Compound (A), which is prepared according to conventional methods (e.g., Tetrahedron Lett., 24, 1441, (1983); and J. Chem. Sec. Perkin Trans I, 2475 (1990)), with a trivalent phosphorus compound such as triphenylphosphine, in a solvent such as collidine.

The trivalent phosphorus compound is used in an amount of 1 to 4 equivalents based on Compound (A). The reaction is carried out at 100° to 200° C. for 3 to 48 hours.

Process 2

Compound (Ib), which is Compound (I) in which $R^8$ is hydrogen, can be obtained by the following steps.

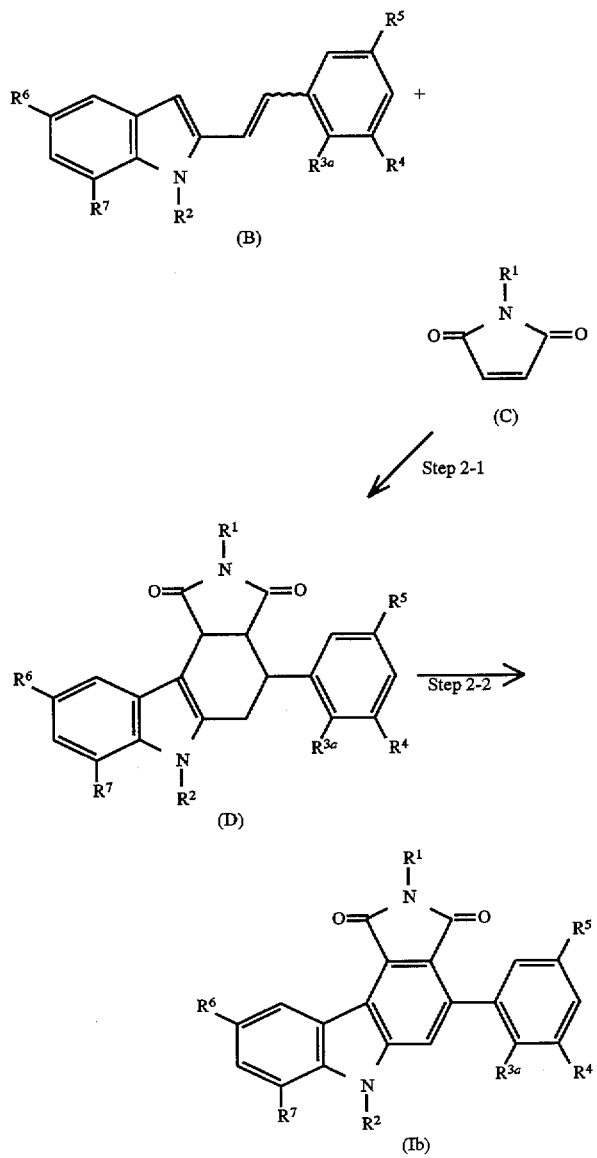

In the formulae, $R^1$, $R^2$, $R^4$, $R^5$, $R^6$, $R^7$ and $R^{3a}$ are the same meanings as defined above.

Step 2-1

Compound (D) can be obtained by reacting Compound (B), which will be described later, with Compound (C) in a solvent such as toluene and dichlorobenzene, or without solvent.

Compound (C) is used in an amount of 1 to 10 equivalents based on Compound (B). The reaction is carried out at 100° to 200° C. for 1 minute to 24 hours.

Compound (B) can be obtained by a Wittig reaction of substituted or unsubstituted benzaldehyde with a substituted or unsubstituted halogenated indole-2-methyltriphenylphosphonium salt (the halogen has the same meaning as Hal defined above), which is prepared according to known methods (e.g., Can. J. Chem., 51, 792 (1973)), or by the Wittig reaction (e.g., Can. J. chem., 51, 792 (1973); and Synthesis, 743 (1992)) of a substituted or unsubstituted indole-2-carboxyaldehyde, which is obtained according to known methods (e.g., J. Org. Chem., 52, 104 (1987)), with a substituted or unsubstituted halogenated benzyltriphenylphosphonium salt (the halogen has the same meaning as Hal defined above).

Step 2-2

Compound (Ib) can be obtained by reacting Compound (D) with a dehydrogenating agent such as 2,3-dichloro-5,6-dicyano-1,4-benzoquinone (DDQ) and 10% Pd/C, in a solvent such as methylene chloride, ethyl acetate (AcOEt), toluene and dioxane.

The dehydrogenating agent is used in an amount of 2 to 10 equivalents based on Compound (D). The reaction is carried out at 0° to 180° C. for 1 minute to 24 hours.

Process 3

Compound (Id), which is Compound (I) in which $R^2$ is a functional group, can be also obtained from Compound (Ic) in which $R^2$ is hydrogen, by the following step.

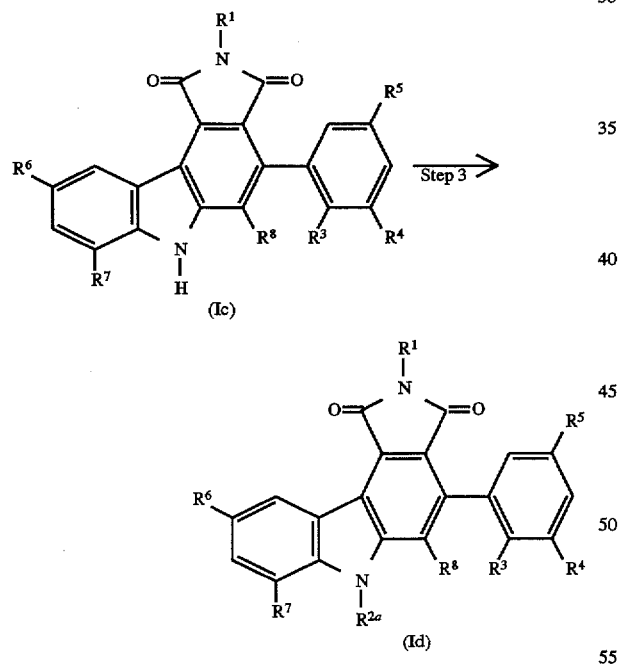

In the formulae $R^1$, $R^3$, $R^4$, $R^5$, $R^6$, $R^7$ and $R^8$ are the same meanings as defined above; and $R^{2a}$ is the same meaning as $R^2$, except that hydrogen is not included in the definition.

Step 3

In a solvent such as N,N-dimethylformamide (DMF), tetrahydrofuran (THF), toluene and a mixture thereof, and in the presence of a base such as sodium hydride and potassium t-butoxide, Compound (Id) can be obtained by reacting Compound (Ic) with Compound (II) of the following formula:

$$R^{2a}Hal \qquad (II)$$

wherein $R^{2a}$ and Hal are the same meanings as defined above.

Compound (II) and the base are each used in an amount of 1 to 10 equivalents based on Compound (Ic). The reaction is carried out at –20° to 120° C. for 1 to 24 hours.

Process 4

Compound (If) or Compound (Ig), each of which is Compound (I) in which $R^3$ and $R^8$ together form —$NR^{12}CO$—, can be obtained by the following steps.

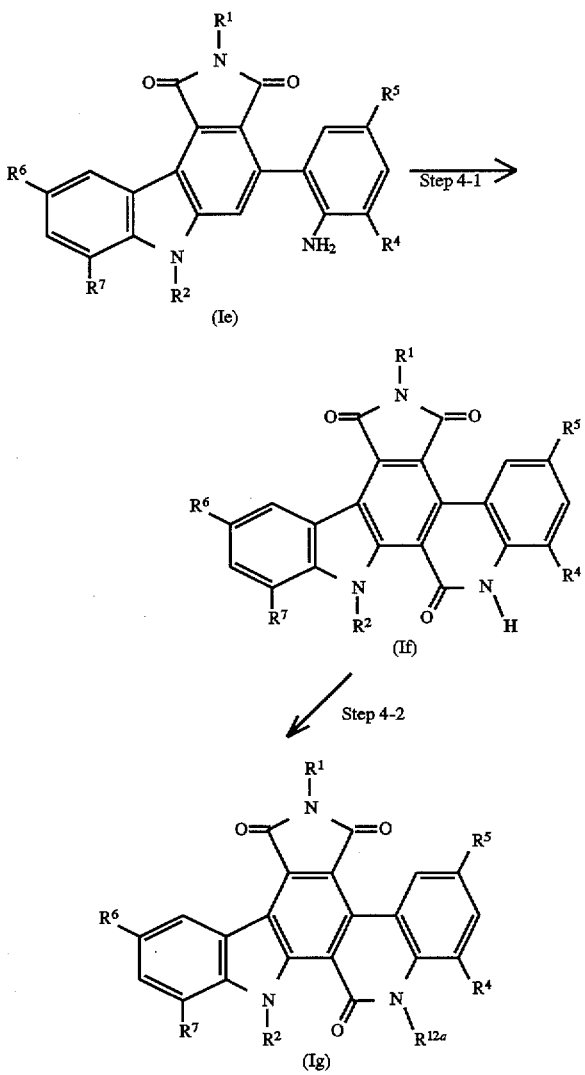

In the formulae, $R^1$, $R^2$, $R^4$, $R^5$, $R^6$ and $R^7$ are the same meanings as defined above; and $R^{12a}$ is the same meaning as $R^{12}$ defined above, except that a hydrogen group is not included in the definition.

Step 4-1

Compound (If) can be prepared by reacting Compound (Ie) with a phosgene compound such as phosgene and triphosgene, followed by a treatment with a Lewis acid in a solvent such as dichlorobenzene, 1,2-dichloroethane and a mixture thereof, in the presence or absence of a base such as triethylamine.

The base and the phosgene compound are used in an amount of 0 to 10 equivalents and 1 to 5 equivalents, respectively, based on Compound (Ie). Aluminum chloride is preferably used as the Lewis acid in an amount of 1 to 10 equivalents based on Compound (Ie). The reaction is carried out at 0° to 180° C. for 1 to 24 hours.

Step 4-2

In a solvent such as DMF, in the presence of a base such as sodium hydride, Compound (Ig) can be obtained by reacting Compound (If) with Compound (III) of the following formula:

$R^{12a}Hal$ (III)

wherein $R^{12a}$ and Hal are the same meanings as defined above. Compound (III) and the base are each used in an amount of 1 to 6 equivalents based on Compound (If). The reaction is carried out at −20° to 120° C. for 1 to 24 hours.

Process 5

Compound (Ii), which is Compound (I) in which $R^2$ is a functional group, can be also obtained from Compound (Ih), which is Compound (I) in which $R^2$ is another functional group, by the following steps.

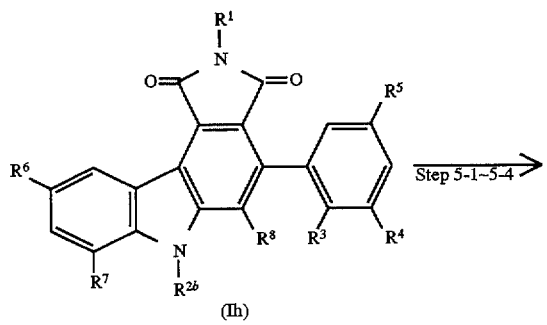

(Ih)

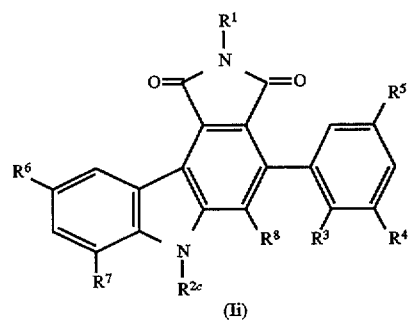

(Ii)

In the formulae, $R^1$, $R^3$, $R^4$, $R^5$, $R^6$, $R^7$ and $R^8$ are the same meanings as defined above; and $R^{2b}$ and $R^{2c}$ are defined in each of the following steps.

Step 5-1

In the formulae, $R^{2b}$ is nitro-substituted aralkyl and $R^{2c}$ is amine-substituted aralkyl.

Compound (Ii) can be obtained by catalytic hydrogenation of Compound (Ih) in a solvent, such as AcOEt, DMF and a mixture thereof in the presence of a catalyst such as 10% Pd/C.

Based on Compound (Ih), 10 to 100% (by weight) of the reduction catalyst is used. The reaction is carried out at 0° to 60° C. for 1 to 24 hours.

Step 5-2

In the formulae, $R^{2b}$ is amino- or mono-lower-alkylamino-substituted aralkyl, or amino- or mono-lower-alkylamino-substituted lower alkyl; and $R^{2c}$ is mono- or di-lower alkylamino-substituted aralkyl, or mono- or di-lower alkylamino-substituted lower alkyl.

Compound (Ii) can be obtained by reductive alkylation of the primary or secondary amine group of Compound (Ih) by using aldehyde in a solvent such as methanol, acetonitrile, water and a mixture thereof in the presence of a reducing agent such as sodium cyanoborohydride and sodium triacetoxyborohydrido.

The reducing agent and aldehyde are each used in an amount of 1 to 200 equivalents based on Compound (Ih). The reaction is carried out at −10° to 50° C. for 5 minutes to 24 hours.

Step 5-3

In the formulae, $R^{2b}$ is halogen-substituted lower alkyl (the halogen has the same meaning as Hal defined above); and $R^{2c}$ is $NR^{13a}R^{14a}$-substituted lower alkyl (wherein $R^{13a}$ and $R^{14a}$ are the same meanings as $R^{13}$ and $R^{14}$ defined above, except that an aralkyloxycarbonyl group is not included in the definition).

In a solvent such as DMF, Compound (Ii) can be obtained by reacting Compound (Ih) with Compound (IV) having the following formula:

$HNR^{13a}R^{14a}$ (IV)

wherein, $R^{13a}$ and $R^{14a}$ are the same meanings as defined above.

Compound (IV) is used in an amount of 1 to 200 equivalents based on Compound (Ih). The reaction is carried out at 0° to 120° C. for 1 to 24 hours.

Step 5-4

In the formulae, $R^{2b}$ is trimethylsilylethoxymethyl and $R^{2c}$ is hydrogen.

Compound (Ii) can be obtained by reacting Compound (Ih) with an acid such as hydrochloric acid and sulfuric acid in a solvent such as THF.

The acid is used in an amount of 0.1 to 200 equivalents based on Compound (Ih). The reaction is carried out at 0° to 120° C. for 1 to 24 hours.

Process 6

Compound (Ik), which is Compound (I) in which $R^3$, $R^4$, $R^5$, $R^6$ or $R^7$ is a functional group, can be also obtained from Compound (Ij), which is Compound (I) in which $R^3$, $R^4$, $R^5$, $R^6$ or $R^7$ is another functional group, by the following steps.

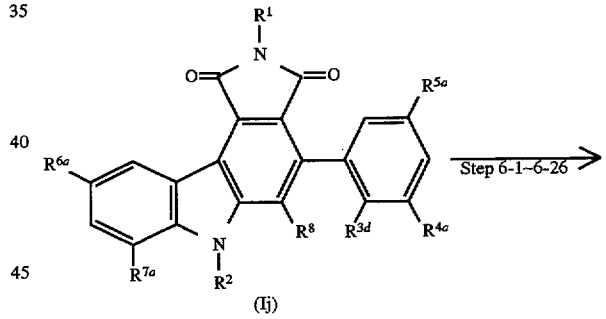

(Ij)

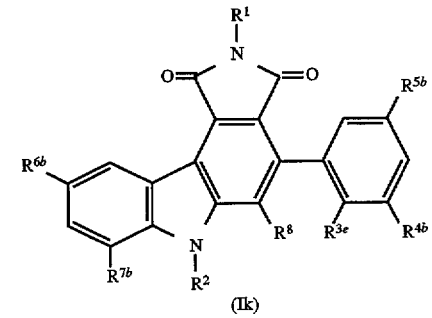

(Ik)

In the formulae, $R^1$, $R^2$ and $R^8$ are the same meanings as defined above; and $R^{3d}$, $R^{4a}$, $R^{5a}$, $R^{6a}$, $R^{7a}$, $R^{3e}$, $R^{4b}$, $R^{5b}$, $R^{6b}$ and $R^{7b}$ are defined in each of the following steps.

Step 6-1

In the formulae, at least one of $R^{3d}$, $R^{4a}$, $R^{5a}$, $R^{6a}$ and $R^{7a}$ is hydrogen; and at least one of $R^{3e}$, $R^{4b}$, $R^{5b}$, $R^{6b}$ and $R^{7b}$ is nitro.

Compound (Ik) can be obtained by reacting Compound (Ij) with nitric acid in a solvent such as methylene chloride, chloroform and 1,2-dichloroethane in the presence or absence of an acid such as trifluoromethanesulfonic acid, sulfuric acid and acetic acid.

The acid and nitric acid are each used in an amount of 1 to 100 equivalents based on Compound (Ij). The reaction is carried out at −78° to 50° C. for 5 minutes to 24 hours.

Step 6-2

In the formulae, at least one of $R^{3d}$, $R^{4a}$, $R^{5a}$, $R^{6a}$ and $R^{7a}$ is nitro; and at least one of $R^{3e}$, $R^{4b}$, $R^{5b}$, $R^{6b}$ and $R^{7b}$ is amino.

Compound (Ik) can be obtained by catalytic hydrogenation of Compound (Ij) in a solvent such as DMF, AcOEt and a mixture thereof in the presence of a catalyst such as 10% Pd/C.

Based on Compound (Ij), 10 to 100% (by weight) of the reduction catalyst is used. The reaction is carried out at 0° to 90° C. for 1 to 24 hours.

Step 6-3

In the formulae, at least one of $R^{3d}$, $R^{4a}$, $R^{5a}$, $R^{6a}$ and $R^{7a}$ is hydrogen; and at least one of $R^{3e}$, $R^{4b}$, $R^{5b}$, $R^{6b}$ and $R^{7b}$ is halogen (the halogen has the same meaning as Hal defined above).

Compound (Ik) can be obtained by reacting Compound (Ij) with a halogenating agent such as sulfuryl chloride, tetra-n-butylammonium tribromide, N-bromosuccinimide and N-iodosuccinimide in a solvent such as chloroform, methylene chloride, methanol, THF and a mixture thereof in the presence or absence of a base such as t-butylamine.

The base and the halogenating agent are used in an amount of 0 to 5 equivalents and 1 to 5 equivalents, respectively, based on Compound (Ij). The reaction is carried out at −20° to 100° C. for 5 minutes to 24 hours.

Step 6-4

In the formulae, at least one of $R^{3d}$, $R^{4a}$, $R^{5a}$, $R^{6a}$ and $R^{7a}$ is hydrogen; and at least one of $R^{3e}$, $R^{4b}$, $R^{5b}$, $R^{6b}$ and $R^{7b}$ is substituted or unsubstituted lower alkanoyl.

Compound (Ik) can be obtained by reacting Compound (Ij) with substituted or unsubstituted halogenated lower alkanoyl (the halogen has the same meaning as Hal defined above) or dichloromethyl methyl ether in a solvent such as methylene chloride, chloroform and 1,2-dichloroethane in the presence of a Lewis acid.

As the Lewis acid, aluminum chloride, titanium tetrachloride, or the like is used. The Lewis acid, substituted or unsubstituted halogenated lower alkanoyl and dichloromethyl methyl ether are each used in an amount of 1 to 20 equivalents based on Compound (Ij). The reaction is carried out at −78° to 80° C. for 5 minutes to 24 hours.

Step 6-5

In the formulae, at least one of $R^{3d}$, $R^{4a}$, $R^{5a}$, $R^{6a}$ and $R^{7a}$ is substituted or unsubstituted lower alkanoyl; and at least one of $R^{3e}$, $R^{4b}$, $R^{5b}$, $R^{6b}$ and $R^{7b}$ is $OR^{11a}$ (wherein $R^{11a}$ is substituted or unsubstituted lower alkanoyl).

Compound (Ik) can be obtained by reacting Compound (Ij) with a peroxide in a solvent such as methylene chloride, chloroform and 1,2-dichloroethane in the presence of a base.

As the peroxide, m-chloroperbenzoic acid, peracetic acid, hydrogen peroxide, t-butyl hydroperoxide, or the like is used. As the base, sodium hydrogencarbonate, sodium carbonate, potassium hydrogencarbonate, potassium carbonate, sodium acetate, or the like is used. The peroxide and the base are each used in an amount of 1 to 20 equivalents based on Compound (Ij). The reaction is carried out at −10° to 50° C. for 1 to 24 hours.

Step 6-6

In the formulae, at least one of $R^{3d}$, $R^{4a}$, $R^{5a}$, $R^{6a}$ and $R^{7a}$ is $OR^{11a}$ (wherein $R^{11a}$ is the same meaning as defined above), and at least one of $R^{3e}$, $R^{4b}$, $R^{5b}$, $R^{6b}$ and $R^{7b}$ is hydroxy.

Compound (Ik) can be obtained by reacting Compound (Ij) with an acid or a base in a solvent such as THF, methanol, dioxane, water and a mixture thereof.

As the acid, hydrochloric acid, sulfuric acid, or the like is used. As the base, sodium methoxide, sodium hydrogencarbonate, potassium carbonate, aqueous ammonium, dimethylamine, or the like is used. The acid or the base is used in an amount of 0.1 to 100 equivalents based on Compound (Ij). The reaction is carried out at −10° to 120° C. for 5 minutes to 24 hours.

Step 6-7

In the formulae, at least one of $R^{3d}$, $R^{4a}$, $R^{5a}$, $R^{6a}$ and $R^{7a}$ is NHZ (wherein Z is the same meaning as defined above) or hydroxy; and at least one of $R^{3e}$, $R^{4b}$, $R^{5b}$, $R^{6b}$ and $R^{7b}$ is $NZR^{9a}$ (wherein Z is the same meaning as defined above and $R^{9a}$ is substituted or unsubstituted lower alkyl) or $OR^{11b}$ (wherein $R^{11b}$ is substituted or unsubstituted lower alkyl, substituted or unsubstituted lower aralkyl, or heteroaralkyl).

In the presence of a base, in a solvent which is inert to the reaction, Compound (Ik) can be obtained by reacting Compound (Ij) with one of Compound (V), Compound (VI) and Compound (VII), respectively having the following formulae:

$R^{9a}Hal$          (V);

$R^{11b}Hal$          (VI);

and

$R^{11b}OTs$          (VII);

wherein $R^{9a}$, $R^{11b}$, Hal and Ts are the same meanings as defined above.

As the reaction solvent, DMF, THF, toluene, or a mixture thereof is used. As the base, sodium hydride, potassium carbonate, or the like is used. The base and one of Compound (V), Compound (VI) and Compound (VII) are each used in an amount of 1 to 10 equivalents based on Compound (Ij). The reaction is carried out at −20° to 120° C. for 5 minutes to 24 hours.

Step 6-8

In the formulae, at least one of $R^{3d}$, $R^{4a}$, $R^{5a}$, $R^{6a}$ and $R^{7a}$ is $NR^{9b}R^{10a}$ (wherein at least one of $R^{9b}$ and $R^{10a}$ is hydrogen or amino-substituted lower alkyl) or $OR^{11c}$ (wherein $R^{11c}$ is mono-lower-alkylamino-substituted lower alkyl); and at least one of $R^{3e}$, $R^{4b}$, $R^{5b}$, $R^{6b}$ and $R^{7b}$ is $NR^{9c}R^{10b}$ (wherein at least one of $R^{9c}$ and $R^{10b}$ is none- or di-lower-alkylamino-substituted lower alkyl) or $OR^{11d}$ (wherein $R^{11d}$ is di-lower-alkylamino-substituted lower alkyl).

Compound (Ik) can be obtained by reductive alkylation of the primary or secondary amine group of Compound (Ij) by using aldehyde in a solvent such as methanol, acetonitrile, water and a mixture thereof in the presence of a reducing agent such as sodium cyanoborohydride and sodium triacetoxyborohydride.

The reducing agent and aldehyde are each used in an amount of 1 to 200 equivalents based on Compound (Ij). The reaction is carried out at −10° to 50° C. for 5 minutes to 24 hours.

Step 6-9

In the formulae, at least one of $R^{3d}$, $R^{4a}$, $R^{5a}$, $R^{6a}$ and $R^{7a}$ is $OR^{11e}$ (wherein $R^{11e}$ is halogen-substituted or p-toluenesulfonyloxy-substituted lower alkyl) or $NR^{9d}R^{10c}$ (wherein at least one of $R^{9d}$ and $R^{10c}$ is halogen-substituted lower alkyl or halogen-substituted lower alkanoyl); and at least one of $R^{3e}$, $R^{4b}$, $R^{5b}$, $R^{6b}$ and $R^{7b}$ is $OR^{11f}$ {wherein $R^{11f}$ is $NR^{13a}R^{14a}$-substituted lower alkyl (wherein $R^{13a}$ and $R^{14a}$ are the same meanings as defined above)} or $NR^{9e}R^{10d}$ {wherein at least one of $R^{9e}$ and $R^{10d}$ is $NR^{13a}R^{14a}$-substituted lower alkyl (wherein $R^{13a}$ and $R^{14a}$ are the same meanings as defined above) or $NR^{20a}R^{21a}$-substituted lower alkanoyl (wherein $R^{20a}$ and $R^{21a}$ are the same meaning as $R^{13a}$ and $R^{14a}$ defined above)}.

In the presence or absence of sodium iodide or potassium iodide, in a solvent such as DMF and methylene chloride, Compound (Ik) can be obtained by reacting Compound (Ij) with Compound (IV) mentioned above or with Compound (VIII) having the following formula:

wherein $R^{20a}$ and $R^{21a}$ are the same meanings as defined above.

Based on Compound (Ij), sodium iodide or potassium iodide is used in an amount of 0 to 200 equivalents, and Compound (IV) or Compound (VIII) is used in an amount of 1 to 200 equivalents. The reaction is carried out at 0° to 120° C. for 1 to 24 hours.

Step 6-10

In the formulae, at least one of $R^{3d}$, $R^{4a}$, $R^{5a}$, $R^{6a}$ and $R^{7a}$ is amino; and at least one of $R^{3e}$, $R^{4b}$, $R^{5b}$, $R^{6b}$ and $R^{7b}$ is aralkyloxycarbonylamino or lower alkoxycarbonylamino.

Compound (Ik) can be obtained by reacting Compound (Ij) with an aralkyloxycarboyl halide such as benzyloxycarbonyl chloride, or with a halogenated lower alkoxycarbonyl (the halogen has the same meaning as Hal defined above) such as chloromethyl formate, in a solvent such as THF, dioxane, acetonitrile, water and a mixture thereof, in the presence or absence of a base such as sodium hydrogencarbonate and pyridine.

Based on Compound (Ij), the aralkyloxycarboyl halide or the halogenated lower alkoxycarbonyl is used in an amount of 1 to 10 equivalents, and the base is used in an amount of 0 to 10 equivalents. The reaction is carried out at −10° to 50° C. for 5 minutes to 24 hours.

Step 6-11

In the formulae, at least one of $R^{3d}$, $R^{4a}$, $R^{5a}$, $R^{6a}$ and $R^{7a}$ is $NZR^{9a}$ (wherein Z and $R^{9a}$ are the same meanings as defined above) or $OR^{11g}$ (wherein $R^{11g}$ is substituted or unsubstituted lower aralkyl); and at least one of $R^{3e}$, $R^{4b}$, $R^{5b}$, $R^{6b}$ and $R^{7b}$ is $NHR^{9a}$ (wherein $R^{9a}$ is the same meaning as defined above) or hydroxy.

Compound (Ik) can be obtained by catalytic hydrogenation of Compound (Ij) in a solvent such as AcOEt, DMF and a mixture thereof in the presence of a catalyst such as 10% Pd/C.

Based on Compound (Ij), 10 to 100% (by weight) of the reduction catalyst is used. The reaction is carried out at 0° to 120° C. for 1 to 24 hours.

Step 6-12

In the formulae, at least one of $R^{3d}$, $R^{4a}$, $R^{5a}$, $R^{6a}$ and $R^{7a}$ is $NHR^{9f}$ (wherein $R^{9f}$ is hydrogen or substituted or unsubstituted lower alkyl) or hydroxy; and at least one of $R^{3e}$, $R^{4b}$, $R^{5b}$, $R^{6b}$ and $R^{7b}$ is $NR^{9f}R^{10e}$ (wherein $R^{9f}$ as the same meaning as defined above and $R^{10e}$ is substituted or unsubstituted lower alkanoyl or aroyl) or $OR^{11h}$ (wherein $R^{11h}$ is substituted or unsubstituted lower alkanoyl or aroyl).

In the presence or absence of 4-dimethylaminopyridine (DMAP), in the presence of a base such as pyridine and triethylamine, in a solvent such as THF, DMF, methylene chloride and a mixture thereof, Compound (Ik) can be obtained by reacting. Compound (Ij) with one of Compound (IX), Compound (X), Compound (XI) and Compound (XII), respectively having the following formulae:

and

wherein $R^{10e}$, $R^{11b}$ and Hal are as defined above.

The base and one of Compound (IX), Compound (X), Compound (XI) and Compound (XII) are each used in an amount of 1 to 50 equivalents, and DMAP is used in an amount of 0.001 to 1 equivalent, based on Compound (Ij). The reaction is carried out at −20° to 120° C. for 5 minutes to 24 hours.

Step 6-13

In the formulae, at least one of $R^{3d}$, $R^{4a}$, $R^{5a}$, $R^{6a}$ and $R^{7a}$ is amino; and at least one of $R^{3e}$, $R^{4b}$, $R^{5b}$, $R^{6b}$ and $R^{7b}$ is $NHR^{9g}$ (wherein $R^{9g}$ is an amino acid residue in which a hydroxyl group in a carboxylic acid is removed).

Compound (Ik) can be obtained by reacting Compound (Ij) with an N-protective amine acid in a solvent such as THF, DMF, methylene chloride and a mixture thereof in the presence of a condensing agent such as N,N'-dicyclohexylcarbodiimide or diphenylphosphorylazide/triethylamine.

The condensing agent and the N-protective amine acid are each used in an amount of 1 to 6 equivalents based on Compound (Ij). The reaction is carried out at −20° to 50° C. for 1 to 24 hours. A Boc group, Z group, or the like is used as the N-protecting group for amino acid. If necessary, the N-protecting group is cleaved by a conventional method (e.g., a catalytic hydrogenation or an acid treatment) after the reaction is completed.

Step 6-14

In the formulae, at least one of $R^{3d}$, $R^{4a}$, $R^{5a}$, $R^{6a}$ and $R^{7a}$ is amino; and at least one of $R^{3e}$, $R^{4b}$, $R^{5b}$, $R^{6b}$ and $R^{7b}$ is hydroxy.

Compound (Ik) can be obtained by reacting Compound (Ij) with sodium nitrite in an acidic solvent such as sulfuric acid and hydrochloric acid, followed by heating.

Sodium nitrite is used in an amount of 1 to 6 equivalents based on Compound (Ij). The reaction is carried out at −10° to 100° C. for 1 to 5 hours.

Step 6-15

In the formulae, at least one of $R^{3d}$, $R^{4a}$, $R^{5a}$, $R^{6a}$ and $R^{7a}$ is hydroxy, and at least one of $R^{3e}$, $R^{4b}$, $R^{5b}$, $R^{6b}$ and $R^{7b}$ is $OR^{11i}$ (wherein $R^{11i}$ is hydroxy-substituted lower alkyl).

Compound (Ik) can be obtained by reacting Compound (Ij) with an alkylene carbonate such as ethylene carbonate in a solvent such as DMF in the presence of a base including lithium hydride, or a halogenated tetra-lower-alkylammonium including brominated tetra-n-butylammonium and iodinated tetra-ethylammonium.

Based on Compound (Ij), the base or the halogenated tetra-lower-alkylammonium are used in an amount of 0.1 to 10 equivalents, and the alkylene carbonate is used in an amount of 1 to 10 equivalents. The reaction is carried out at 50° to 180° C. for 30 minutes to 24 hours.

Step 6-16

In the formulae, at least one of $R^{3d}$, $R^{4a}$, $R^{5a}$, $R^{6a}$ and $R^{7a}$ is $OR^{11i}$ (wherein $R^{11i}$ is the same meaning as defined above); and at least one of $R^{3e}$, $R^{4b}$, $R^{5b}$, $R^{6b}$ and $R^{7b}$ is $OR^{11j}$ (wherein $R^{11j}$ is lower-alkoxy-substituted lower alkyl).

In the presence of a base such as sodium hydride, in a solvent such as DMF, Compound (Ik) can be obtained by reacting Compound (Ij) with Compound (XIII) having the following formula:

wherein $R^{22}$ is lower alkyl and Hal is the same meaning as defined above.

The base and Compound (XIII) are each used in an amount of 1 to 10 equivalents based on Compound (Ij). The reaction is carried out at −20° to 80° C. for 5 minutes to 24 hours.

Step 6-17

In the formulae, at least one of $R^{3d}$, $R^{4a}$, $R^{5a}$, $R^{6a}$ and $R^{7a}$ is $OR^{11k}$ (wherein $R^{11k}$ is lower-alkoxycarbonyl-substituted lower alkyl); and at least one of $R^{3e}$, $R^{4b}$, $R^{5b}$, $R^{6b}$ and $R^{7b}$ is $OR^{11m}$ (wherein $R^{11m}$ is carboxy-substituted lower alkyl).

Compound (Ik) can be obtained by reacting Compound (Ij) with an acid such as hydrochloric acid and sulfuric acid in a solvent, such as methylene chloride, dioxane, THF and a mixture thereof.

The acid is used in an amount of 0.1 to 100 equivalents based on Compound (Ij). The reaction is carried out at 0° to 120° C. for 1 to 24 hours.

Step 6-18

In the formulae, at least one of $R^{3d}$, $R^{4a}$, $R^{5a}$, $R^{6a}$ and $R^{7a}$ is $OR^{11m}$ (wherein $R^{11m}$ is the same meaning as defined above); and at least one of $R^{3e}$, $R^{4b}$, $R^{5b}$, $R^{6b}$ and $R^{7b}$ is $OR^{11n}$ {wherein $R^{11n}$ is $CONR^{15}R^{16}$-substituted lower alkyl (wherein $R^{15}$ and $R^{16}$ are as defined above)}.

Compound (Ik) can be obtained by reacting Compound (Ij) with a halogenating agent such as thionyl chloride, phosphoryl chloride, phosphorus pentachloride and phosphorus trichloride in a solvent such as methylene chloride, THF and a mixture thereof, or without solvent, followed by a reaction with Compound (XIV) having the following formula:

wherein $R^{15}$ and $R^{16}$ are the same meanings as defined above.

The halogenating agent and Compound (XIV) are each used in an amount of 1 to 100 equivalents based on Compound (Ij). The reaction is carried out at −20° to 120° C. for 30 minutes to 24 hours.

Step 6-19

In the formulae, at least one of $R^{3d}$, $R^{4a}$, $R^{5a}$, $R^{6a}$ and $R^{7a}$ is $OR^{11o}$ {wherein $R^{11o}$ is $CONR^{15a}R^{16a}$-substituted lower alkyl (wherein $R^{15a}$ and $R^{16a}$ are the same meanings as $R^{15}$ and $R^{16}$ defined above, except that hydrogen is not included in the definition)}; and at least one of $R^{3e}$, $R^{4b}$, $R^{5b}$, $R^{6b}$ and is $R^{7b}$ is $OR^{11p}$ {wherein $R^{11p}$ is $NR^{13b}R^{14b}$-substituted lower alkyl {wherein $R^{13b}$ and $R^{14b}$ are the same meanings as the above-mentioned $R^{15a}$ and $R^{16a}$)}.

Compound (Ik) can be obtained by reacting Compound (Ij) with trimethyloxoniumtetrafluoroborate in a solvent such as methylene chloride, methanol and a mixture thereof, followed by a treatment with a reducing agent such as sodium cyanoborohydride and sodium triacetoxyborohydride.

Trimethyloxoniumtetrafluoroborate and the reducing agent are each used in an amount of 1 to 20 equivalents based on Compound (Ij). The reaction is carried out at −20° to 120° C. for 30 minutes to 48 hours.

Step 6-20

In the formulae, $R^{4a}$, and $R^{4b}$ are the same meanings as $R^4$ defined above; $R^{6a}$ and $R^{6b}$ are the same meanings as $R^6$ defined above; $R^{7a}$ and $R^{7b}$ are the same meanings as $R^7$ defined above; $R^{3d}$ and $R^{3e}$ are hydroxy; $R^{5a}$ is hydrogen; and $R^{5b}$ is hydroxy.

Compound (Ik) can be obtained by reacting Compound (Ij) with oxidizing agent such as [bis(trifluoroacetoxy)iodo] benzene and potassium nitrosodisulfonate in a mixed solvent of, for example, DMF and acetonitrile, said solvent containing water or a buffer solution (e.g., a phosphate buffer), followed by a treatment with a reducing agent such as sodium hydrosulfite and sodium nitrite.

The oxidizing agent and the reducing agent are each used in an amount of 1 to 20 equivalents. The reaction is carried out at −20° to 60° C. for 5 minutes to 24 hours.

Step 6-21

In the formulae, at least one of $R^{3d}$, $R^{4a}$, $R^{5a}$, $R^{6a}$ and $R^{7a}$ is halogen (the halogen has the same meaning as Hal defined above); and at least one of $R^{3e}$, $R^{4b}$, $R^{5b}$, $R^{6b}$ and $R^{7b}$ is hydrogen.

Compound (Ik) can be obtained by catalytic hydrogenation of Compound (Ij) in a solvent such as DMF, AcOEt and a mixture thereof in the presence or absence of a base such as potassium acetate in the presence of a catalyst such as tetrakis (triphenylphosphine) palladium and 10% Pd/C.

Based on Compound (Ij), 10 to 100% (by weight) or 0.1 to 10 equivalents of the reduction catalyst is used, and 0 to 10 equivalents of the base is used. The reaction is carried out at 0° to 180° C. for 5 minutes to 24 hours.

Step 6-22

In the formulae, at least one of $R^{3d}$, $R^{4a}$, $R^{5a}$, $R^{6a}$ and $R^{7a}$ is $OR^{11p}$ (wherein $R^{11p}$ is the same meaning as defined above); and at least one of $R^{3e}$, $R^{4b}$, $R^{5b}$, $R^{6b}$ and $R^{7b}$ is $OR^{11q}$ {wherein $R^{11q}$ is $NR^{17}R^{18}R^{19}$Hal-substituted lower alkyl (wherein $R^{17}$, $R^{18}$, $R^{19}$ and Hal are the same meanings as defined above)}.

Compound (Ik) can be obtained by reacting Compound (Ij) with the above-mentioned Compound (XIII in a solvent such as DMF, chloroform and a mixture thereof.

Compound (XIII) is used in an amount of 1 to 20 equivalents based on Compound (Ij). The reaction is carried out at 0° to 180° C. for 5 minutes to 24 hours.

Step 6-23

In the formulae, at least one of $R^{3d}$, $R^{4a}$, $R^{5a}$, $R^{6a}$ and $R^{7a}$ is hydroxy; and at least one of $R^{3e}$, $R^{4b}$, $R^{5b}$, $R^{6b}$ and $R^{7b}$ is methoxy.

In a solvent such as methylene chloride, THF, acetonitrile, methanol and a mixture thereof, Compound (Ik) can be obtained by reacting Compound (Ij) with diazomethane, or by reacting with (trimethylsilyl)diazomethane in the presence of a base such as diisopropylethylamine.

Diazomethane, diisopropylethylamine, and (trimethylsilyl)diazomethane are each used in an amount of 1 to 50 equivalents based on Compound (Ij). The reaction is carried out at −20° to 80° C. for 5 minutes to 48 hours.

Step 6-24

In the formulae, at least one of $R^{3d}$, $R^{4a}$, $R^{5a}$, $R^{6a}$ and $R^{7a}$ is $OR^{11r}$ (wherein $R^{11r}$ is chloro-substituted lower alkyl); and at least one of $R^{3e}$, $R^{4b}$, $R^{5b}$, $R^{6b}$ and $R^{7b}$ is $OR^{11s}$ (wherein $R^{11s}$ is iodo-substituted lower alkyl).

In a solvent such as DMF, Compound (Ik) can be obtained by reacting Compound (Ij) with sodium iodide or potassium iodide.

Sodium iodide or potassium iodide is used in an amount of 1 to 200 equivalents based on Compound (Ij). The reaction is carried out at 0° to 120° C. for 1 to 24 hours.

Step 6-25

In the formulae, at least one of $R^{3d}$, $R^{4a}$, $R^{5a}$, $R^{6a}$ and $R^{7a}$ is $OR^{11i}$ (wherein $R^{11i}$ is the same meaning as defined above); and at least one of $R^{3e}$, $R^{4b}$, $R^{5b}$, $R^{6b}$ and $R^{7b}$ is $OR^{11r}$ (wherein $R^{11r}$ is p-toluenesulfonyloxy-substituted lower alkyl).

Compound (Ik) can be obtained by reacting Compound (Ij) with p-toluenesulfonyl chloride in a solvent such as methylene chloride or 1,2-dichloroethane in the presence of a base such as pyridine.

The base and p-toluenesulfonyl chloride are each used in an amount of 1 to 20 equivalents based on Compound (Ij). The reaction is carried out at 0° to 120° C. for 1 to 48 hours.

Step 6-26

In the formulae, at least one of $R^{3d}$, $R^{4a}$, $R^{5a}$, $R^{6a}$ and $R^{7a}$ is $OR^{11m}$ (wherein $R^{11m}$ is the same meaning as defined above); and at least one of $R^{3e}$, $R^{4b}$, $R^{5b}$, $R^{6b}$ and $R^{7b}$ is $OR^{11i}$ (wherein $R^{11i}$ is as defined above).

Compound (Ik) can be obtained by reacting Compound (Ij) with a reducing agent in a solvent such as THF.

As the reducing agent, borane-dimethylsulfide complex, borane-THF complex, or the like is used. The reducing agent is used in an amount of 0.3 to 20 equivalents based on Compound (Ij). The reaction is carried out at −20° to 100° C. for 30 minutes to 24 hours.

The functional group contained in a substituent of $R^2$, $R^3$, $R^4$, $R^5$, $R^6$, $R^7$ or $R^8$ can be converted according to known methods [e.g., R. C. Larock, Comprehensive Organic Transformations, (1989)] in addition to the above-mentioned steps.

By appropriate combination of the above-mentioned methods, Compound (I) which have the desired functional group at the desired position can be obtained.

The product obtained by the above-mentioned processes can be isolated and purified by techniques conventionally used in organic syntheses such as filtration, extraction, washing, drying, concentration, recrystallization and various kinds of chromatography. The reaction intermediates may be subjected to subsequent reactions without purification.

Some of Compound (I) may exist in isomers such as position isomers, geometrical isomers and optical isomers, and the present invention covers all possible isomers and mixtures thereof at any mixing ratio.

In the case where a salt of Compound (I) is desired and it is produced in the form of the desired salt, it can be subjected to purification as such. In the case where Compound (I) is produced in the free state and its salt is desired, Compound (I) is dissolved or suspended in an appropriate solvent, followed by addition of an acid or a base to form a salt.

Compound (I) and pharmaceutically acceptable salts thereof may exist in the form of adducts with water or various kinds of solvents, which are also included in the scope of the present invention.

Tables 1, 2, 3 and 4 show examples of Compound (I).

TABLE 1

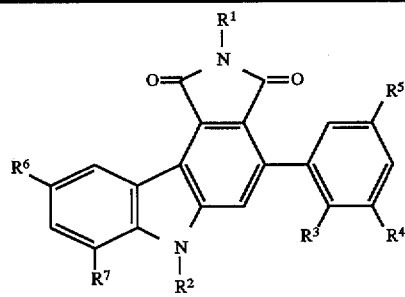

| Compd. No. | $R^1$ | $R^2$ | $R^3$ | $R^4$ | $R^5$ | $R^6$ | $R^7$ | Salt |
|---|---|---|---|---|---|---|---|---|
| 1 | Bn | H | $NO_2$ | H | H | H | H | |
| 2 | Bn | Me | $NO_2$ | H | H | H | H | |
| 3 | Bn | allyl | $NO_2$ | H | H | H | H | |
| 4 | Bn | $(CH_2)_3Br$ | $NO_2$ | H | H | H | H | |
| 5 | Bn | H | $NH_2$ | H | H | H | H | |
| 6 | Bn | $CH_2OH$ | $NMe_2$ | H | H | H | H | |
| 7 | Bn | H | $NMe_2$ | H | H | H | H | HCl |
| 8 | Bn | H | $NHCOCH_2NHZ$ | H | H | H | H | |
| 9 | Bn | H | $NHCOCH_2NH_2$ | H | H | H | H | HCl |
| 10 | Me | H | $NO_2$ | H | H | H | H | |
| 11 | Me | H | $NH_2$ | H | H | H | H | HCl |
| 12 | Me | $CH_2OH$ | $NMe_2$ | H | H | H | H | |
| 13 | Me | H | $NMe_2$ | H | H | H | H | HCl |
| 14 | Me | Me | $NO_2$ | H | H | H | H | |
| 15 | Me | Me | $NH_2$ | H | H | H | H | |
| 16 | Me | $CH_2$-⟨C₆H₄⟩-$NO_2$ | $NO_2$ | H | H | H | H | |
| 17 | Me | $CH_2$-⟨C₆H₄⟩-$NH_2$ | $NH_2$ | H | H | H | H | 2HCl |

TABLE 1-continued

[Structure diagram: substituted carbazole/biphenyl with R¹ on imide N, R² on indole N, R³–R⁷ on aromatic rings]

| Compd. No. | R¹ | R² | R³ | R⁴ | R⁵ | R⁶ | R⁷ | Salt |
|---|---|---|---|---|---|---|---|---|
| 18 | Me | CH₂-C₆H₄-NMe₂ | NMe₂ | H | H | H | H | 2HCl |
| 19 | Me | (CH₂)₂Br | NO₂ | H | H | H | H | |
| 20 | Me | (CH₂)₂NMe₂ | NO₂ | H | H | H | H | |
| 21 | Me | (CH₂)₂NMe₂ | NH₂ | H | H | H | H | 2HCl |
| 22 | Me | (CH₂)₃Br | NO₂ | H | H | H | H | |
| 23 | Me | (CH₂)₃NH₂ | NO₂ | H | H | H | H | HCl |
| 24 | Me | (CH₂)₃NMe₂ | NO₂ | H | H | H | H | HCl |
| 25 | Me | (CH₂)₃NMe₂ | NH₂ | H | H | H | H | 2HCl |
| 26 | Me | (CH₂)₃NMe₂ | NMe₂ | H | H | H | H | 2HCl |
| 27 | Me | (CH₂)₃NEt₂ | NO₂ | H | H | H | H | |
| 28 | Me | (CH₂)₃NEt₂ | NH₂ | H | H | H | H | |
| 29 | Me | (CH₂)₃N-morpholino | NO₂ | H | H | H | H | HCl |
| 30 | Me | (CH₂)₄Br | NO₂ | H | H | H | H | |
| 31 | Me | (CH₂)₄NH₂ | NO₂ | H | H | H | H | HCl |
| 32 | Me | (CH₂)₄NMe₂ | NO₂ | H | H | H | H | HCl |
| 33 | Me | (CH₂)₄NMe₂ | NH₂ | H | H | H | H | 2HCl |
| 34 | Me | (CH₂)₄N-morpholino | NO₂ | H | H | H | H | HCl |
| 35 | Me | (CH₂)₃NMe₂ | NH(CH₂)₂Br | H | H | H | H | |
| 36 | Me | (CH₂)₃NMe₂ | NH(CH₂)₂NMe₂ | H | H | H | H | 3HCl |
| 37 | Me | Me | NH(CH₂)₂OH | H | H | H | H | HCl |
| 38 | Me | Me | NH(CH₂)₂Br | H | H | H | H | |
| 39 | Me | Me | NH(CH₂)₂NH₂ | H | H | H | H | 2HCl |
| 40 | Me | Me | NH(CH₂)₂NMe₂ | H | H | H | H | 2HCl |
| 41 | Me | Me | NMe(CH₂)₂NMe₂ | H | H | H | H | 2HCl |
| 42 | Me | Me | NH(CH₂)₂NEt₂ | H | H | H | H | 2HCl |
| 43 | Me | Me | NH(CH₂)₂N-morpholino | H | H | H | H | 2HCl |
| 44 | Me | Me | NHZ | H | H | H | H | |
| 45 | Me | Me | NZ(CH₂)₂NMe₂ | H | H | H | H | |
| 46 | Me | Me | NZ(CH₂)₃Br | H | H | H | H | |
| 47 | Me | Me | NZ(CH₂)₃NHMe | H | H | H | H | |
| 48 | Me | Me | NZ(CH₂)₃NMe₂ | H | H | H | H | |
| 49 | Me | Me | NZ(CH₂)₃NEt₂ | H | H | H | H | |
| 50 | Me | Me | NZ(CH₂)₃NMen–Pr | H | H | H | H | |
| 51 | Me | Me | NH(CH₂)₃NMe₂ | H | H | H | H | 2HCl |
| 52 | Me | Me | NH(CH₂)₃NEt₂ | H | H | H | H | 2HCl |
| 53 | Me | Me | NH(CH₂)₃NMen–Pr | H | H | H | H | 2HCl |
| 54 | Me | Me | NHCOCH₃ | H | H | H | H | |
| 55 | Me | Me | NHCOCH₂Cl | H | H | H | H | |
| 56 | Me | Me | NHCOCH₂NMe₂ | H | H | H | H | HCl |
| 57 | Me | Me | NHCOCH₂NEt₂ | H | H | H | H | HCl |
| 58 | Me | Me | NHCO(CH₂)₂Br | H | H | H | H | |

TABLE 1-continued

| Compd. No. | R¹ | R² | R³ | R⁴ | R⁵ | R⁶ | R⁷ | Salt |
|---|---|---|---|---|---|---|---|---|
| 59 | Me | Me | $NHCO(CH_2)_2NMe_2$ | H | H | H | H | HCl |
| 60 | Me | Me | $NHCO(CH_2)_2NEt_2$ | H | H | H | H | HCl |
| 61 | Me | H | $NHCOCH_2NHZ$ | H | H | H | H | |
| 62 | Me | H | $NHCOCH_2NH_2$ | H | H | H | H | HCl |
| 63 | Me | H | NHCO—[pyrrolidine-N-Boc] | H | H | H | H | |
| 64 | Me | H | NHCO—[pyrrolidine-NH] | H | H | H | H | HCl |
| 65 | Me | Me | OH | H | H | H | H | |
| 66 | Me | Me | $O(CH_2)_2NMe_2$ | H | H | H | H | HCl |
| 67 | Me | Me | $O(CH_2)_2NEt_2$ | H | H | H | H | HCl |
| 68 | Me | Me | NHZ | H | H | Ac | H | |
| 69 | Me | Me | NHZ | H | H | OAc | H | |
| 70 | Me | Me | NHZ | H | H | OH | H | |
| 71 | Me | Me | NHZ | H | H | OBn | H | |
| 72 | Me | Me | $NZ(CH_2)_2NMe_2$ | H | H | OBn | H | |
| 73 | Me | Me | $NH(CH_2)_2NMe_2$ | H | H | OH | H | 2HCl |
| 74 | Me | Me | $NZ(CH_2)_2NMe_2$ | H | H | $NO_2$ | H | |
| 75 | Me | Me | $NZ(CH_2)_2NMe_2$ | H | H | H | $NO_2$ | |
| 76 | Me | Me | $NH(CH_2)_2NMe_2$ | H | H | $NO_2$ | H | 2HCl |
| 77 | Me | Me | $NH(CH_2)_2NMe_2$ | H | H | H | $NO_2$ | 2HCl |
| 78 | Me | Me | $NH(CH_2)_2NMe_2$ | $NO_2$ | H | H | H | 2HCl |
| 79 | Me | Me | $NH(CH_2)_2NMe_2$ | H | $NO_2$ | H | H | 2HCl |
| 80 | Me | Me | $NH(CH_2)_2NMe_2$ | $NO_2$ | $NO_2$ | $NO_2$ | H | |
| 81 | Me | Me | $NH(CH_2)_2NMe_2$ | H | H | $NH_2$ | H | |
| 82 | Me | Me | $NH(CH_2)_2NMe_2$ | H | Br | H | H | 2HCl |
| 83 | Me | Me | $NH(CH_2)_2NMe_2$ | Br | Br | Br | H | 2HCl |
| 84 | Me | H | NHAc | H | H | Ac | H | |
| 85 | Me | Me | NHAc | H | H | $COCH_2Cl$ | H | |
| 86 | Me | Me | NHAc | H | H | $NO_2$ | H | |
| 87 | Me | Me | NHAc | $NO_2$ | H | $NO_2$ | $NO_2$ | |
| 88 | Me | Me | $NAc(CH_2)_2NMe_2$ | H | $NO_2$ | H | H | |
| 89 | Me | Me | $NAc(CH_2)_2NMe_2$ | H | $NO_2$ | $NO_2$ | H | |
| 90 | Me | Me | $NAc(CH_2)_2NMe_2$ | H | $NO_2$ | H | $NO_2$ | |
| 91 | Me | Me | $NAc(CH_2)_2NMe_2$ | H | $NH_2$ | $NH_2$ | H | |

TABLE 2

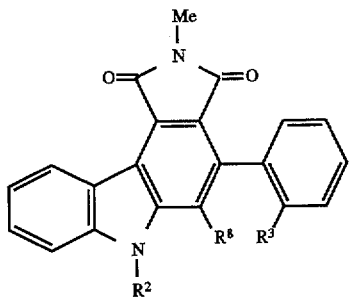

| Compd. No. | R² | R³ | R⁸ | Salt |
|---|---|---|---|---|
| 92 | Me | —NHCO— | | |
| 93 | Me | —N(CH₂)₂NMe₂CO— | | HCl |
| 94 | (CH₂)₃NEt₂ | —NHCO— | | |

TABLE 3

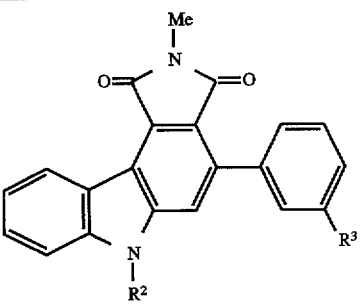

| Compd. No. | R² | R⁴ | Salt |
|---|---|---|---|
| 95 | CH₂O(CH₂)₂SiMe₃ | NO₂ | |
| 96 | CH₂O(CH₂)₂SiMe₃ | NH₂ | |
| 97 | CH₂O(CH₂)₂SiMe₃ | NHZ | |
| 98 | CH₂O(CH₂)₂SiMe₃ | NZ(CH₂)₂NMe₂ | |
| 99 | H | NZ(CH₂)₂NMe₂ | |
| 100 | H | NH(CH₂)₂NMe₂ | HCl |

TABLE 4

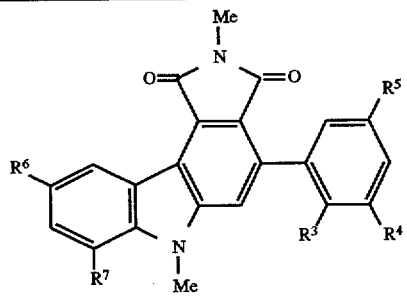

| Compd. No. | R³ | R⁴ | R⁵ | R⁶ | R⁷ | Salt |
|---|---|---|---|---|---|---|
| 101 | OAc | H | H | H | H | |
| 102 | OCHMeCH₂NMe₂ | H | H | H | H | HCl |
| 103 | OCH₂CHMeNMe₂ | H | H | H | H | |
| 104 | O(CH₂)₃NMe₂ | H | H | H | H | HCl |
| 105 | O(CH₂)₂OH | H | H | H | H | |
| 106 | O(CH₂)₂OMe | H | H | H | H | |
| 107 | O(CH₂)₂CHMe₂ | H | H | H | H | |
| 108 | OCHMeCOMe | H | H | H | H | |
| 109 | OCHMeCO₂Me | H | H | H | H | |
| 110 | OCHMeCO₂H | H | H | H | H | |
| 111 | OCHMeCONMe₂ | H | H | H | H | |
| 112 | OCHEtCONMe₂ | H | H | H | H | |
| 113 | OCHEtCH₂NMe₂ | H | H | H | H | |
| 114 | O(CH₂)₂Cl | H | H | H | H | |
| 115 | O(CH₂)₂I | H | H | H | H | |
| 116 | O(CH₂)₂NH₂ | H | H | H | H | HCl |
| 117 | O(CH₂)₂NHMe | H | H | H | H | HCl |
| 118 | O(CH₂)₂NHn—Pr | H | H | H | H | HCl |
| 119 | O(CH₂)₂NMen—Pr | H | H | H | H | HCl |
| 120 | O(CH₂)₂NHi—Pr | H | H | H | H | HCl |
| 121 | O(CH₂)₂NMei—Pr | H | H | H | H | HCl |
| 122 | O(CH₂)₂NH-cyclopentyl | H | H | H | H | HCl |

TABLE 4-continued

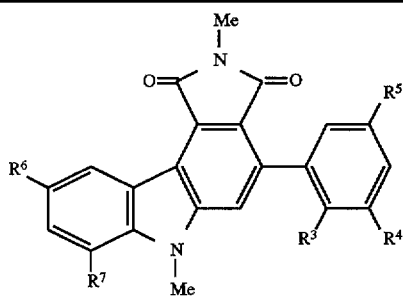

| Compd. No. | R³ | R⁴ | R⁵ | R⁶ | R⁷ | Salt |
|---|---|---|---|---|---|---|
| 123 | OAc | H | F | H | H | |
| 124 | OH | H | F | H | H | |
| 125 | O(CH₂)₂NMe₂ | H | F | H | H | |
| 126 | OAc | H | Cl | H | H | |
| 127 | OH | H | Cl | H | H | |
| 128 | O(CH₂)₂NMe₂ | H | Cl | H | H | |
| 129 | OH | H | Br | H | H | |
| 130 | O(CH₂)₂NMe₂ | H | Br | H | H | HCl |
| 131 | OCHMeCH₂NMe₂ | H | Br | H | H | |
| 132 | OCH₂CHMeNMe₂ | H | Br | H | H | |
| 133 | O(CH₂)₂OH | H | Br | H | H | |
| 134 | OAc | H | Br | F | H | |
| 135 | OH | H | Br | F | H | |
| 136 | O(CH₂)₂NMe₂ | H | Br | F | H | |
| 137 | OAc | H | H | Cl | H | |
| 138 | OH | H | H | Cl | H | |
| 139 | O(CH₂)₂NMe₂ | H | H | Cl | H | HCl |
| 140 | OAc | H | H | Br | H | |
| 141 | OH | H | H | Br | H | |
| 142 | O(CH₂)₂NMe₂ | H | H | Br | H | |
| 143 | OH | H | Br | Br | H | |
| 144 | O(CH₂)₂NMe₂ | H | Br | Br | H | |
| 145 | OAc | H | OBn | H | H | |
| 146 | OH | H | OBn | H | H | |
| 147 | O(CH₂)₂NMe₂ | H | OBn | H | H | |
| 148 | O(CH₂)₂NMe₂ | H | OH | H | H | |
| 149 | O(CH₂)₂NMe₂ | H | OMe | H | H | |
| 150 | O(CH₂)₂NMe₂ | H | Oi—Pr | H | H | |
| 151 | O(CH₂)₂NMe₂ | H | OCH₂-C₆H₄-Cl | H | H | |
| 152 | O(CH₂)₂NMe₂ | H | OCH₂-(2-pyridyl) | H | H | |
| 153 | O(CH₂)₂NMe₂ | H | OCH₂-(3-pyridyl) | H | H | |
| 154 | O(CH₂)₂NMe₂ | H | OCH₂-naphthyl | H | H | |
| 155 | O(CH₂)₂NMe₂ | H | OAc | H | H | HCl |
| 156 | O(CH₂)₂NMe₂ | H | OCOn—Bu | H | H | HCl |
| 157 | OH | H | OH | H | H | |
| 158 | O(CH₂)₂Cl | H | H | Br | H | |
| 159 | O(CH₂)₂Cl | H | CHO | Br | H | |
| 160 | O(CH₂)₂NMe₂ | H | CHO | Br | H | |
| 161 | O(CH₂)₂NMe₂ | H | CHO | H | H | |
| 162 | OBn | H | H | Br | H | |
| 163 | OAc | H | Ac | Br | H | |

TABLE 4-continued

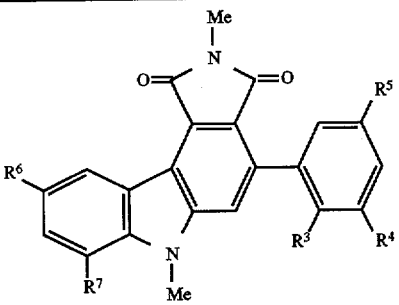

| Compd. No. | R³ | R⁴ | R⁵ | R⁶ | R⁷ | Salt |
|---|---|---|---|---|---|---|
| 164 | O(CH₂)₂NMe₂ | H | Ac | Br | H | |
| 165 | OH | H | NO₂ | H | H | |
| 166 | OH | NO₂ | H | H | H | |
| 167 | O(CH₂)₂Cl | H | NO₂ | H | H | |
| 168 | O(CH₂)₂NMe₂ | H | NO₂ | H | H | |
| 169 | O(CH₂)₂NMe₂ | H | NH₂ | H | H | |
| 170 | O(CH₂)₂NMe₂ | H | NMe₂ | H | H | |
| 171 | O(CH₂)₂NMe₂ | H | NHAc | H | H | |
| 172 | O(CH₂)₂NMe₂ | H | NHBz | H | H | |
| 173 | OAc | H | H | CHO | H | |
| 174 | OH | H | H | CHO | H | |
| 175 | O(CH₂)₂Cl | H | H | CHO | H | |
| 176 | O(CH₂)₂I | H | H | CHO | H | |
| 177 | O(CH₂)₂NMe₂ | H | H | CHO | H | |
| 178 | OAc | H | H | Ac | H | |
| 179 | OH | H | H | Ac | H | |
| 180 | O(CH₂)₂NMe₂ | H | H | Ac | H | |
| 181 | OAc | H | H | NO₂ | H | |
| 182 | OAc | H | H | H | NO₂ | |
| 183 | OH | H | H | NO₂ | H | |
| 184 | O(CH₂)₂NMe₂ | H | H | NO₂ | H | HCl |
| 185 | O(CH₂)₂NMe₂ | H | H | NH₂ | H | 2HCl |
| 186 | O(CH₂)₂NMe₂ | H | H | NMe₂ | H | 2HCl |
| 187 | O(CH₂)₂NMe₂ | H | H | NHAc | H | HCl |
| 188 | O(CH₂)₂NMe₂ | H | H | NHBz | H | HCl |
| 189 | O(CH₂)₂Cl | H | H | OCHO | H | |
| 190 | O(CH₂)₂NMe₂ | H | H | OH | H | HCl |
| 191 | O(CH₂)₂NMe₂ | H | H | OMe | H | HCl |
| 192 | O(CH₂)₂NMe₂ | H | H | Oi—Pr | H | HCl |
| 193 | O(CH₂)₂NMe₂ | H | H | OBn | H | HCl |
| 194 | O(CH₂)₂NMe₂ | H | H | OAc | H | HCl |
| 195 | O(CH₂)₂NMe₂ | H | H | OCOEt | H | HCl |
| 196 | O(CH₂)₂NMe₂ | H | H | OCOn—Bu | H | HCl |
| 197 | O(CH₂)₂NMe₂ | H | H | OBz | H | HCl |
| 198 | OH | F | H | H | H | |
| 199 | O(CH₂)₂NMe₂ | F | H | H | H | HCl |
| 200 | OH | Br | Br | H | H | |
| 201 | O(CH₂)₂NMe₂ | Br | Br | H | H | HCl |
| 202 | O(CH₂)₂NMe₂ | NO₂ | H | H | H | |
| 203 | O(CH₂)₂NMe₂ | NH₂ | H | H | H | |
| 204 | O(CH₂)₂NMe₂ | NMe₂ | H | H | H | |
| 205 | O(CH₂)₂NMe₂ | NHAc | H | H | H | HCl |
| 206 | O(CH₂)₂NMe₂ | NHCO₂Me | H | H | H | HCl |
| 207 | OH | OBn | H | H | H | |
| 208 | O(CH₂)₂NMe₂ | OBn | H | H | H | HCl |
| 209 | O(CH₂)₂NMe₂ | OH | H | H | H | HCl |
| 210 | O(CH₂)₂NMe₂ | O(CH₂)₂NMe₂ | H | H | H | 2HCl |
| 211 | O(CH₂)₂NMe₂ | OAc | H | H | H | HCl |
| 212 | O(CH₂)₂NMe₃I | OH | H | H | H | |
| 213 | OH | OMe | H | H | H | |
| 214 | O(CH₂)₂NMe₂ | OMe | H | H | H | HCl |
| 215 | 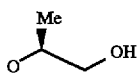 | H | H | H | H | |
| 216 | 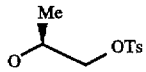 | H | H | H | H | |

TABLE 4-continued

[Structure: central benzene ring with N-Me imide (two C=O groups and N-Me at top), with two phenyl substituents bearing R3, R4, R5, R6, R7 groups, and an N-Me on the central ring]

| Compd. No. | R³ | R⁴ | R⁵ | R⁶ | R⁷ | Salt |
|---|---|---|---|---|---|---|
| 217 | Me, O-CH(-)-CH₂Cl | H | H | H | H | |
| 218 | Me, O-CH(-)-CH₂NMe₂ | H | H | H | H | HCl |
| 219 | Me, O-CH(⋮)-CH₂OH | H | H | H | H | |
| 220 | Me, O-CH(⋮)-CH₂OTs | H | H | H | H | |
| 221 | Me, O-CH(⋮)-CH₂Cl | H | H | H | H | |
| 222 | Me, O-CH(-)-CH₂NMe₂ | H | H | H | H | HCl |
| 223 | O(CH₂)₂NMe₂ | H | OBz | H | H | HCl |
| 224 | OCHMeCH₂NMe₂ | H | H | Ac | H | |
| 225 | OCH₂CHMeNMe₂ | H | H | Ac | H | |
| 226 | OCHMeCH₂OH | H | H | H | H | |
| 227 | OCHMeCH₂OTs | H | H | H | H | |
| 228 | OCHMeCH₂NEt₂ | H | H | H | H | HCl |
| 229 | OAc | H | H | H | CHO | |
| 230 | OH | H | H | H | CHO | |
| 231 | O(CH₂)₂NMe₂ | H | H | H | CHO | HCl |

Compound (I) or pharmaceutically acceptable salts thereof can be administered as they are or in the form of various pharmaceutical compositions according to their pharmacological effect and the purpose of administration. Pharmaceutical compositions produced in accordance with the present invention can be prepared by uniformly mixing an effective amount of Compound (I), or pharmaceutically acceptable salts thereof, as an active ingredient, with a pharmaceutically acceptable carrier. The carrier may have a wide range form depending on the type of preparation desired for the administration. It is desired that pharmaceutical compositions are prepared in a unit dose form suitable for oral administration or non-oral administration such as through ointments and injections.

Tablets can be prepared in a conventional manner, using an excipient such as lactose, glucose, sucrose, mannitol and methyl cellulose; a disintegrating agent such as starch, sodium alginate, calcium carboxymethyl cellulose and crystalline cellulose; a lubricant such as magnesium stearate and talc; a binder such as gelatin, polyvinyl alcohol, polyvinylpyrrolidone, hydroxypropyl cellulose and methyl cellulose; and a surfactant such as a sucrose fatty acid ester and a sorbitol fatty acid ester. Tablet containing 10 to 200 mg of an active ingredient are preferable.

Granules can be prepared in a conventional manner, using an excipient such as lactose and sucrose; a disintegrating agent such as starch; and a binder such as gelatin. Powders are prepared in a conventional manner, using an excipient such as lactose and mannitol. Capsules are prepared in a conventional manner, using gelatin, water, sucrose, gum arabic, sorbitol, glycerin, crystalline cellulose, magnesium stearate and talc. Capsules containing 10 to 200 mg an active ingredient are preferable.

Syrups are prepared in a conventional manner, using water, ethanol, and a sugar such as sucrose.

Ointments are prepared in a conventional manner, using an ointment base such as vaseline, liquid paraffin, lanolin and macrogol, and an emulsifying agent such as sodium lauryl lactate, benzalkonium chloride, sorbitan monofatty acid ester, sodium carboxymethyl cellulose and gum arabic.

Injectable preparations can be prepared in a conventional manner, using, a solvent such as water, physiological saline, vegetable oil including olive oil and peanut oil, ethyl oleate, and propylene glycol; a solubilizing agent such as sodium benzoate, sodium salicylate and urethane; an isotonizing agent such as sodium chloride and glucose; a preservative such as phenol, cresol, p-hydrozybenzoic ester and chlorobutanol; and an antioxidant such as ascorbic acid and sodium pyrosulfite.

Compound (I) or pharmaceutically acceptable salts thereof can be administered orally or non-orally, e.g. through ointments and injections. The effective dose and the administration schedule vary depending on the route of administration, the age, body weight and symptoms of the patient, etc., however, general daily dose is preferably 0.1 to 50 mg/kg.

The toxicity and pharmacological activity of Compound (I) will be described in the following Test Examples.

Test Example 1

Megakaryocyte Colony Formation-Stimulating Activity

An eight-week-old Balb/c mouse was killed. Its femurs and cervical vertebrae were taken out and both ends thereof were cut off. Bone marrow cells were collected from the pieces cut off from the femurs and cervical vertebrae using a syringe containing IMDM (430-2200EA manufactured by Gibco Co.), and blown into a test tube. The test tube was allowed to stand for 5 minutes, and the supernatant was collected with a pipet. Each of the test compounds at various concentrations was separately added to a separate reaction mixture corltaining the bone marrow cells (50,000 cells), bovine serum albumin (2%: A4508, manufactured by Sigma Co.), transferrin (600 μg/ml: 652202, manufactured by Boehringer Mannheim Co.), IL-3 (100 U/ml), cholesterol (16 μg/ml: 036-0641, manufactured by Wako Co.) and agar (0.6%: 0142-02, manufactured by Difco Laboratories); Then, 1 ml each of the mixtures was put into a 35-mm dishes (manufactured by Lux Co.); and cultured at 37° C., 5% $CO_2$, and relative humidity of not less than 95%, for 7 days. A control was prepared by adding IL-3 alone to the bone marrow cells. After the completion of the culturing, the resultant agar was dried by using filter paper (1001-055, manufactured by Whatman Co.), fixed with 2.5% glutaraldehyde, followed by acetylcholinesterase staining (ACHE staining).

ACHE staining was carried out according to the following method:

ACHE staining: To each sample was added a solution containing 0.67 mg/ml acetylthiocholine iodide, 2.94 mg/ml sodium citrate, 7.5 mg/ml copper (II) sulfate, and 1.65 mg/ml potassium ferricyanide. Then, the mixture was allowed to stand at room temperature in the dark for 4 to 6 hours.

A group of 4 or more megakaryocytes which were stained reddish brown was regarded as one colony, and the number of colonies per dish was calculated using a microscope.

The results are shown in Table 5 as values relative to the control. (In the table, the relative values were calculated on the basis of the control defined as 100).

TABLE 5

Stimulating Effect of Compound(I) on Megakaryocyte Colony Formation

| Compd. | Conc. (nM) | Rel. Value |
|---|---|---|
| Control |  | 100 |
| 1 | 1 | 147 |

TABLE 5-continued

Stimulating Effect of Compound(I) on Megakaryocyte Colony Formation

| Compd. | Conc. (nM) | Rel. Value |
|---|---|---|
| 5 | 1 | 117 |
| 10 | 1 | 120 |
| 11 | 10 | 128 |
| 17 | 1 | 123 |
| 24 | 1 | 125 |
| 26 | 10 | 110 |
| 34 | 0.1 | 114 |
| 36 | 10 | 149 |
| 37 | 1 | 130 |
| 40 | 1 | 138 |
| 51 | 10 | 141 |
| 56 | 1 | 116 |
| 60 | 1 | 110 |
| 66 | 10 | 119 |
| 82 | 10 | 119 |
| 93 | 0.1 | 119 |
| 102 | 1 | 142 |
| 160 | 10 | 120 |
| 170 | 1 | 125 |
| 177 | 10 | 120 |

Test Example 2

Platelet Production-Stimulating Activity in Mice

A test compound was intraperitoneally (i. p.) or subcutaneously (s. c.) administered to 7-week-old male Balb/c mice once a day for consecutive 5 days (test group, 4 mice per group). A control group (4 mice per group) was administered only a solvent (5% Tween 80/water) alone. On the 15th day from the start of the administration, blood was collected from the fundus oculi vein of each mouse, and the number of platelets was counted with a micro counter (Model CC-180A, manufactured by Toa Iryo Denshi Co.). The rate (%) of increase in the number of platelets in the test group which had been administered test compounds over the control group was calculated according to the following formula to evaluate the effect of the test compound.

[Ratio of increase]=$A/B \times 100$

A: the number of platelets in the test group
B: the number of platelets in the control group
The results are shown in Table 6.

TABLE 6

Stimulating Effect of Compound(I) on Platelet Production

| Compd. | Dose (mg/kg) | Adminstraion Route | Ratio of increase (%) |
|---|---|---|---|
| 5 | 50 | i.p. | 111 |
| 24 | 10 | i.p. | 125 |
| 40 | 50 | i.p. | 174 |
| 66 | 50 | i.p. | 206 |
| 79 | 25 | i.p. | 180 |
| 93 | 50 | i.p. | 176 |
| 102* | 10 | s.c. | 123 |
| 130* | 10 | s.c. | 295 |
| 147 | 10 | s.c. | 154 |
| 160 | 10 | s.c. | 117 |
| 170 | 10 | s.c. | 138 |
| 180 | 10 | s.c. | 189 |
| 203 | 10 | s.c. | 146 |

*free base

Test Example 3

Acute Toxicity Test

Each of the test compounds shown in Table 6 was administered to 7-week-old male Balb/c mice (4 mice per

EXAMPLE

Example 1

Compound 1

In 50 ml of collidine were dissolved 1.57 g (3.28 mmol) of N-benzyl-3,6-bis(2-nitrophenyl)phthalimide and 2.15 g (8.20 mmol) of triphenylphosphine, followed by stirring at 180° C. for 30 hours. The solvent was evaporated under reduced pressure and the residue was purified by silica gel column chromatography (toluene/AcOEt=30/1) to give 0.64 g (44%) of Compound 1.

$^1$HNMR(CDCl$_3$)∂; 4.77(s,2H), 7.20–7.60(m,12H), 7.99 (m,1H), 8.67(s,1H), 8.81(d,1H,J=8.0 Hz).

FABMS(m/z); 446(M−1)$^-$

Example 2

Compound 2

To a suspension of 12 mg (0.29 mmol) of 60% sodium hydride in 0.5 ml of DMF was added a solution of 100 mg (0.22 mmol) of Compound 1 in 1 ml of DMF at room temperature. After stirring for 30 minutes, 0.015 ml (0.25 mmol) of methyl iodide was added thereto at the same temperature, followed by further stirring for 2.5 hours. The solvent was evaporated under reduced pressure, and CHCl$_3$ was added to the residue. The solution was washed with brine, and dried over Na$_2$SO$_4$, followed by evaporation of the solvent. The residue was purified by silica gel column chromatography (toluene/CHCl$_3$/AcOEt=5/5/1) to give 86 mg (83%) of Compound 2.

$^1$HNMR(DMSO-d$_6$)∂; 4.03(s,3H), 4.75(s,2H), 7.13–7.51 (m,6H), 7.59–8.00(m,5H), 8.01(s,1H), 8.01(m,1H), 8.92(d, 1H,J=8.0 Hz).

FABMS(m/z); 446(M−1)$^-$

Example 3

Compound 3

According to Example 2, 46 mg (42%) of Compound 3 was obtained from 100 mg (0.22 mmol) of Compound 1, 12 mg (0.29 mmol) of sodium hydride and 0.021 ml (0.25 mmol) of allyl bromide.

$^1$HNMR(DMSO-d$_6$)∂; 4.76(m,2H), 5.00(dd,1H,J=1.5, 17.1 Hz), 5.14(dd,1H, J=1.4,10.3 Hz), 5.22(m,2H), 6.01(m, 1H), 7.12–7.35(m,5H), 7.41(dt,1H, J=0.8,7.7 Hz), 7.65(dd, 1H,J=1.5,7.6 Hz), 7.67(ddd,1H,J=1.2,7.7,8.6 Hz), 7.76(d, 1H,J=8.6 Hz), 7.77(m,1H), 7.88(dt,1H,J=1.3,7.6 Hz), 7.97 (s,1H), 8.23(dd,1H,J=1.3,8.2 Hz), 8.94(d,1H,J=7.7 Hz).

FABMS(m/z); 487(M)$^-$

Example 4

Compound 4

According to Example 2, 106 mg (83%) of Compound 4 was obtained from 100 mg (0.22 mmol) of Compound 1, 12 mg (0.29 mmol) of sodium hydride and 0.046 ml (0.45 mmol) of 1,3-dibromopropane.

$^1$HNMR(CDCl$_3$)∂; 2.49(m,2H), 3.39(m,2H), 4.40(m,1H), 4.58(m,1H), 4.82(m,2H), 7.12–7.78(m,12H), 8.04–8.25(m, 1H), 9.00–9.14(m,1H).

FABMS(m/z); 567(M)$^-$

Example 5

Compound 5

In 6 ml of a mixed solvent of DMF and AcOEt (1/11) was dissolved 200 mg (0.45 mmol) of Compound 1, then 87 mg of 10% Pd/C was added thereto, followed by stirring for 4 hours in a stream of hydrogen at room temperature. After filtering the reaction solution, the solvent was evaporated, and the residue was purified by silica gel column chromatography (CHCl$_3$/MeOH=30/1) to give 173 mg (93%) of Compound 5.

$^1$HNMR(DMSO-d$_6$)∂; 4.77(br s,4H), 6.50–6.80(m,2H), 6.92–7.70(m,11H), 8.90(d,1H,J=7.8 Hz), 12.0 2(s,1H).

FABMS(m/z); 418(M+1)$^+$

Example 6

Compound 6

To a solution of 120 mg (0.29 mmol) of Compound 5 in 8 ml of acetonitrile were added 4 ml (46.6 mmol) of 35% formalin and 200 mg (3.23 mmol) of sodium cyanoborohydride. The mixture was stirred at room temperature for 15 minutes, and the pH thereof was adjusted to 6 with 10% aqueous acetic acid, followed by stirring for 5 minutes. An aqueous saturated sodium hydrogencarbonate solution was added to the reaction mixture, followed by extraction with methylene chloride. The extract was washed with brine, dried over Na$_2$SO$_4$, and evaporated. The residue was purified by silica gel column chromatography (CHCl$_3$) to give 114 mg (89%) of Compound 6.

$^1$HNMR(CDCl$_3$)∂; 2.43(s,6H), 3.35(m,1H), 4.83(s,2H), 5.76(d,2H, J=5.6 Hz), 6.89–7.61(m,12H), 7.68(s,1H), 8.70 (d,1H,J=7.8 Hz).

FABMS(m/z); 476(M+1)$^+$

Example 7

Compound 7

In 4 ml of a mixed solvent of DMF and MeOH (1/1) was dissolved 100 mg (0.21 mmol) of Compound 6, then 2 drops of 1N aqueous sodium hydroxide was added thereto, followed by stirring at room temperature for 10 minutes. Water was added to the reaction mixture, followed by extraction with methylene chloride. The extract was washed with water and then with brine, dried over Na$_2$SO$_4$, and evaporated. The residue was purified by silica gel column chromatography (toluene/AcOEt=10/1) and recrystallized from CHCl$_3$-n-hexane to give 80 mg (85%) of a free base of Compound 7.

In 5 ml of a mixed solvent of DMF and AcOEt (1/4) was dissolved 70 mg (0.16 mmol) of the free base of Compound 7, and 1 ml of 2N hydrochloric acid (AcOEt solution) was added thereto, followed by stirring at room temperature for 2 hours. The resulting precipitate was collected by filtration, washed with AcOEt, and dried under redfaced pressure to give 66 mg (87%) of Compound 7.

$^1$HNMR(DMSO-d$_6$)∂; 2.90(br s,6H), 4.77(s,2H), 7.21–7.65(m,10H), 7.59(t,1H,J=7.8 Hz), 7.65(d,1H,J=7.8 Hz), 7.75(s,1H) 8.89(d,1H,J=7.8Hz), 12.26(br,1H).

FABMS(m/z); 446(M+1)$^+$

Example 8

Compound 8

In 3 ml of DMF were dissolved 120 mg (0.29 mmol) of Compound 5 and 61 mg (0.29 mmol) of Z-glycine, then 0.093 ml (0.43 mmol) of diphenylphosphorylazide and 0.061 ml (0.43 mmol) of triethylamine were added thereto under an ice-cooled condition, followed by stirring at the same temperature for 15 hours. To the reaction mixture, 2N hydrochloric acid was added, followed by extraction with AcOEt. The extract was washed with an aqueous saturated sodium hydrogencarbonate solution and then with brine, dried over $Na_2SO_4$, and evaporated. The residue was triturated with $CHCl_3$ to give 106 mg (60%) of Compound 8.

$^1$HNMR(DMSO-$d_6$)∂; 3.50(m,2H), 4.75(br s,4H), 4.92(s, 1H), 6.80–8.80(m,18H), 8.61–8.98(m,2H), 12.09(s,1H).

FABMS(m/z); 609(M+1)$^+$

Example 9

Compound 9

According to Example 5, a free base of Compound 9 was obtained from 105 mg (0.17 mmol) of Compound 8 and 44 mg of 10% Pd/C. According to Example 7, 23 mg (27%) of Compound 9 was obtained.

$^1$HNMR(DMSO-$d_6$)∂; 3.45(d,2H,J=4.3 Hz), 4.80(m,2H), 7.24–7.38(m,7H), 7.42(dd,1H,J=1.2,7.5 Hz), 7.48(dt,1H, J=1.2,8.1 Hz), 7.59(ddd,1H, J=1.2,7.1,8.2 Hz), 7.60(s,1H), 7.65(dd,1H,J=0.8,8.2 Hz), 7.79(d,1H,J=8.1 Hz), 8.04(br s,3H), 8.91(d,1H,J=8.0Hz), 9.46(s,1H), 12.22(s,1H).

FABMS(m/z); 475(M+1)$^+$

Example 10

Compound 10

According to Example 1, 5.36 g (40%) of Compound 10 was obtained from 14.5 g (35.9 mmol) of N-methyl-3,6-bis (2-nitrophenyl)phthalimide prepared according to the above-mentioned known method and 18.8 g (71.7 mmol) of triphenylphosphine.

$^1$HNMR(DMSO-$d_6$)∂; 3.00(s,3H), 7.10–7.95(m,7H), 8.20m,1H), 8.83(d,1H,J=8.0 Hz), 12.18(br s,1H).

FABMS(m/z); 370(M–1)$^-$

Example 11

Compound 11

According to Example 5, 0.86 g (94%) of a free base of Compound 11 was obtained from 1.00 g (2.69 mmol) of Compound 10 and 300 mg of 10% Pd/C.

According to Example 7, 64 mg (54%) of Compound 11 was obtained from 100 mg (0.29 mmol) of the free base of Compound 11.

Free base

HNMR(DMSO-$d_6$)∂; 3.04(s,3H), 4.69(s,2H), 6.62(dt,1H, J=0.9,7.5 Hz), 6.75(dd,1H,J=0.9,8.1 Hz), 7.02(dd,1H,J=1.6, 7.5 Hz), 7.10(dt,1H,J=1.6,7.6 Hz), 7.32(dt,1H,J=1.0,8.0 Hz), 7.55(s,1H), 7.56(dt,1H,J=1.1,8.1 Hz), 7.61(d,1H,J=8.1 Hz), 8.91(d,1H,J=8.0), 11.96(s,1H).

FABMS(m/z); 342 (M+1)$^+$

Example 12

Compound 12

According to Example 6, 154 mg (52%) of Compound 12 was obtained from 250 mg (0.73 mmol) of Compound 11, 8 ml (93 mmol) of 35% formalin and 300 mg (4.84 mmol) of sodium cyanoborohydride.

$^1$HNMR(CDCl$_3$)∂; 2.47(s,6H), 3.11(s,3H), 5.81(s,2H), 6.95–7.56 (m,7H 7.69(s,1H), 8.92(d,1H,J=7.6 Hz).

FABMS(m/z); 400 (M+1)$^+$

Example 13

Compound 13

According to Example 7, 80 mg (69%) of a free base of Compound 13 was obtained from 125 mg (0.31 mmol) of Compound 12.

In 15 ml of CHCl$_3$ was dissolved 75 mg (0.20 mmol) of the free base of Compound 13, and 0.88N hydrochloric acid (AcOEt solution) was added thereto, followed by stirring at room temperature for 0.5 hours. The resulting precipitate was collected by filtration, washed with AcOEt, and dried under reduced pressure to give 78 mg (95%) of Compound 13.

Free base $^1$HNMR(CDCl$_3$)∂; 2.51(s,6H), 3.18(s,3H), 6.97–7.64(m, 7H), 7.59(s,1H), 8.63(br s,1H), 9.05(d,1H,J=7.3 Hz).

FABMS(m/z); 370(M+1)$^+$

Example 14

Compound 14

According to Example 2, 138 mg (67%) of Compound 14 was obtained from 200 mg (0.54 mmol) of Compound 10, 28 mg (0.70 mmol) of sodium hydride and 0.04 ml (0.65 mmol) of methyl iodide.

$^1$HNMR(DMSO-$d_6$)∂; 3.00(s,3H), 3.99(s,3H), 7.39(ddd, 1H,J=2.0,6.3,8.0 Hz), 7.50–8.00(m,5H), 7.94(s,1H), 8.25 (dd,1H,J=2.0,7.5 Hz), 8.90 (d,1H,J=7.8 Hz).

FABMS(m/z); 386(M+1)$^+$

Example 15

Compound 15

According to Example 5, 114 mg (100%) of Compound 15 was obtained from 118 mg (0.31 mmol) of Compound 14 and 35 mg of 10% Pd/C.

$^1$HNMR(CDCl$_3$)∂; 3.18(s,3H), 3.64(br, 2H), 3.89(s,3H), 6.86(dd,1H,J=1.1,8.2 Hz), 6.91(dt,1H,J=1.1,7.5 Hz), 7.18 (dd,1H,J=1.5,7.7 Hz), 7.28(ddd,1H,J=1.5,7.4,8.2 Hz), 7.39 (ddd,1H,J=0.9,7.3,8.0 Hz), 7.44(d,1H,J=8.3 Hz), 7.53(s, 1H), 7.62(ddd,1H,J=1.2,7.3,8.3 Hz), 9.07(ddd,1H, J=0.6, 1.2,8.0 Hz).

FABMS(m/z); 356(M+1)$^+$

Example 16

Compound 16

To a suspension of 56 mg (1.40 mmol) of 60% sodium hydride in 0.5 ml of DMF was added a solution of 400 mg (1.08 mmol) of Compound 10 in 2 ml of DMF at room temperature. After stirring for 30 minutes, 6 ml of toluene and a solution of 372 mg (1.72 mmol) of p-nitrobenzyl bromide in 0.7 ml of DMF were added, followed by stirring at 100° C. for 6 hours. After evaporating the solvent under reduced pressure, CHCl$_3$ was added to the residue. The solution was washed with brine, dried over $Na_2SO_4$, and evaporated. The residue was triturated with toluene to give 215 mg (39%) of Compound 16.

$^1$HNMR(DMSO-$d_6$)∂; 3.03(s,3H), 6.03(s,2H, 7.38(d,2H, J=8.8 Hz), 7.48–7.92(m,6H), 8.07(s,1H), 8.16(d,2H,J=8.8 Hz), 8.23(m,1H), 8.99(d,1H,J=7.6 Hz).

FABMS(m/z); 507(M+1)$^+$

Example 17

Compound 17

According to Example 5, 256 mg (95%) of a free base of Compound 17 was obtained from 305 mg (0.06 mmol) of Compound 16 and 90 mg of 10% Pd/C.

According to Example 7, 87 mg (89%) of Compound 17 was obtained from 84 mg (0.19 mmol) of the free base of Compound 17.

Free base $^1$HNMR(DMSO-$d_6$)∂; 3.05(s,3H), 4.69(s,2H), 4.97(s, 2H), 5.55(d,2H,J=2.0 Hz), 6.43(d,2H,J=8.3 Hz), 6.62(dt, 1H,J=0.9,7.5 Hz), 6.74(dd,1H,J=0.9,8.1 Hz), 6.93(d,2H,J= 8.3 Hz), 7.01(dd,1H,J=1.6,7.5 Hz), 7.10(dt,1H,J=1.6,7.5 Hz), 7.37(t,1H,J=7.6 Hz), 7.60(ddd,1H,J=1.0,7.3,8,3 Hz), 7.77(d,1H,J=8.3 Hz), 7.79(s,1H), 8.97(d,1H,J=7.8 Hz).

FABMS(m/z); 447(M+1)$^+$

Example 18

Compound 18

According to Example 6, 79 mg (64%) of a free base of Compound 18 was obtained from 10 mg to (0.24 mmol) of a free base of Compound 17, 2 ml (23.3 mmol) of 35% formalin and 136 mg (2.19 mmol) of sodium cyanoborohydride.

According to Example 13, 58 mg (64%) of Compound 18 was obtained from 79 mg (0.16 mmol) of the free base of Compound 18.

Free base $^1$HNMR(CDCl$_3$)∂; 2.42(s,6H), 2.85(s,6H),3.17(s,3H), 5.40(s,2H),6.57(d, 2H,J=8.8 Hz), 6.89–7.60(m,9H), 7.68(s, 1H), 9.13(d,1H,J=7.3 Hz).

FABMS(m/z); 503(M+1)$^+$

Example 19

Compound 19

According to Example 2, 27 mg (21%) of Compound 19 was obtained from 100 mg (0.27 mmol) of Compound 10, 15 mg (0.38 mmol) of sodium hydride and 0.09 ml (1.04 mmol) of 1,2-dibromoethane.

$^1$HNMR(CDCl$_3$)∂; 3.16(s,3H), 3.74(d,2H,J=7.2 Hz), 4.78 (d,2H,J=7.2 Hz), 7.45(m,1H), 7.49(dd,1H,J=1.0,7.8 Hz), 7.50(dd,1H,J=1.6,7.7 Hz), 7.51(s,1H), 7.65(m,2H), 7.74(dt, 1H,J=1.3,7.7 Hz), 8.24(dd,1H,J=1.3,8,3 Hz), 9.13(dd,1H,J= 1.0,7.9 Hz).

FABMS(m/z); 478(M+1)$^+$

Example 20

Compound 20 was dissolved To a solution of 38 mg (0.08 mmol) of Compound 19 in 4 ml of DMF was added 0.8 ml (7.63 mmol) of 50% aqueous dimethylamine, followed by stirring at 90° C. for 3 days. An aqueous saturated sodium hydrogencarbonate solution was added to the reaction mixture and extracted with CHCl$_3$. The extract was washed with brine, dried over Na$_2$SO$_4$, and evaporated. The residue was purified by silica gel column chromatography (CHCl$_3$/MeOH= 20/1) to give 20 mg (57%) of Compound 20.

$^1$HNMR(CDCl$_3$)∂; 2.33(s,6H), 2.74(t,2H,J=7.3 Hz), 3.15 (s,3H), 4.46(dt,2H,J=1.1,7.3 Hz), 7.41(ddd,1H,J=0.8,7.4,8.0 Hz), 7.46(s,1H), 7.48(dd,1H,J=0.8,8.2 Hz), 7.50(dd,1H,J= 1.3,7.4 Hz), 7.62(ddd,1H,J=1.3,7.4,8.4 Hz), 7.63(ddd,1H,J= 1.3,7.4,8.2 Hz), 7.73(dt, 1H,J=1.3,7.4 Hz), 8.22(dd,1H,J= 1.1,8.4 Hz), 9.10(ddd,1H,J=0.7,1.3,8.0 Hz).

FABMS(m/z); 443 (M+1)$^+$

Example 21

Compound 21

According to Example 5, 23 mg (86%) of a free base of Compound 21 was obtained from 29 mg (0.06 mmol) of Compound 20 and 15 mg of 10% Pd/C.

According to Example 13, 20 mg (91%) of Compound 21 was obtained from 19 mg (0.05 mmol) of the free base of Compound 21.

Free base $^1$HNMR(CDCl$_3$)∂; 2.32(s,6H), 2.73(t,2H,J=7.5 Hz), 3.19 (s,3H), 3.64(br s,2H), 4.45(t,2H,J=7.5 Hz), 6.86(dd,1H,J= 0.9,8.1 Hz), 6.91(dt,1H,J=0.9,7.5 Hz), 7.19(dd,1H,J=1.6,7.5 Hz), 7.28(ddd,1H,J=1.6,7.5,8.1 Hz), 7.40(ddd,1H,J=1.0,7.3, 8.1 Hz), 7.48(d,1H,J=8.2 Hz), 7.57(s,1H), 7.62(ddd,1H,J= 1.0,7.3,8.2 Hz), 9.12(dd,1H,J=1.0,8.1 Hz).

FABMS(m/z); 413(M+1)$^+$

Example 22

Compound 22

According to Example 2, 128 mg (48%) of Compound 22 was obtained from 200 mg (0.54 mmol) of Compound 10, 28 mg (0.70 mmol) of sodium hydride and 0.11 ml (1.08 mmol) of 1,3-dibromopropane.

$^1$HNMR(CDCl$_3$)∂; 2.45(m,2H), 3.15(s,3H), 3.40(m,1H), 4.57(t,1H,J=7.1 Hz), 4.88–5.32(m,2H), 7.07–7.84(m,7H), 8.22(m,1H), 9.11(d,1H,J=7.6 Hz).

FABMS(m/z); 492(M+1)$^+$

Example 23

Compound 23

According to Example 20, 104 mg (60%) of a free base of Compound 23 was obtained from 200 mg (0.41 mmol) of Compound 22 and 2 ml (33 mmol) of 28% aqueous ammonia.

According to Example 13, 88 mg (83%) of Compound 23 was obtained from 98 mg (0.23 mmol) of the free base of Compound 23.

Free base $^1$HNMR(CDCl$_3$)∂; 2.01(quint,2H,J=6.7 Hz), 2.75(t,2H,J= 6.7 Hz), 3.15(s,3H), 4.49(t,2H,J=6.7 Hz), 7.28–7.82(m,7H), 8.71(m,1H), 9.09(d,1H,J=7.8 Hz).

FABMS(m/z); 429(M+1)$^+$

Example 24

Compound 24

According to Example 20, 133 mg (72%) of a free base of Compound 24 was obtained from 200 mg (0.41 mmol) of Compound 22 and 2 ml (19.08 mmol) of 50% aqueous dimethylamine solution.

According to Example 13, 137 mg (100%) of Compound 24 was obtained from 126 mg (0.28 mmol) of the free base of Compound 24.

Free base $^1$HNMR(CDCl$_3$)∂; 1.86–2.36(m,4H), 2.17(s,6H), 3.15(s, 3H), 4.47(t,2H,J=6.2 Hz), 7.28–7.81(m,7H), 8.22(m,1H), 9.10(d,1H,J=7.6 Hz).

FABMS(m/z); 457(M+1)$^+$

Example 25

Compound 25

According to Example 5, 365 mg (89%) of a free base of Compound 25 was obtained from 440 mg (0.96 mmol) of a free base of Compound 24 and 120 mg of 10% Pd/C.

According to Example 13, 84 mg (90%) of Compound 25 was obtained from 80 mg (0.19 mmol) of the free base of Compound 25.

Free base $^1$HNMR(CDCl$_3$)∂; 1.79–2.38(m,4H), 2.19(s,6H), 3.18(s, 3H), 4.43(t,2H,J=6.4 Hz), 6.80–7.00(m,2H), 7.09–7.72(m, 6H), 9.10(dd,1H,J=1.1,7.7 Hz).

FABMS(m/z); 427(M+1)$^+$

Example 26

Compound 26

According to Example 6, 105 mg (98%) of a free base of Compound 26 was obtained from 100 mg (0.23 mmol) of a free base of Compound 25, 2.5 ml (29.1 mmol) of 35% formalin and 73 mg (1.18 mmol) of sodium cyanoborohydride.

According to Example 13, 90 mg (78%) of Compound 26 was obtained from 100 mg (0.22 mmol) of the free base of Compound 26.

Free base $^1$HNMR(CDCl$_3$)∂; 1.80–2.42(m,4H), 2.19(s,6H), 2.50(s, 6H), 3.19(s,3H), 4.43(t,2H,J=6.5 Hz), 6.98–7.72(m,7H), 7.66(s,1H), 9.12(d,1H,J=8.1 Hz).

FABMS(m/z); 455(M+1)$^+$

Example 27

Compound 27

According to Example 20, 137 mg (70%) of Compound 27 was obtained from 200 mg (0.41 mmol) of Compound 22 and 1.01 ml (9.76 mmol) of diethylamine.

$^1$HNMR(CDCl$_3$)∂; 0.93(t,6H,J=7.2 Hz), 2.03(quint,2H,J=6.8 Hz), 2.45 (t,2H,J=6.6 Hz), 2.49(q,4H,J=7.2 Hz), 3.15(s, 3H), 4.45(t,2H,J=7.0 Hz, 7.41(ddd,1H,J=1.0,7.4,7.9 Hz), 7.50(dd,1H,J=1.4,7.6 Hz), 7.53(d,1H,J=8.4Hz), 7.54(s,1H), 7.62(ddd,1H, 1.4,7.6,8.3 Hz), 7.63(ddd,1H,J=1.5,7.4,8.4 Hz), 7.73(dt,1H,J=1.4,7.6 Hz), 8.22(dd,1H,J=1.4,8.3 Hz), 9.11(dd,1H,J=1.5,7.9 Hz).

FABMS(m/z); 485(M+1)$^+$

Example 28

Compound 28

According to Example 5, 61 mg (274) of Compound 28 was obtained from 237 mg (0.49 mmol) of Compound 27 and 80 mg of 10% Pd/C.

HNMR(CDCl$_3$)∂; 0.96(t,6H,J=7.1 Hz), 2.02(m,2H), 2.46 (t,2H,J=6.7Hz), 2.50(q,4H,J=7.1 Hz), 3.19(s,3H), 3.60(s, 2H), 4.43(dt,2H,J=2.3,7.1 Hz), 6.85(dd,1H,J=1.2,8.0 Hz), 6.90(dt,1H,J=1.2,7.5 Hz), 7.18(dd,1H,J=1.6,7.5 Hz), 7.27 (ddd,1H,J=1.6,6.5,8.0 Hz), 7.40(ddd,1H,J=0.9,7.2,8.0 Hz), 7.52(d,1H,J=8.4 Hz), 7.60(s,1H, 7.62(ddd,1H,J=1.2,7.2,8.4 Hz), 9.12(ddd,1H,J=0.6,1.2,8.0 Hz).

FABMS(m/z); 455(M+1)$^+$

Example 29

Compound 29

According to Example 20, 115 mg (76%) of a free base of Compound 29 was obtained from 150 mg 0.31 mmol) of Compound 22 and 1.50 ml (17.0 mmol) of morpholine.

According to Example 13, 130 mg (100%) of Compound 29 was obtained from 117 mg (0.23 mmol) of the free base of Compound 29.

Free base $^1$HNMR(CDCl$_3$)∂; 2.05(quint,2H,J=6.3 Hz), 2.24(t,2H,J=6.3 Hz), 2.24–2.40(m,4H),3.14(s,3H),3.49–3.59 (m,4H), 4.48(m,2H),7.40(t,1H,J=7.6 Hz), 7.49–7.70(m,4H), 7.73(dt, 1H,J=1.2,7.5 Hz), 8.06(s,1H), 8.21(dd,1H,J=1.2,8.2 Hz), 9.09(d,1H,J=7.9 Hz).

FABMS(m/z); 499(M+1)$^+$

Example 30

Compound 30

According to Example 2, 515 mg (76%) of Compound 30 was obtained from 500 mg (1.35 mmol) of Compound 10, 75 mg (1.90 mmol) of sodium hydride and 0.64 ml (5.36 mmol) of 1,4-dibromobutane.

$^1$HNMR(CDCl$_3$)∂; 1.93(m,2H), 2.10(m,2H), 3.16(s,3H), 3.40(q,2H,J=5.9 Hz), 4.41(t,2H,J=7.2 Hz), 7.42(dt,1H,J=0.9,8.0 Hz), 7.44(s,1H), 7.48(d,1H,J=8.3 Hz), 7.51(dd,1H, J=1.4,7.6 Hz), 7.64(m,2H), 7.73(dt,1H,J=1.3,7.6 Hz), 8.22 (dd,1H,J=1.3,8.2 Hz), 9.12(dd,1H,J=0.7,8.0 Hz).

FABMS(m/z); 506(M+1)$^+$

Example 31

Compound 31

According to Example 20, 80 mg (76%) of a free base of Compound 31 was obtained from 120 mg (0.24 mmol) of Compound 30 and 1.5 ml (24.7 mmol) of 28% aqueous ammonia.

According to Example 13, 70 mg (84%) of Compound 31 was obtained from 76 mg (0.17 mmol) of the free base of Compound 31.

Free base $^1$HNMR(CDCl$_3$)∂; 1.53(m,2H), 1.96(m,2H), 2.72(t,2H,J=7.1 Hz), 3.15(s,3H), 4.39(t,2H,J=7.2 Hz), 7.42(dt,1H,J=1.0, 7.6 Hz), 7.44(s,1H), 7.48(d,1H,J=8.3 Hz), 7.51(dd,1H,J=1.5,7.7 Hz), 7.63(ddd,1H,J=1.2,7.6,8.3 Hz), 7.64(dt,1H,J=1.5,7.9 Hz), 7.73(dt,1H,J=1.3,7.8 Hz), 8.21(dd,1H,J=1.3,8.1 Hz), 9.11(d,1H,J=7.6 Hz).

FABMS(m/z); 443(M+1)$^+$

Example 32

Compound 32

According to Example 20, 100 mg (90%) of a free base of Compound 32 was obtained from 120 mg (0.24 mmol) of Compound 30 and 1.0 ml (9.54 mmol) of 50% aqueous dimethylamine solution.

According to Example 13, 70 mg (87%) of Compound 32 was obtained from 75 mg (0.16 mmol) of the free base of Compound 32.

Free base $^1$HNMR(CDCl$_3$)∂; 1.56(quint,2H,J=7.3 Hz), 1.74(quint, 2H,J=7.3 Hz), 2.16(s,6H),2.28(t,2H,J=7.3 Hz),3.15(s,3H), 4.39(t,2H, J=7.3 Hz), 7.40(dt, 1H,J=0.9,7.1 Hz), 7.46(s,1H), 7.48(d,1H,J=8.3 Hz), 7.50(dd,1H,J=1.5,7.6 Hz), 7.62(m, 1H), 7.63(m,1H), 7.73(dt, 1H,J=1.3,7.6 Hz), 8.22(dd,1H,J=1.3,8.2 Hz), 9.10(dd,1H,J=1.3,7.9 Hz).

FABMS(m/z); 471(M+1)$^+$

Example 33

Compound 33

According to Example 5, 30 mg (100%) of a free base of Compound 33 was obtained from 29 mg (0.06 mmol) of a free base of Compound 32 and 15 mg of 10% Pd/C.

According to Example 13, 24 mg (82%) of Compound 33 was obtained from 25 mg (0.06 mmol) of the free base of Compound 33.

Free base $^1$HNMR(CDCl$_3$)∂; 1.55(m,2H), 1.92(m,2H), 2.16(s,6H), 2.27(t,2H,J=7.4 Hz), 3.19(s,3H), 3.62(brs,2H), 4.37(t,2H,J=

7.5 Hz), 6.86(dd,1H,J=1.0,8.2 Hz), 6.91(dt,1H,J=1.0,7.6 Hz), 7.18(dd,1H,J=1.6,7.6 Hz), 7.28(ddd,1H,J=1.6,7.6,8.2 Hz), 7.40(dt,1H,J=1.0,7.5 Hz), 7.47(d,1H,J=8.3 Hz), 7.56(s, 1H), 7.62(ddd,1H,J=1.2,7.1,8.3 Hz), 9.12(d,1H,J=8.1 Hz).

FABMS(m/z); 441(M+1)$^+$

Example 34

Compound 34

According to Example 20, 98 mg (96%) of a free base of Compound 34 was obtained from 100 mg (0.20 mmol) of Compound 30 and 0.50 ml (5.74 mmol) of morpholine.

According to Example 13, 70 mg (87%) of Compound 34 was obtained from 75 mg (0.15 mmol) of the free base of Compound 34.

Free base $^1$HNMR(CDCl$_3$)∂; 1.58(m,2H), 1.95(m,2H), 2.34(m,6H), 3.15(s,3H), 3.62(t,4H,J=4.7 Hz), 4.39(t,2H,J=7.3 Hz), 7.41 (dt, 1H,J=0.8,7.9 Hz ), 7.44(s,1H), 7.48(d,1H,J=7.9 Hz), 7.50(dd,1H,J=1.5,7.6 Hz), 7.62(dt, 1H,J=1.2,7.9 Hz), 7.64 (m,1H), 7.73(dt,1H,J=1.3,7.6 Hz), 8.21(dd,1H,J=1.3,8.2 Hz), 9.11(d,1H,J=7.9 Hz).

FABMS(m/z); 513(M+1)$^+$

Example 35

Compound 35

To a solution of 140 mg (0.33 mmol) of a free base of Compound 25 in 23 ml of a mixed solvent of DMF and water (20/3) was added 1.28 ml (10.83 mmol) of bromoacetaldehyde dimethylacetal. The mixture was adjusted to pH 4 with 2N hydrobromic acid, and stirred at room temperature for 3 hours. To the reaction mixture was added 220 mg (3.55 mmol) of sodium cyanoborohydride, followed by stirring for 5 hours. An aqueous saturated sodium hydrogencarbonate solution was added to the reaction mixture, followed by extraction with CHCl$_3$. The extract was washed with brine, dried over Na$_2$SO$_4$, and evaporated. The residue was purified by silica gel column chromatography (CHCl$_3$/MeOH= 50/1) to give 63 mg (36%) of Compound 35.

$^1$HNMR(CDCl$_3$)∂; 2.03(quint,2H,J=6.7 Hz), 2.19(s,6H), 2.27(t,2H,J=6.7 Hz), 3.18(s,3H), 3.40–3.60(m,4H), 3.93(br s,1H), 4.44(m,2H), 6.79(dd,1H,J=0.9,8.3 Hz), 6.89(dt,1H,J= 0.9,7.5 Hz), 7.18(dd,1H,J=1.6,7.5 Hz), 7.36(ddd,1H,J=1.6, 7.5,8.3 Hz), 7.40(dt,1H,J=1.0,7.6 Hz), 7.55(d,1H,J=8.3 Hz), 7.62(s,1H), 7.62(ddd,1H,J=1.2,7.2,8.3 Hz), 9.13(d,1H,J=7.8 Hz).

FABMS(m/z); 533(M+1)$^+$

Example 36

Compound 36

According to Example 20, 16 mg (28%) of a free base of Compound 36 was obtained from 63 mg (0.12 mmol) of Compound 35 and 0.6 ml (5.72 mmol) of 50% aqueous dimethylamine solution.

According to Example 13, 21 mg (100%) of Compound 36 was obtained from 15 mg (0.03 mmol) of the free base of Compound 36.

Free base $^1$HNMR(CDCl$_3$)∂; 2.03(m,2H), 2.06(brs,6H), 2.20(s,1H), 2.27(t,2H,J=6.7 Hz), 2.35(m,1H), 2.42(m,1H), 3.16(m,2H), 3.17(s,3H),4.20(br,1H),4.44(m,2H),6.77(dd,1H,J=0.9,8.3 Hz), 6.83(dt,1H,J=0.9,7.4 Hz), 7.15(dd,1H,J=1.6,7.2 Hz), 7.35(ddd,1H,J=1.6,7.4,8.3 Hz), 7.40(ddd,1H,J=1.1,7.1,8.0 Hz), 7.55(d,1H,J=8.3 Hz), 7.59(s,1H), 7.62(ddd,1H, J=1.1, 7.1,8.3 Hz), 9.13(dd,1H,J=1.1,8.0 Hz).

FABMS(m/z); 498(M+1)$^+$

Example 37

Compound 37

According to Example 6, 48 mg (53%) of a free base of Compound 37 was obtained from 80 mg (0.23 mmol) of a free base of Compound 15, 54 mg (0.45 mmol) of glycolaldehyde dimer and 28 mg (0.45 mmol) of sodium cyanoborohydride.

According to Example 13, 64 mg (81%) of Compound 37 was obtained from 72 mg (0.18 mmol) of the free base of Compound 37.

Free base $^1$HNMR(CDCl$_3$)∂; 3.17(s,3H), 3.23(ddd,1H,J=3.7,7.9, 14.0 Hz), 3.43(ddd,1H,J=3.3,5.3,14.0 Hz), 3.58(m,1H), 3.88 (s,3H), 3.92(m,1H), 6.82(dd,1H,J=1.0,7.3 Hz), 6.85(dt,1H, J=1.1,7.4 Hz), 7.14(dd,1H,J=1.6,7.4Hz), 7.34(ddd,1H,J= 1.6,7.5,8.3 Hz), 7.40(ddd,1H,J=1.0,7.1,8.1 Hz), 7.45(d,1H, J=8.3 Hz), 7.48(s,1H), 7.63(ddd,1H,J=1.0,7.1,8.3 Hz), 9.07 (dd,1H,J=1.0,8.1 Hz).

FABMS(m/z); 400(M+1)$^+$

Example 38

Compound 38

According to Example 35, 278 mg (64%) of Compound 38 was obtained from 335 mg (0.94 mmol) of Compound 15, 4.5 ml (38.08 mmol) of bromoacetaldehyde dimethylacetal and 650 mg (10.48 mmol) of sodium cyanoborohydride.

$^1$HNMR(CDCl$_3$)∂; 3.18(s,3H), 3.43(m,2H), 3.56(m,2H), 3.91(s,3H), 3.96(m,1H), 6.80(dd,1H,J=0.8,8.3 Hz), 6.90(dt, 1H,J=0.8,7.5 Hz), 7.19(dd,1H,J=1.7,7.5 Hz), 7.36(dt,1H,J= 1.7,8.3 Hz), 7.42(dt,1H,J=0.8,8.0 Hz), 7.47(d,1H,J=8.3 Hz), 7.56(s,1H), 7.64(ddd,1H,J=1.2,7.2,8.3 Hz), 9.12(d,1H,J=8.0 Hz).

FABMS(m/z); 462(M+1)$^+$

Example 39

Compound 39

According to Example 20, 37 mg (24%) of a free base of Compound 39 was obtained from 180 mg (0.39 mmol) of Compound 38 and 4 ml (65.9 mmol) of 28% aqueous ammonia.

According to Example 13, 30 mg (78%) of Compound 39 was obtained from 33 mg (0.08 mmol) of the free base of Compound 39.

Free base $^1$HNMR(CDCl$_3$)∂; 1.21(brs,2H), 2.77(m,1H), 2.91(m, 1H), 3.15(s,3H), 3.20(m,2H), 3.85(s,3H), 4.01(m,1H), 6.81 (dd,1H,J=1.0,8.3 Hz), 6.83(dt,1H,J=1.0,7.5 Hz), 7.14(dd, 1H,J=1.6,7.3 Hz), 7.34(ddd,1H,J=1.6,7.5,8.3 Hz), 7.37(ddd, 1H,J=1.0,7.2,8.0 Hz), 7.41(d,1H,J=8.3 Hz), 7.50(s,1H), 7.60 (ddd,1H,J=1.2,7.2,8.3 Hz), 9.04(ddd,1H,J=0.7,1.2,8.0 Hz).

FABMS(m/z); 399(M+1)$^+$

Example 40

Compound 40

According to Example 20, 42 mg (50%) of a free base of Compound 40 was obtained from 91 mg (0.20 mmol) of Compound 38 and 2.0 ml (19.07 mmol) of 50% aqueous dimethylamine solution.

According to Example 13, 37 mg (85%) of Compound 40 was obtained from 37 mg (0.09 mmol) of the free base of Compound 40.

Free base $^1$HNMR(CDCl$_3$)∂; 2.08(s,6H), 2.34(m,1H), 2.45(m,1H), 3.17(t,2H,J=6.1 Hz), 3.19(s,3H), 3.90(s,3H), 4.27(br s,1H),

Example 41

Compound 41

According to Example 6, 68 mg (70%) of a free base of Compound 41 was obtained from 95 mg (0.22 mmol) of a free base of Compound 40, 4 ml (46.6 mmol) of 35% formalin and 220 mg (3.55 mmol) of sodium cyanoborohydride.

According to Example 13, 70 mg (91%) of Compound 41 was obtained from 63 mg (0.14 mmol) of the free base of Compound 41.
Free base
$^1$HNMR(CDCl$_3$)∂; 1.98(s,6H), 2.07(t,2H,J=7.5 Hz), 2.56 (s,3H), 2.88(m,2H), 3.18(s,3H), 3.89(s,3H), 7.11(dt,1H,J=1.1,7.4 Hz), 7.19(dd,1H,J=1.1,8.2 Hz), 7.29(dd,1H,J=1.7,7.4 Hz), 7.39(ddd,1H,J=1.7,7.4,8.2 Hz), 7.40(ddd,1H,J=0.9,7.3,7.9 Hz), 7.45(d,1H,J=8.4 Hz), 7.57(s,1H), 7.62(ddd,1H,J=1.0,7.3,8.4 Hz), 9.11(ddd,1H,J=0.8,1.0,7.9 Hz).

FABMS(m/z); 441(M+1)$^+$

Example 42

Compound 42

According to Example 20, 115 mg (62%) of a free base of Compound 42 was obtained from 189 mg (0.41 mmol) of Compound 38 and 0.85 ml (8.20 mmol) of diethylamine.

According to Example 13, 95 mg (91%) of Compound 42 was obtained from 90 mg (0.20 mmol) of the free base of Compound 42.
Free base
$^1$HNMR(CDCl$_3$)∂; 0.64(t,6H,J=7.1 Hz), 2.27(m,4H), 2.51(m,2H), 3.09 (m,2H), 3.17(s,3H), 3.89(s,3H), 4.32(m,1H), 6.76(dd,1H,J=1.0,8.2 Hz), 6.82(dt,1H,J=1.0,7.4 Hz), 7.15(dd,1H,J=1.6,7.4 Hz), 7.34(ddd,1H,J=1.6,7.4,8.2 Hz), 7.41(ddd,1H,J=0.9,7.2,8.0 Hz), 7.46(d,1H,J=8.3 Hz), 7.53 (s,1H), 7.63(ddd,1H,J=1.2,7.2,8.3 Hz), 9.12(ddd,1H,J=0.7,1.2,8.0 Hz).

FABMS(m/z); 455(M+1)$^+$

Example 43

Compound 43

According to Example 20, 52 mg (70%) of a free base of Compound 43 was obtained from 80 mg (0.17 mmol) of Compound 38 and 1.0 ml (11.48 mmol) of morpholine.

According to Example 13, 40 mg (78%) of Compound 43 was obtained from 45 mg (0.10 mmol) of the free base of Compound 43.
Free base
$^1$HNMR(CDCl$_3$)∂; 2.26(m,4H), 2.46(m,2H), 3.18(s,3H), 3.18(m,2H), 3.45(m,4H), 3.91(s,3H), 4.19(m,1H), 6.78(dd,1H,J=1.1,8.2 Hz), 6.84(dt, 1H,J=1.1,7.5 Hz), 7.13(dd,1H,J=1.6,7.5 Hz), 7.35(ddd,1H,J=1.6,7.5,8.2 Hz), 7.43(dt,1H,J=0.9,7.6 Hz), 7.48(d,1H,J=8.3 Hz), 7.51(s,1H), 7.65(ddd,1H, J=1.2,7.2,8.3 Hz), 9.13(d,1H,J=7.9 Hz).

FABMS(m/z); 469(M+1)$^+$

Example 44

Compound 44

To a solution of 1.50 g (4.22 mmol) of a free base of Compound 15 in 240 ml of a mixed solvent of dioxane and water (3/1) were added 1.77 g (21.07 mmol) of sodium hydrogencarbonate and 0.915 ml (6.41 mmol) of benzyloxycarbonyl chloride under an ice-cooled condition, followed by stirring for 1.5 hours. The reaction mixture was diluted with water, followed by extraction with CHCl$_3$. The extract was washed with brine, dried over Na$_2$SO$_4$, and evaporated. The residue was purified by silica gel column chromatography (CHCl$_3$/MeOH=100/1) to give 1.77 g (86%) of Compound 44.

$^1$HNMR(CDCl$_3$)∂; 3.14(s,3H), 3.84(s,3H), 5.04(s,2H), 6.51(s,1H), 7.18–7.24(m,5H), 7.26(dd,1H,J=1.1,7.5 Hz), 7.30(dd,1H,J=1.7,7.5 Hz), 7.40(ddd,1H,J=0.9,7.2,8.0 Hz), 7.42(s 1H), 7.44(d,1H,J=8.4 Hz), 7.48(dt,1H,J=1.7,7.5 Hz), 7.63(ddd,1H,J=1.2,7.2,8.4 Hz), 8.00(br s,1H), 9.07(ddd,1H, J=0.7,1.2,8.0 Hz).

FABMS(m/z); 490(M+1)$^+$

Example 45

Compound 45

To a suspension of 105 mg (2.63 mmol) of 60% sodium hydride in 5 ml of DMF was added a solution of 500 mg (1.02 mmol) of Compound 44 in 5 ml of DMF at room temperature, followed by stirring for 30 minutes. To the reaction mixture, 190 mg (1.32 mmol) of 2-dimethylaminoethyl chloride hydrochloride was added, followed by stirring at 90° C. for 1 hour. After evaporation of the solvent under reduced pressure, CHCl$_3$ was added to the residue. The solution was washed with brine, dried over Na$_2$SO$_4$, and evaporated. The residue was purified by silica gel column chromatography (CHCl$_3$/MeOH=50/1) to give 492 mg (86%) of Compound 45.

$^1$HNMR(CDCl$_3$)∂; 2.00–2.50(m,8H), 2.65–3.00(m,1H), 3.18(br s,3H), 3.39–3.52(m,4H), 4.98–5.34(m,2H), 6.95–7.67(m,13H), 9.10(m,1H).

FABMS(m/z); 561(M+1)$^+$

Example 46

Compound 46

According to Example 2, 169 mg (61%) of Compound 46 was obtained from 224 mg (0.46 mmol) of Compound 44, 24 mg (0.60 mmol) of sodium hydride and 0.19 ml (1.84 mmol) of 1,3-dibromopropane.

$^1$HNMR(CDCl$_3$)∂; 1.94(m,2H), 2.80–3.15(m,3H), 3.18(s, 3H), 3.43(m,1H), 3.52(br s,3H), 4.95–5.35(m,2H), 6.95–7.67(m,13H), 9.10(d,1H,J=7.8 Hz).

FABMS(m/z); 610(M+1)$^+$

Example 47

Compound 47

According to Example 20, 96 mg (62%) of Compound 47 was obtained from 169 mg (0.28 mmol) of Compound 46 and 0.48 ml (5.56 mmol) of 40% aqueous methylamine solution.

$^1$HNMR(CDCl$_3$)∂; 1.89(m,2H), 2.22–2.50(m,3H), 2.52–3.03(m,3H), 3.17(s,3H), 3.44(br s,3H), 3.55(m,1H), 3.93(m,1H), 6.80–7.70(m,13H), 1.87(d,1H,J=7.9 Hz).

FABMS(m/z); 561(M+1)$^+$

Example 48

Compound 48

According to Example 20, 93 mg (73%) of Compound 48 was obtained from 136 mg (0.22 mmol) of Compound 46 and 0.47 ml (4.40 mmol) of 50% aqueous dimethylamine solution.

---

(Page 41 continued top:)
6.80(dd,1H,J=0.9,8.2 Hz), 6.85(dt,1H,J=0.9,7.5 Hz), 7.17 (dd,1H,J=1.7,7.5Hz), 7.36(ddd,1H,J=1.7,7.6,8.2 Hz), 7.42 (m,1H), 7.47(d,1H,J=8.3 Hz), 7.53(s,1H), 7.64(ddd,1H,J=1.0,7.1,8.3 Hz), 9.12(dd,1H,J=1.0,7.8 Hz).

FABMS(m/z); 427(M+1)$^+$

¹HNMR (CDCl₃)∂; 1.58(m,2H), 2.07(m,8H), 2.64–2.98 (m,1H), 3.18(s,3H), 3.49(br s,4H), 5.00–5.36(m,2H), 6.90–7.67(m,13H), 9.09(br s,1H).

FABMS(m/z); 575(M+1)⁺

Example 49

Compound 49

According to Example 20, 105 mg (76%) of Compound 49 was obtained from 140 mg (0.23 mmol) of Compound 46 and 0.48 ml (4.64 mmol) of diethylamine.

¹HNMR (CDCl₃)∂; 0.87(br s,6H), 1.56(m,2H), 2.15–2.47 (m,6H), 2.63–2.93(m,1H), 3.18(s,3H), 3.42(br s,3H), 3.52 (m,1H), 5.00–5.34(m,2H), 6.95–7.68(m,13H), 9.10(br s,1H).

FABMS(m/z); 603(M+1)⁺

Example 50

Compound 50

According to Example 6, 85 mg (89%) of Compound 50 was obtained from 89 mg (0.16 mmol) of Compound 47, 0.023 ml (0.32 mmol) of propionaldehyde and 20 mg (0.32 mmol) of sodium cyanoborohydride.

¹HNMR (CDCl₃)∂; 0.78(br s,3H), 1.36(m,2H ), 1.61(m, 2H ), 1.97–2.40(m,7H), 2.62–2.95(m,1H), 3.18(s,3H), 3.44 (br s,3H), 3.51(m,1H), 5.00–5.35(m,2H), 6.93–7.68(m, 13H), 9.09(m,1H).

FABMS(m/z); 603(M+1)⁺

Example 51

Compound 51

According to Example 5, 57 mg (85%) of a free base of Compound 51 was obtained from 88 mg (0.15 mmol) of Compound 48 and 30 mg of 10% Pd/C.

According to Example 13, 60 mg (87%) of Compound 51 was obtained from 59 mg (0.13 mmol) of the free base of Compound 51.
Free base ¹HNMR(CDCl₃)∂; 1.63(m,2H), 1.78(br s,6H), 2.21(m, 2H), 3.18(s,3H), 3.19(m,2H), 3.90(s,3H), 4.71(br s,1H), 6.75(dd,1H,J=0.9,8.2 Hz), 6.80(dt,1H,J=0.9,7.4 Hz), 7.12 (dd,1H,J=1.6,7.4 Hz), 7.33(ddd,1H,J=1.6,7.4,8.2 Hz), 7.41 (ddd,1H,J=0.9,7.2,8.0 Hz), 7.46(d,1H,J=8.3Hz), 7.53(s,1H), 7.63(ddd,1H,J=1.1,7.2,8.3 Hz), 9.11(dd,1H,J=1.1,8.0 Hz).

FABMS(m/z); 441(M+1)⁺

Example 52

Compound 52

According to Example 5, 80 mg (100%) of a free base of Compound 52 was obtained from 100 mg (0.17 mmol) of Compound 49 and 30 mg of 10% Pd/C.

According to Example 13, 70 mg (88%) of Compound 52 was obtained from 69 mg (0.15 mmol) of the free base of Compound 52.
Free base ¹HNMR(CDCl₃)∂; 1.06(br s,6H), 1.84(m,1H), 1.92(m, 1H), 2.71(m,6H), 3.17(s,3H), 3.25(m,2H), 3.90(s,3H), 3.94 (m,1H), 6.84(dt,1H,J=0.9,7.4 Hz (dd,1H,J=1.6,7.4 Hz), 7.34 (ddd,1H,J=1.6,7.4,8.3 Hz), 7.40(ddd,1H,J=0.9,7.3,8.0 Hz), 7.46(d,1H,J=8.4 Hz), 7.49(s,1H), 7.63(ddd,1H,J=1.5,7.3,8.4 Hz), 7.76(dd,1H,J=0.9,8.3Hz), 9.09(dd,1H,J=1.5,8.0 Hz).

FABMS(m/z); 469(M+1)⁺

Example 53

Compound 53

According to Example 5, 54 mg (87%) of a free base of Compound 53 was obtained from 79 mg (0.13 mmol) of Compound 50 and 28 mg of 10% Pd/C.

According to Example 13, 55 mg (100%) of Compound 53 was obtained from 47 mg (0.10 mmol) of the free base of Compound 53.
Free base ¹HNMR(CDCl₃)∂; 0.57(t,3H,J=7.3 Hz), 1.00(m,2H), 1.64(m,2H), 1.84(br s,3H), 1.90(m,2H), 2.27(m,2H), 3.18 (s,3H), 3.18 (m,2H), 3.89(s,3H), 4.52(br s,1H), 6.76(dd,1H, J=0.8,8.3 Hz), 6.80(dt,1H,J=0.8,7.4 Hz), 7.13(dd,1H,J=1.6, 7.4 Hz), 7.33(ddd,1H,J=1.6,7.4,8.3 Hz), 7.41(dt,1H,J=0.9, 8.0 Hz), 7.46(d,1H,J=8.4 Hz), 7.54(s,1H), 7.63(ddd,1H,J= 1.5,7.2,8.4 Hz), 9.12(dd,1H,J=1.5, 8.0 Hz).

FABMS(m/z); 469(M+1)⁺

Example 54

Compound 54

To a solution of 500 mg (1.41 mmol) of Compound 15 in 20 ml of a mixed solvent of DMF and methylene chloride (1/1) were added 0.60 ml (4.30 mmol) of triethylamine and 0.27 ml (2.86 mmol) of acetic anhydride, followed by stirring at room temperature for 14 hours. Water was added to the reaction mixture, followed by extraction with CHCl₃. The extract was washed with brine, dried over Na₂SO₄, and evaporated. The residue was triturated with AcOEt to give 464 mg (83%) of Compound 54.

¹HNMR(DMSO-d₆)∂; 1.76(s,3H), 3.06(s,3H), 3.96(s, 3H), 7.25(t,1H,J=7.4 Hz), 7.35–7.45(m,3H), 7.66(ddd,1H, J=1.2,7.1,8.3 Hz), 7.71(s,1H), 7.75(d,2H,J=8.3 Hz), 8.86(s, 1H), 8.96(d,1H,J=7.8 Hz).

FABMS(m/z); 398(M+1)⁺

Example 55

Compound 55

According to Example 54, 290 mg (95%) of Compound 55 was obtained from 250 mg (0.70 mmol) of Compound 15, 0.15 ml (1.05 mmol) of triethylamine and 0.08 ml (1.05 mmol) of chloroacetyl chloride.

¹HNMR(CDCl₃)∂; 3.20(s,3H), 3.86(d,1H,J=15.4 Hz), 3.92(s,3H), 4.03(d,1H,J=15.4 Hz), 7.14–7.45(m,3H), 7.48 (d,1H,J=8.3 Hz), 7.48(s,1H), 7.53(dr,1H,J=1.7,7.7 Hz), 7.66 (ddd,1H,J=1.2,7.1,8.3 Hz), 8.03(d,1H,J=8.3 Hz), 8.45(br s,1H), 9.11(d,1H,J=8.3 Hz).

FABMS(m/z); 432(M+1)⁺

Example 56

Compound 56

According to Example 20, 89 mg (73%) of a free base of Compound 56 was obtained from 120 mg (0.28 mmol) of Compound 55 and 0.24 ml (2.80 mmol) of 50% aqueous dimethylamine solution.

According to Example 13, 87 mg (90%) of Compound 56 was obtained from 90 mg (0.20 mmol) of the free base of Compound 56.
Free base ¹HNMR(CDCl₃)∂; 1.90(s,6H), 2.72(d,1H,J=16.6 Hz), 2.93(d,1H,J=16.6 Hz), 3.20(s,3H), 3.90(s,3H), 7.30(dt, 1H,J=1.2,7.6 Hz), 7.39(ddd,1H,J=0.5,1.7,8.0 Hz), 7.44(ddd, 1H,J=0.8,7.2,8.1 Hz), 7.47(s,1H), 7.49(d,1H,J=8.4 Hz), 7.51 (dt, 1H,J=1.7,7.6 Hz), 7.67(ddd,1H,J=1.2,7.2,8.4 Hz), 8.21 (dd,1H,J=1.2,8.2 Hz), 9.12(ddd,1H,J=0.7,1.2,8.1 Hz), 9.28 (s,1H).

FABMS(m/z); 441(M+1)+

Example 57

Compound 57

According to Example 20, 121 mg (93%) of a free base of Compound 57 was obtained from 120 mg (0.28 mmol) of Compound 55 and 0.29 ml (2.80 mmol) of diethylamine.

According no Example 13, 81 mg (84%) of Compound 57 was obtained from 90 mg (0.19 mmol) of the free base of Compound 57.

Free base $^1$HNMR(CDCl$_3$)∂; 0.53(t,6H,J=7.1Hz), 2.18(q,4H,J=7.1 Hz), 2.83(d,1H,J=1.73 Hz), 2.99(d,1H,J=17.3 Hz), 3.19(s,3H), 3.91(s,3H), 7.25(dt,1H,J=17.6 Hz), 7.32(dd,1H,J=1.6, 7.6 Hz), 7.43(ddd,1H,J=0.8,7.3,8.0 Hz), 7.48(s,1H), 7.49 (dd,1H,J=0.8,8.4 Hz), 7.49 (ddd,1H,J=1.6,7.6,8.4 Hz), 7.66 (ddd,1H,J=1.2,7.3,8.4 Hz), 8.30(dd,1H,J=1.1,8.4 Hz), 9.12 (ddd,1H,J=0.7,2,8.0 Hz), 9.35(s,1H).

FABMS(m/z); 469(M+1)+

Example 58

Compound 58

According to Example 54, 235 mg (68%) of Compound 58 was obtained from 250 mg (0.70 mmol) of Compound 15, 0.15 ml (1.05 mmol) of triethylamine and 0.11 ml (1.05 mmol) of 3-bromopropionyl chloride.

$^1$HNMR(CDCl$_3$)∂; 2.82 (dd,1H,J=5.5,8.1 Hz), 2.90(m,1H), 3.05(s,3H), 3.57(m,1H), 3.66(m,1H), 3.81(s,3H), 7.24–7.38(m,1H), 7.45(s,1H), 7.47–7.62(m,5H), 7.87(br s,1H), 8.07(m,1H), 8.76(d,1H,J=7.9 Hz).

FABMS(m/z); 490(M+1)+

Example 59

Compound 59

According to Example 20, 108 mg (100%) of a free base of Compound 59 was obtained from 110 mg (0.22 mmol) of Compound 58 and 0.15 ml (2.25 mmol) of 50% aqueous dimethylamine solution.

According to Example 13, 80 mg (83%) of Compound 59 was obtained from 90 mg (0.20 mmol) of the free base of Compound 59.

Free base $^1$HNMR(CDCl$_3$)∂; 1.54(s,6H), 2.15(m,1H), 2.31(br s,3H), 3.19(s,3H), 3.92(s,3H), 7.22(m,1H), 7.24(d,1H,J=7.3 Hz), 7.43(ddd,1H,J=0.9,7.2,8.0 Hz), 7.47(m,1H), 7.49(dd,1H,J=0.9,8.3 Hz), 7.49(s,1H), 7.66(ddd,1H,J=1.2,7.2,8.3 Hz), 8.24(d,1H,J=8.2 Hz), 9.12(ddd,1H,J=0.7,1.2,8.0 Hz), 10.11(br s,1H).

FABMS(m/z); 455(M+1)+

Example 60

Compound 60

According to Example 20, 103 mg (96%) of a free base of Compound 60 was obtained from 110 mg (0.22 mmol) of Compound 58 and 0.46 ml (4.48 mmol) of diethylamine.

According to Example 13, 69 mg (72%) of Compound 60 was obtained from 90 mg (0.19 mmol) of the free base of Compound 60.

Free base $^1$HNMR(CDCl$_3$)∂; 0.61(t,6H,J=7.1 Hz), 2.08(m,4H), 2.18–2.40(m,3H), 2.53(m,1H), 3.18(s,3H), 3.89(s,3H), 7.27 (m,1H), 7.31(dd,1H,J=2.0,7.6 Hz), 7.42(ddd,1H,J=1.0,7.1,8.0 Hz), 7.47(m,1H), 7.48(d,1H,J=8.3 Hz), 7.52(s,1H), 7.65 (ddd,1H,J=1.2,7.1,8.3 Hz), 7.93(d,1H,J=8.2 Hz), 9.10(ddd, 1H,J=0.7,1.2,8.0 Hz), 9.91(br s,1H).

FABMS(m/z); 483(M+1)+

Example 61

Compound 61

To a solution of 160 mg (0.76 mmol) of Z-glycine in 6 ml of methylene chloride was added 158 mg (0.76 mmol) of N,N'-dicyclohexylcarbodiimide under an ice-cooled condition, followed by stirring for 50 minutes. To the reaction solution was added 200 mg (0.58 mmol) of Compound 11 in 4ml of THF, followed by stirring at room temperature for 2 hours. Ice was added to the reaction mixture, and the mixture was extracted with CHCl$_3$, washed successively with 2N hydrochloric acid, an aqueous saturated sodium hydrogencarbonate solution and brine, dried over MgSO$_4$, and evaporated. The residue was purified by silica gel column chromatography (CHCl$_3$/MeOH=30/1) to give 363 mg (100%) of Compound 61.

$^1$HNMR(DMSO-d$_6$)∂; 3.05(s,3H), 3.50(m,2H), 4.71(s, 2H), 7.00–7.98 (m,15H), 8.69(s,1H), 8.93(d,1H,J=6.8 Hz), 12.09(s,1H).

FABMS(m/z); 534(M+1)+

Example 62

Compound 62

According to Example 5, 204 mg (58%) of a free base of Compound 62 was obtained from 550 mg (1.03 mmol) of Compound 61 and 150 mg of 10% Pd/C.

According to Example 7, 74 mg (68%) of Compound 62 was obtained from 100 mg (0.25 mmol) of the free base of Compound 62.

Free base $^1$HNMR(DMSO-d$_6$)∂; 2.99(s,2H), 3.05(s,3H), 7.10–7.96 (m,8H), 8.26(d,1H,J=7.8 Hz), 8.91(d,1H,J=7.6 Hz), 12.00 (br s,1H).

FABMS(m/z); 399(M+1)+

Example 63

Compound 63

According to Example 61, 467 mg (100%) of Compound 63 was obtained from 250 mg (0.73 mmol) of Compound 11, 205 mg (0.95 mmol) of Boc-L-proline, 129 mg (0.95 mmol) of 1-hydroxybenzotriazole and 196 mg (0.95 mmol) of N,N'-dicyclohexylcarbodiimide.

$^1$HNMR(CDCl$_3$)∂; 0.80–2.00(m,5H), 3.00–3.70(m,2H), 3.18(s,3H), 4.02–4.40(m,2H), 6.80–7.68(m,12H), 8.04–8.55 (m,2H), 9.00(m,1H), 9.70 (m,1H).

FABMS(m/z); 539(M+1)+

Example 64

Compound 64

To a solution of 432 mg (0.80 mmol) of Compound 63 in 20 ml of methylene chloride was added 10 ml of trifluoroacetic acid under an ice-cooled condition, followed by stirring for 1 hour. After evaporation of the solvent under reduced pressure, an aqueous saturated sodium hydrogencarbonate solution was added to the residue, followed by extraction with CHCl$_3$. The extract was washed with brine, dried over Na$_2$SO$_4$, and evaporated. The residue was purified by silica gel column chromatography (CHCl$_3$/MeOH= 20/1) to give 213 mg (60%) of a base of Compound 64.

According to Example 7, 69 mg (80%) of Compound 64 was obtained from 79 mg (0.18 mmol) of the free base of Compound 64.

Free base

¹HNMR(DMSO-d6,90° C.)∂; 1.15–1.75(m,3H), 1.83(m, 1H), 1.95–2.30(m,1H), 2.50–2.80(m,1H), 3.08(s,3H), 3.47 (m,1H), 7.21(dt,1H,J=0.9,7.4 Hz), 7.36(m,2H), 7.43(ddd, 1H,J=1.5,7.3,8.1 Hz), 7.59 (m,2H), 7.65(d,1H,J=7.9 Hz), 8.22(m,1H), 8.95(dd,1H,J=1.0,8.1 Hz), 9.73(br s,1H), 11.89 (br,1H).

FABMS(m/z); 439(M+1)⁺

Example 65

Compound 65

To a suspension of 120 mg (0.34 mmol) of Compound 15 in 4 ml of 25% sulfuric acid was slowly added a solution of 30 mg (0.44 mmol) of sodium nitrite in 0.5 ml of water under an ice-cooled condition, followed by stirring for 20 minutes. To the reaction mixture was added a solution of 2.6 mg (0.04 mmol) of urea in 0.5 ml of water. The resulting mixture was added into 8 ml of boiling water, followed by stirring for 30 minutes. The reaction solution was extracted with CHCl₃, washed with water and then brine, dried over Na₂SO₄, and evaporated. The residue was purified by silica gel column chromatography (CHCl₃/MeOH=100/1) to give 105 mg (87%) of Compound 65.

¹HNMR(DMSO-d₆)∂; 3.05(s,3H), 3.97(s,3H), 6.90(dt, 1H,J=1.1,7.5 Hz), 6.93(dd,1H,J=1.1,8.2 Hz), 7.26(ddd,1H, J=1.8,7.5,8.2 Hz), 7.29(dd,1H,J=1.8,7.5 Hz), 7.38 (t,1H,J= 7.5 Hz), 7.65(ddd,1H,J=1.2,7.1,8.3 Hz), 7.73(d,1H,J=8.3 Hz), 7.77 (s,1H), 8.95 (d,1H,J=7.8 Hz), 9.38(s,1H) .

FABMS(m/z); 357(M+1)⁺

Example 66

Compound 66

To a solution of 90 mg (0.25 mmol) of Compound 65 in 4 ml of DMF were added 73 mg (0.51 mmol) of 2-dimethylaminoethyl chloride hydrochloride and 140 mg (1.01 mmol) of potassium carbonate, followed by stirring at 60° C. for 4.5 hours. An aqueous saturated sodium hydrogencarbonate solution was added to the reaction mixture, followed by extraction with CHCl₃. The extract was washed with brine, dried over Na₂SO₄, and evaporated. The residue was purified by silica gel column chromatography (CHCl₃/MeOH=20/1) to give 69 mg (64%) of a free base of Compound 66.

According to Example 13, 67 mg (92%) of Compound 66 was obtained from 67 mg (0.16 mmol) of the free base of Compound 66.

¹HNMR(DMSO-d₆)∂; 2.55(s,6H), 3.06(s,3H), 3.27(m, 2H), 3.99(s,3H), 4.32(m, 2H), 7.13(dt,1H,J=0.8,7.6 Hz), 7.40(dd,1H,J=0.8,8.2 Hz), 7.40(m,2H), 7.48(ddd,1H,J=1.8, 7.6,8.2 Hz), 7.67(ddd,1H,J=1.1,7.1,8.3 Hz), 7.76(d,1H,J= 8.3 Hz), 7.84(s,1H), 8.96(dd,1H,J=1.1,7.9 Hz).

FABMS(m/z); 428(M+1)⁺

Example 67

Compound 67

According to Example 66, 103 mg (47%) of a free base of Compound 67 was obtained from 173 mg (0.49 mmol) of Compound 65, 167 mg (0.97 mmol) of 2-diethylaminoethyl chloride hydrochloride and 268 mg (1.94 mmol) of potassium carbonate.

According to Example 13, 93 mg (95%) of Compound 67 was obtained from 90 mg (0.20 mmol) of the free base of Compound 67.

¹HNMR(DMSO-d₆)∂; 0.83(m,6H), 2.88(m,4H), 3.07(s, 3H), 3.28(m,2H), 3.99(s,3H), 4.31(m,2H), 7.14(dt, 1H,J= 1.0,7.6 Hz), 7.18(d,1H,J=8.2Hz), 7.40(m,2H), 7.48(ddd,1H, J=1.7,7.6,8.2 Hz), 7.67(ddd,1H,J=1.2,7.1,8.3 Hz), 7.76(d, 1H,J=8.3 Hz), 7.84(s,1H), 8.96(ddd,1H,J=0.7,1.2,7.5 Hz), 9.56(br s,1H).

FABMS(m/z); 455(M)⁺

Example 68

Compound 68

To a suspension of 681 mg (5.11 mmol) of aluminum chloride in 5 ml of methylene chloride had been suspended was added 365 ml (5.13 mmol) of acetyl chloride under an ice-cooled condition, followed by stirring for 30 minutes. After cooling the mixture to −78° C., a solution of 500 mg (1.02 mmol) of Compound 44 dissolved in 5 ml of methylene chloride was added thereto, followed by stirring for 20 minutes. Water was added to the reaction mixture, followed by extraction with CHCl₃. The extract was washed with brine, dried over Na₂SO₄, and evaporated. The residue was purified by silica gel column chromatography (CHCl₃/MeOH=100/1) to give 564 mg (100%) of Compound 68.

¹HNMR(DMSO-d6)∂; 2.65(s,3H), 2.98(s,3H), 3.86(s, 3H), 4.89(s,2H), 7.02–7.10(m,5H), 7.20(dt,1H,J=1.2,7.6 Hz), 7.32(dd,1H,J=1.5,7.6 Hz), 7.39(dt,1H,J=1.5,7.7 Hz), 7.58(d,1H,J=8.1Hz), 7.71(s,1H), 7.75(d,1H,J= 8.8Hz), 8.19 (dd,1H,J=1.1,8.8 Hz), 8.63(s,1H), 9.53(br s,1H).

FABMS(m/z); 532(M+1)⁺

Example 69

Compound 69

To a solution of 554 mg (1.02 mmol) of Compound 68 in 5 ml of methylene chloride were added 343 mg (4.08 mmol) of sodium hydrogencarbonate and 800 mg (2.55 mmol) of 55% m-chloroperbenzoic acid, followed by stirring at room temperature for 10 hours. An aqueous saturated sodium nitrite solution was added to the reaction mixture, followed by extraction with CHCl₃. The extract was washed with brine, dried over Na₂SO₄, and evaporated. The residue was purified by silica gel column chromatography (CHCl₃/MeOH=100/1) to give 604 mg (100%) of Compound 69.

¹HNMR(DMSO-d₆)∂; 2.37(s,3H), 3.01(s,3H), 3.91(s, 3H), 4.94(s,2H), 7.07–7.17(m,5H), 7.25(dt, 1H,J=1.2,7.3 Hz), 7.37(dd,1H,J=1.6,7.6 Hz), 7.44(m,1H), 7.45(dd,1H,J= 2.2,8.9 Hz), 7.63(d,1H,J=8.0 Hz), 7.72(s,1H), 7.76(d,1H,J= 8.9 Hz), 8.64(d,1H,J=2.2 Hz), 8.67(s,1H).

FABMS (m/z); 548(M+1)⁺

Example 70

Compound 70

To a solution of 603 mg (1.02 mmol) of Compound 69 in 100 ml of a mixed solution of THF and MeOH containing 10% of water (1/1) was added 282 mg (2.04 mmol) of potassium carbonate, followed by stirring at room temperature for 1 hour. To the reaction mixture, 1N hydrochloric acid was added, followed by extraction with CHCl₃, washed with brine, dried over Na₂SO₄, and evaporated. The residue was purified by silica gel column chromatography (CHCl₃/MeOH=50/1) to give 423 mg (73%) of Compound 70.

¹HNMR(DMSO-d₆)∂3.01(s,3H), 3.83(s,3H), 4.96(s,2H), 7.10–7.20(m,6H), 7.24(dt,1H,J=1.2,7.6 Hz), 7.35(dd,1H,J= 1.7,7.6 Hz), 7.43(ddd,1H,J=1.7,7.6,8.1 Hz), 7.54(d,1H,J= 8.8 Hz), 7.60(s,1H), 7.63(d,1H,J=8.1 Hz), 8.40(d,1H,J=2.4 Hz), 8.61(s,1H), 9.33(s,1H).

FABMS(m/z); 505(M)⁺

Example 71

Compound 71

According to Example 66, 364 mg (89%) of Compound 71 was obtained from 348 mg (0.69 mmol) of Compound 70, 0.10 ml 0.84 mmol) of benzyl bromide and 190 mg (1.38 mmol) of potassium carbonate.

$^1$HNMR(DMSO-d$_6$)∂3.02(s,3H), 3.85(s,3H), 4.95(s,2H), 5.25(s,2H), 7.08–7.18(m,5H), 7.24(dt,1H,J=1.2,7.5 Hz), 7.32–7.47(m,6H), 7.57(m,2H), 7.64(s,1H), 7.64(m,2H), 8.62(d,1H,J=2.4 Hz), 8.63(s,1H).

FABMS(m/z); 596(M+1)$^+$

Example 72

Compound 72

According to Example 45, 281 mg (84%) of Compound 72 was obtained from 300 mg (0.50 mmol) of Compound 71, 52 mg (1.30 mmol) of sodium hydride and 94 mg (0.65 mmol) of 2-dimethylaminoethyl chloride hydrochloride.

$^1$HNMR(DMSO-d$_6$)∂; 2.02(s,6H), 2.25(t,2H), 3.02(m, 2H), 3.05(s,3H), 3.07(s,3H), 5.03(brs,2H), 5.27(s,2H), 7.04–7.22(m,5H), 7.30–7.44(m,8H), 7.50(ddd,1H,J=1.7,6.8, 8.5 Hz), 7.56(m,2H), 7.62(d,1H,J=8.8 Hz), 8.66(d,1H,J=2.4 Hz).

FABMS(m/z); 667(M+1)$^+$

Example 73

Compound 73

According to Example 5, 155 mg (90%) of a free base of Compound 73 was obtained from 260 mg (0.39 mmol) of Compound 72 and 10% Pd/C.

According to Example 13, 162 mg (88%) of Compound 73 was obtained from 159 mg (0.36 mmol) of the free base of Compound 73.

Free base $^1$HNMR(CDCl$_3$)∂; 2.23(s,6H), 2.80(t,2H,J=5.1 Hz), 3.02 (s,3H), 3.39(s,3H), 3.61(m,2H), 4.67(brs,1H), 6.78(dt,1H,J= 1.0,7.5 Hz), 6.87(m,2H), 6.95(dd,1H,J=1.6,7.5 Hz), 6.96(dd, 1H,J=2.3,8.7 Hz), 7.22(s,1H), 7.35(ddd,1H,J=1.6,7.5,8.1 Hz), 7.51(d,1H,J=2.3Hz).

FABMS(m/z); 443(M+1)$^+$

Example 74

Compound 74 and Compound 75

To a solution of 0.08 ml (0.86 mmol) of trifluoromethanesulfonic acid in 15 ml of methylene chloride was added 0.04 ml (0.85 mmol) of fuming nitric acid under an ice-cooled condition. After cooling the mixture to –78° C., a solution of 320 mg (0.57 mmol) of Compound 45 in 5 ml of methylene chloride was added thereto, followed by stirring at room temperature for 16 hours. An aqueous saturated sodium hydrogencarbonate solution was added to the reaction mixture, followed by extraction with CHCl$_3$. The extract was washed with brine, dried over Na$_2$SO$_4$, and evaporated. The residue was purified by silica gel column chromatography (CHCl$_3$/MeOH=20/1) to give 320 mg (90%) of Compound 74 and 36 mg (10%) of Compound 75.

Compound 74

$^1$HNMR(DMSO-d6,90° C.)∂; 2.02(s,6H), 2.27(br t,2H), 3.00(m,2H), 3.06(s,3H), 3.81(s,3H), 5.00(s,2H), 7.03–7.17 (m,5H), 7.41(m,1H), 7.45(m,2H), 7.52(ddd,1H,J=2.0,6.8, 8.0 Hz), 7.65(s,1H), 7.89(d,1H,J=9.4 Hz), 8.50(dd,1H,J= 2.5,9.4 Hz), 9.88(d,1H,J=2.5 Hz).

FABMS(m/z); 606(M+1)$^+$

Compound 75

$^1$HNMR (DMSO-d6,90° C.)∂; 2.02(s,6H), 2.27(br t,2H), 3.00(m,2H), 3.05(s,3H), 3.65(s,3H), 4.99(s,2H), 7.03–7.17 (m,5H), 7.40(m,1H), 7.44(m,2H), 7.52(ddd,1H,J=2.0,6.9, 7.9 Hz), 7.56(t,1H,J=7.9 Hz), 7.67(s,1H), 8.20(dd,1H,J=1.1, 7.9 Hz), 9.38(dd,1H,J=1.1,7.9 Hz).

FABMS (m/z); 606(M+1)$^+$

Example 75

Compound 76 and Compound 77

To a solution of 324 mg (0.54 mmol) of a mixture of Compound 74 and Compound 75 in 15 ml of methylene chloride were added 0.12 ml (1.07 mmol) of anisole and 0.47 ml (5.34 mmol) of trifluoromethanesulfonic acid, followed by stirring at room temperature for 40 minutes. An aqueous saturated sodium hydrogencarbonate solution was added to the reaction mixture, followed by extraction with CHCl$_3$. The extract was washed with brine, dried over Na$_2$SO$_4$, and evaporated. The residue was purified by silica gel column chromatography (CHCl$_3$/MeOH=50/1) to give 196 mg (78%) of a free base of Compound 76 and 20 mg (8%) of a free base of Compound 77.

According to Example 13, 69 mg (85%) of Compound 76 was obtained from 70 mg (0.15 mmol) of the free base of Compound 76, and 22 mg (93%) of Compound 77 was obtained from 20 mg (0.04 mmol) of the free base of Compound 77.

Free base of Compound 76

$^1$HNMR(CDCl$_3$)∂; 2.31(s,6H), 2.70(m,2H), 3.19(s,3H), 3.33(m,2H), 3.97 (s,3H), 6.76(d,1H,J=8.2 Hz), 6.87(dt1H, J=1.0,7.4 Hz), 7.14(dd,1H,J=1.6,7.4 Hz), 7.37(ddd,1H,J= 1.6,7.4,8.2 Hz), 7.48(d,1H,J=9.1 Hz), 7.61 (s,1H), 8.48(dd, 1H,J=2.2,9.1 Hz), 9.92(d,1H,J=2.2 Hz).

FABMS(m/z); 472(M+1)$^+$

Free base of Compound 77

$^1$HNMR(CDCl$_3$)∂; 2.07(s,6H), 2.36(m,1H), 2.44(m,1H), 3.16(t,2H,J=5.9 Hz), 3.19(s,3H), 3.90(s,3H), 4.25(br s,1H), 6.79(dd,1H,J=0.9,8.2 Hz), 6.84(dt,1H,J=0.9,7.5 Hz), 7.14 (dd,1H,J=1.6,7.5 Hz), 7.36(ddd,1H, J=1.6, 7.5,8.2 Hz), 7.44 (t,1H,J=7.9 Hz), 7.68(s,1H), 8.11(dd,1H, J=1.2,7.9 Hz), 9.49 (dd,1H, J=1.2,7.9 Hz).

FABMS(m/z); 472(M+1)$^+$

Example 76

Compound 78 and Compound 79

To a solution of 500 mg (1.17 mmol) of a free base of Compound 40 in 40 ml of methylene chloride was added 0.300 ml (7.10 mmol) of fuming nitric acid in three portions at 30 minutes intervals, followed by stirring at room temperature for 1.5 hours. An aqueous saturated sodium hydrogencarbonate solution was added to the reaction mixture, followed by extraction with CHCl$_3$. The extract was washed with brine, dried over Na$_2$SO$_4$, and evaporated. The residue was purified by silica gel column chromatography (CHCl$_3$/MeOH=100/1) to give 74 mg (13%) of a free base of Compound 78 and 293 mg (53%) of a free base of Compound 79.

According to Example 13, 49 mg (76%) of Compound 78 was obtained from 56 mg (0.12 mmol) of the free base of Compound 78, and 66 mg (95%) of Compound 79 was obtained from 60 mg (0.13 mmol) of the free base of Compound 79.

Free base of Compound 78

$^1$HNMR(CDCl$_3$)∂; 2.03(s,6H), 2.16(m,2H), 2.55(m,2H), 3.21(s,3H), 3.92(s,3H), 6.83(dd,1H,J=7.3,8.5 Hz), 7.41(dd, 1H, J=1.7,7.3 Hz), 7.43(ddd,1H, J=1.0,7.2,7.9 Hz), 7.49(d, 1H,J=8.3 Hz), 7.55(s,1H), 7.66(ddd,1H,J=1.2,7.2,8.3 Hz), 7.91(br t,1H), 8.22(dd,1H,J=1.7,8.5 Hz), 9.12(d,1H,J=7.9 Hz).

FABMS(m/z); 472 (M+1)$^+$

Free base of Compound 79

$^1$HNMR(CDCl$_3$)∂; 2.04(s,6H), 2.38(m,1H), 2.45(m,1H), 3.18(s,3H), 3.23(m,2H), 3.95(s,3H), 5.28(br s,1H), 6.67(d, 1H, J=9.2 Hz), 7.44(dt,1H, J=0.8,7.9 Hz), 7.51(d,1H, J=8.3 Hz), 7.51(s,1H), 7.67(ddd,1H, J=1.3,7.9, 8.3 Hz), 8.12(d, 1H, J=2.7 Hz), 8.27(dd,1H,J=2.7,9.2 Hz), 9.12(d,1H, J=7.9 Hz).

FABMS(m/z); 472 (M+1)$^+$

Example 77

Compound 80

To a solution of 0.004 ml (0.05 mmol) of trifluoromethanesulfonic acid in 0.2 ml of methylene chloride was added 0.002 ml (0.05 mmol) of fuming nitric acid under an in ice-cooled condition, followed by stirring for 0.5 hours. After cooling the mixture to −78° C., 10 mg (0.02 mmol) of a free base of Compound 40 in 0.2 ml of methylene chloride was added thereto, followed by stirring at room temperature for 18 hours. An aqueous saturated sodium hydrogencarbonate solution was added to the reaction mixture, followed by extraction with CHCl$_3$. The extract was washed with brine, dried over Na$_2$SO$_4$, and evaporated. The residue was purified by preparatory thin-layer chromatography (CHCl$_3$/MeOH=10/1) to give 3 mg (26%) of Compound 80.

$^1$HNMR(CDCl$_3$)∂; 2.11(s,6H), 2.26(m,1H), 2.61(m,1H), 3.23(m,2H), 3.24 (s,3H), 4.05(s,3H), 7.58(d,1H,J=9.1 Hz), 7.65(s,1H), 8.19(dd,1H,J=0.4,2.7 Hz), 8.58(dd,1H,J=2.2,9.1 Hz), 9.18(d,1H,J=2.7 Hz), 9.99(d,1H, J=2.2 Hz).

FABMS(m/z); 562(M+1)$^+$

Example 78

Compound 81

According to Example 74, 53 mg of a crude nitro compound was obtained from 40 mg (0.07 mmol) of Compound 45, 0.032 ml (0.36 mmol) of trifluoromethanesulfonic acid and 0.015 ml (0.035 mmol) of fuming nitric acid. Then, according to Example 5, 5 mg (17%) of Compound 81 was obtained from 30 mg of 10% Pd/C.

$^1$HNMR(CDCl$_3$)∂; 1.58(m,2H), 2.07(s,6H), 2.35(m,1H), 2.43(m,1H), 3.15(m,2H), 3.15(s,3H), 3.83(s,3H), 4.24(br s,1H), 6.77(d,1H,J=8.2 Hz), 6.83(dt,1H,J=1.0,7.5 Hz), 7.06 (dd,1H,J=2.4,8.5 Hz), 7.14(dd,1H,J=1.7, 7.5 Hz), 7.27(d, 1H,J=8.5 Hz), 7.34(ddd,1H,J=1.7,7.5,8.2 Hz), 7.43(s,1H), 8.46(d,1H,J=2.4 Hz).

FABMS(m/z); 442(M+1)$^+$

Example 79

Compound 82

To a solution of 80 mg (0.19 mmol) of a free base of Compound 40 in 3 ml of CHCl$_3$ was added 118 mg (0.25 mmol) of tetra-n-butylammonium tribromide, followed by stirring at room temperature for 1.5 hours. An aqueous saturated sodium nitrite solution was added to the reaction mixture, followed by extraction with CHCl$_3$. The extract was washed with an aqueous saturated sodium hydrogencarbonate solution and then brine, dried over Na$_2$SO$_4$, and evaporated. The residue was purified by silica gel column chromatography (CHCl$_3$/MeOH=20/1) to give 67 mg (71%) of a free base of Compound 82.

According to Example 13, 69 mg (90%) of Compound 82 was obtained from 67 mg (0.13 mmol) of the free base of Compound 82.

Free base $^1$HNMR(CDCl$_3$)∂; 2.04(s,6H), 2.32(m,1H), 2.42(m,1H), 3.10(t,2H,J=6.1 Hz), 3.18(s,3H), 3.91(s,3H), 4.30(m,1H), 6.63(d,1H,J=8.8 Hz), 7.26(d,1H,J= 2.7 Hz), 7.41(dd,1H,J= 2.7,8.8 Hz), 7.42(ddd,1H,J=1.7,7.3,8.1 Hz), 7.47(s,1H), 7.48(d,1H,J=8.5 Hz), 7.65(ddd,1H,J=1.2,7.3,8.5 Hz), 9.11 (ddd,1H,J=0.7,1.2,8.1 Hz).

FABMS(m/z); 505(M+1)$^+$

Example 80

Compound 83

To a solution of 70 mg (0.16 mmol) of a free base of Compound 40 in 5 ml of a mixed solvent of methylene chloride and MeOH (7/3) was added 261 mg (0.54 mmol) of tetra-n-butylammonium tribromide, followed by stirring at room temperature for 13 hours. An aqueous saturated sodium nitrite solution was added to the reaction mixture, followed by extraction with CHCl$_3$. The extract was washed with an aqueous saturated sodium hydrogencarbonate solution and then brine, dried over Na$_2$SO$_4$, and evaporated. The residue was purified by silica gel column chromatography (CHCl$_3$/MeOH=100/1) to give 92 mg (84%) of a free base of Compound 83.

According no Example 13, 70 mg (78%) of Compound 83 was obtained from 80 mg (0.12 mmol) of the free base of Compound 83.

Free base $^1$HNMR(CDCl$_3$)∂; 2.02(s,6H), 2.15(t,2H,J=5.9 Hz), 2.48 (m,1H), 2.55(m,1H), 3.21(s,3H), 3.89(s,3H), 4.76(m,1H), 7.28(dd,1H,J=0.8,2.3 Hz), 7.35 (d,1H,J=8.7 Hz), 7.55(s, 1H), 7.69(d,1H,J=2.3 Hz), 7.72(dd,1H, J=2.0, 8.7 Hz), 9.25 (d,1H,J=2.0 Hz).

FABMS(m/z); 661(M+1)$^+$

Example 81

Compound 84

According to Example 68, 15 mg (82%) of Compound 84 was obtained from 16 mg (0.04 mmol) of Compound 54, 54 mg (0.41 mmol of aluminum chloride and 0.03 ml (0.42 mmol) of acetyl chloride.

$^1$HNMR(DMSO-d$_6$)∂; 1.76(s,3H), 2.72(s,3H), 3.08(s, 3H), 4.00(s,3H), 7.26 (t,1H,J=7.4 Hz), 7.39(dd,1H,J=1.0,7.4 Hz), 7.43(m,1H), 7.75(d,1H,J=7.8 Hz), 7.79(s,1H), 7.83(d, 1H, J=8.8 Hz), 8.26(dd,1H,J=1.9, 8.8 Hz), 8.89(s,1H), 9.61 (d,1H,J=1.9 Hz).

FABMS(m/z); 440(M+1)$^+$

Example 82

Compound 85

According to Example 68, 73 mg (61%) of Compound 85 was obtained from 100 mg (0.25 mmol) of Compound 54, 268 mg (2.01 mmol) of aluminum chloride and 0.08 ml (1.00 mmol) of chloroacetyl chloride.

$^1$HNMR(DMSO-d$_6$)∂; 1.76(s,3H), 3.08(s,3H), 4.01(s, 3H), 5.26(s,2H), 7.26 (t,1H,J=7.6 Hz), 7.39(d,1H,J=7.6 Hz), 7.43(t,1H,J=7.6 Hz), 7.75(d,1H,J=7.8 Hz), 7.81(s,1H), 7.86 (d,1H,J=8.8 Hz), 8.28(dd,1H,J=1.7,8.8 Hz), 8.89(s,1H), 9.60(d,1H,J=1.7 Hz).

FABMS(m/z); 474(M+1)$^+$

Example 83

Compound 86

According to Example 74, 5 mg (48%) of Compound 86 was obtained from 10 mg (0.03 mmol) of Compound 54, 0.005 ml (0.05 mmol) of trifluoromethanesulfonic acid and 0.002 ml (0.05 mmol) of fuming nitric acid.

$^1$HNMR(DMSO-d$_6$)∂; 1.76(s,3H), 3.09(s,3H), 4.04(s, 3H), 7.27(t,1H,J=7.4 Hz), 7.40(d,1H,J=7.8 Hz), 7.44(t,1H, J=7.6 Hz), 7.74(d,1H,J=8.1 Hz), 7.88(s,1H), 7.94(d,1H,J= 9.3 Hz), 8.51(dd,1H,J=2.4,9.3 Hz), 8.94(s,1H), 9.79(d,1H, J=2.4 Hz).

FABMS(m/z); 443(M+1)$^+$

Example 84

Compound 87

To a solution of 10 mg (0.03 mmol) of Compound 54 in 2 ml of CHCl$_3$ was added 0.068 ml (2.04 mmol) of fuming nitric acid in 5 portions at 1 to 4 hours intervals, followed by stirring at room temperature for 11 hours. An aqueous saturated sodium hydrogencarbonate solution was added to the reaction mixture, followed by extraction with CHCl$_3$. The extract was washed with brine, dried over Na$_2$SO$_4$, and evaporated. The residue was purified by preparatory thin-layer chromatography (CHCl$_3$/MeOH=50/1) to give 4 mg (32%) of Compound 87.

$^1$HNMR (DMSO-d$_6$)∂; 1.70(s,3H), 3.12(s,3H), 3.96(s, 3H), 7.60(t,1H,J=7.8 Hz), 7.79(dd,1H,J=1.5,7.6 Hz), 8.05 (dd,1H,J=1.5, 8.1 Hz), 8.07(s,1H), 9.02(d,1H,J=2.3 Hz), 9.57(s,1H), 10.12(d,1H,J=2.3 Hz).

FABMS(m/z); 533(M+1)$^+$

Example 85

Compound 88

According to Example 54, 280 mg (88%) of Compound 88 was obtained from 293 mg (0.62 mmol) of a free base of Compound 79, 0.26 ml (1.87 mmol) of triethylamine and 0.09 ml (0.93 mmol) of acetyl chloride.

$^1$HNMR (CDCl$_3$)∂;2.10(m,2H), 2.10(s,6H), 2.17(s,3H), 2.15(m,1H), 2.34 (m,1H), 3.19(s,3H), 3.96(s,3H), 7.45(dd, 1H,J=7.1,8.0 Hz), 7.48(d,1H, J=8.1 Hz), 7.51(s,1H), 7.68 (m,2H), 8.36(dd,1H,J=2.4,8.5 Hz), 8.38(d,1H, J=2.4 Hz), 9.12(d,1H,J=8.0 Hz).

FABMS(m/z); 514(M+1)$^+$

Example 86

Compound 89 and Compound 90

According to Example 74, 155 mg (71%) of Compound 89 and 38 mg (17%) of Compound 90 were obtained from 200 mg (0.39 mmol) of Compound 88, 0.051 ml (0.58 mmol) of trifluoromethanesulfonic acid and 0.025 ml (0.58 mmol) of fuming nitric acid.

Compound 89

$^1$HNMR (CDCl$_3$)∂; 2.13(br s,6H), 1.90–2.50(m,5H), 2.85–3.05(m, 1H), 3.22(s, 3H), 3.95(m,1H), 3.97(s,3H), 7.55(d,1H,J=9.0 Hz), 7.55(s,1H), 7.71(m,1H), 8.38(m,2H), 8 .57(dd,1H,J=2.2,9.0 Hz), 9.98(d,1H,J=2.2 Hz).

FABMS(m/z); 559(M+1)$^+$

Compound 90

$^1$HNMR (CDCl$_3$)∂; 1.78(br s,3H), 1.90–2.40(m,4H), 2.12 (br s,6H), 3.21(s, 3H), 3.89(s,3H), 7.49(t,1H,J=7.9 Hz), 7.50(m,1H), 7.72(d,1H,J=8.6 Hz), 8.17(d,1H,J=7.9 Hz), 8.37(d,1H,J=2.5 Hz), 8.39(dd,1H,J=2.5,8.6 Hz), 9.49(dd, 1H,J=1.2,7.9 Hz).

FABMS(m/z); 559(M+1)$^+$

Example 87

Compound 91

According to Example 5, 138 mg (100%) of Compound 91 was obtained from 150 mg (0.27 mmol) of Compound 89 and 70 mg of 10% Pd/C.

$^1$HNMR(CDCl$_3$)∂; 1.39(m,1H), 2.03(m,3H), 1.19(br s,6H), 2.40(m,2H), 3.05(m, 1H), 3.16(s,3H), 3.81(br s,4H), 3.83(br s,3H), 6.73(d,1H,J=2.7 Hz), 6.76(dd,1H,J=2.7,8.3 Hz), 7.06(dd,1H,J=2.4,8.5 Hz), 7.13(m,1H), 7.20(m,1H), 7.27(d,1H,J=8.5 Hz), 8.43(dd,1H,J=0.4,2.4 Hz).

FABMS(m/z); 499(M+1)$^+$

Example 88

Compound 92

To a solution of 73 mg (0.25 mmol) of triphosgene and 0.10 ml (0.74 mmol) of triethylamine in 7 ml of o-dichlorobenzene was added a solution of 200 mg (0.56 mmol) of Compound 15 in 10 ml of o-dichlorobenzene at room temperature, followed by stirring at 80° C. for 2.5 hours. After evaporation of the solvent under reduced pressure, the residue was dissolved in 15 ml of 1,2-dichloroethane, and 300 mg (2.25 mmol) of aluminum chloride was added thereto at room temperature, followed by stirring at 80° C. for 3 hours. Ice and 2N hydrochloric acid were added to the reaction mixture, followed by extraction with CHCl$_3$. The extract was washed with brine, dried over Na$_2$SO$_4$, and evaporated. The residue was triturated with CHCl$_3$ to give 117 mg (55%) of Compound 92.

$^1$HNMR(DMSO-d$_6$)∂; 3.18(s,3H), 4.00(s,3H), 7.24(ddd, 1H,J=1.5,7.3,8.4 Hz), 7.39(dd,1H,J=1.0,8.2 Hz), 7.47(ddd, 1H,J=1.0,7.2,8.0 Hz), 7.56(ddd,1H, J=1.2,7.2,8.2 Hz), 7.71 (ddd,1H,J=1.2,7.3,8.3 Hz), 7.81(d,1H,J=8.3 Hz), 8.95(dd, 1H,J=1.2,8.4 Hz), 9.17(dd,1H,J=1.2,8.0 Hz), 11.88(s,1H).

FABMS(m/z); 382(M+1)$^+$

Example 89

Compound 93

According to Example 45, 90 mg (69%) of a free base of Compound 93 was obtained from 110 mg (0.29 mmol) of Compound 92, 30 mg (0.75 mmol) of sodium hydride and 54 mg (0.37 mmol) of 2-dimethylaminoethyl chloride hydrochloride.

According to Example 13, 92 mg (95%) of Compound 93 was obtained from 90 mg (0.20 mmol) of the free base of Compound 93.

Free base $^1$HNMR(CDCl$_3$)∂; 2.41(s,6H), 2.72(t,2H,J=7.6 Hz), 3.29 (s,3H), 4.01(s,3H), 4.55(t,2H,J=7.6 Hz), 7.34(ddd,1H,J=1.1, 7.1,8.2 Hz), 7.43(m,1H), 7.48(dd,1H,J=0.7,8.5 Hz), 7.55(d, 1H,J=8.3 Hz), 7.60(ddd,1H,J=1.5,7.2, 8.5 Hz), 7.64(ddd,1H, J=1.3,7.1,8.3 Hz), 8.94(dd,1H,J=1.4,8.2 Hz), 9.24(d,1H,J= 7.9 Hz).

FABMS(m/z); 453(M+1)$^+$

Example 90

Compound 94

According to Example 88, 6 mg of (17%) of Compound 94 was obtained from 30 mg (0.07 mmol) of Compound 28, 9 mg (0.03 mmol) of triphosgene, 0.012 ml (0.09 mmol) triethylamine and 35 mg (0.26 mmol) of aluminum chloride.

$^1$HNMR(CDCl$_3$)∂; 0.80(t,6H,J=7.1 Hz), 1.87(m,2H), 2.15(t,2H,J=6.9 Hz), 2.29(q, 4H,J=7.1 Hz), 3.33(s,3H), 4.91 (t,2H,J=7.3 Hz), 7.26(dd,1H, J=1.4,8.2 Hz), 7.33(ddd,1H,J= 1.3,7.2,8.3 Hz), 7.46(ddd,1H,J=1.4,6.9, 8.0 Hz), 7.53(ddd, 1H,J=1.3, 6.9, 8.2 Hz), 7.67(m,2H), 9.01(dd,1H,J=1.1, 8.3 Hz), 9.34(d,1H,J=8.0 Hz), 10.04(br s,1H).

FABMS(m/z); 481(M+1)$^+$

Example 91

Compound 95

In 20 ml of toluene were suspended 6.76 g (17.1 mmol) of 2-[2-(3-nitrophenyl)vinyl]-1-trimethylsilylethoxymethyl and 3.77 g (34 mmol) of N-methylmaleimide, followed by stirring in a stream of argon at 120° C. for 7 hours. To the mixture, 3.77 g (34 mmol) of N-methylmaleimide was added, followed by stirring at the same temperature for 6 hours. The reaction mixture was purified by silica gel column chromatography (toluene/AcOEt=29/1) to give 7.11 g (82%) of a 1,2,3,4-tetrahydro compound of Compound 95.

In 190 ml of dioxane were suspended 6.54 g (13.2 mmol) of the 1,2,3,4-tetrahydro compound of Compound 95 and 6.54 g (28.8 mmol) of DDQ, followed by stirring at 120° C. for 1 hour. The resulting precipitate was removed by filtration, and the filtrate was evaporated. The residue was purified by silica gel column chromatography (toluene/AcOEt=29/1) and triturated with AcOEt to give 4.85 g (75%) of Compound 95.

$^1$HNMR(CDCl$_3$)∂; 0.10(s, 9H), 0.91(t, 2H,J=8.0 Hz), 3.22(s, 3H), 3.59(t, 2H, J=8.0 Hz), 5.77(s, 2H), 7.45(ddd, 1H, J=1.1, 7.0, 8.0 Hz), 7.61(dd, 1H, J=0.8, 7.4 Hz), 7.64–7.68(m, 2H), 7.68(s, 1H), 7.97(ddd, 1H, J=1.1, 1.7, 7.6 Hz), 8.33(ddd, 1H, J=1.1, 2.1, 8.3 Hz), 8.48(t, 1H, J=2.1 Hz), 9.15(dt, 1H, J=1.0, 8.0 Hz).

FABMS(m/z); 502(M+1)$^+$

Example 92

Compound 96 and Compound 97

According no Example 5, Compound 96 was obtained from 1.86 g (3.7 mmol) of Compound 95 and 600 mg of 10% Pd/C.

FABMS(m/z); 472(M+1)$^{30}$

According to Example 44, 1.12 g (50% yield from Compound 95) of Compound 97 was obtained by treating 600 mg of Compound 96 with 800 mg (3.7 mmol) of pyridine and 1.52 g (9.0 mmol) of benzyloxycarbonyl chloride.

$^1$HNMR(CDCl$_3$)∂; 0.10(s, 9H), 0.90(t, 2H, J=8.0 Hz), 3.20(s, 3H), 3.57(t, 2H, J=8.0 Hz), 5.21(s, 2H), 5.75(s, 2H), 6.78(s, 1H), 7.30(m, 1H), 7.32–7.44(m, 7H), 7.51(d, 1H, J=7.9 Hz), 7.59(dd, 1H, J=7.2 Hz), 7.62(dd, 1H, J=1.2, 6.8 Hz), 7.64(m, 1H), 7.66(m, 1H), 9.14(dt, 1H, J=0.8, 7.9 Hz).

FABMS(m/z); 606(M+1)$^+$

Example 93

Compound 98

According to Example 45, 271 mg (58%) of Compound 98 was obtained from 417 mg (0.69 mmol) of Compound 97, 82 mg (2.06 mmol) of 60% sodium hydride and 149 mg (1.03 mmol) of 2-dimethylaminoethyl chloride hydrochloride.

$^1$HNMR(CDCl$_3$)∂; 0.10(s, 9H), 0.90(t, 2H, J=8.0 Hz), 2.27(s, 6H), 2.58(t, 2H, J=7.2 Hz), 3.21(s, 3H), 3.57(t, 2H, J=8.0 Hz), 3.57(t, 2H, J=8.0 Hz), 3.90(t, 2H, J=7.2 Hz), 5.19(s, 2H), 5.74(s, 2H), 7.26–7.52(m, 10H), 7.59–7.64(m, 2H), 7.65(s, 1H), 9.15(dt, 1H, J=0.9, 7.9 Hz).

FABMS(m/z); 677(M+1)$^+$

Example 94

Compound 99

To a solution of 250 mg (0.37 mmol) of Compound 98 in 10 ml of THF was added t ml of 6N hydrochloric acid, followed by stirring for 10 hours at room temperature and then for 4 hours while heating under reflux. After evaporation of the solvent under reduced pressure, the residue was purified by silica gel column chromatography (CHCl$_3$/MeOH=19/1) to give 100 mg (49%) of Compound 99.

$^1$HNMR(CDCl$_3$)∂; 2.87(s, 6H), 3.06(s, 3H), 3.23(br s, 2H), 4.19(br s, 2H), 5.27(s, 2H), 7.20–7.38(m, 10H), 7.49–7.55(m, 2H), 7.92(s, 1H), 8.84(d, 1H, J=7.8 Hz), 10.03(br s, 1H).

FABMS(m/z); 547(M+1)$^+$

Example 95

Compound 100

To a solution of 464 mg (0.85 mmol) of Compound 99 in 15 ml of DMF was added 46 mg of 10% Pd/C, followed by stirring for 10 hours in a stream of hydrogen an room temperature. After filtering the reaction mixture, the filtrate was evaporated under reduced pressure, and the resulting residue was purified by preparatory HPLC (GL Science Inc., Unisil Q C18, 5 um, 20×250 mm, acetonitrile/0.1M aqueous ammonium acetate solution=50/50) to give 119 mg (34%) of a free base of Compound 100.

According to Example 13, 80 mg (57%) of Compound 100 was obtained from 119 mg (0.29 mmol) of the free base of Compound 100.

$^1$HNMR(DMSO-d$_6$)∂; 2.84(s, 6H), 3.09(s, 3H), 3.30(t, 2H, J=6.5 Hz), 3.49(t, 2H, J=6.5 Hz), 6.74(ddd, 1H, J=0.9, 2.3, 8.1 Hz), 6.85(m, 1H), 6.93(t, 1H, J=1.8 Hz), 7.22(t, 1H, J=7.2 Hz), 7.32(ddd, 1H, J=1.1, 7.0, 8.0 Hz), 7.56(ddd, 1H, J=1.1, 7.0, 8.0 Hz), 7.62(dt, 1H, J=0.9, 8.1 Hz), 7.65(s, 1H), 8.93(d, 1H, J=8.0 Hz), 10.05(br s, 1H), 12.06(s, 1H).

FABMS(m/z); 413(M+1)$^+$

Example 96

Compound 101

According to Example 54, 3.21 g (91%) of 2-[2-(2-acetoxyphenyl)vinyl]-1-methylindole was obtained from 3.02 g (12.13 mmol) of 2-[2-(2-hydroxyphenyl)vinyl]-1-methylindole, 25 mg (0.12 mmol) of DMAP, 3.4 ml (24.26 mmol) of triethylamine and 2.0 ml (18.20 mmol) of acetic anhydride.

In a stream of argon, 6.07 g (20.86 mmol) of 2-[2-(2-acetoxyphenyl)vinyl]-1-methylindole and 4.64 g (41.72 mmol) of N-methylmaleimide were stirred at 180° C. for 10 minutes. CHCl$_3$ was added to the reaction mixture, and then the solvent was evaporated. The residue was triturated with MeOH to give 6.97 g (83%) of a 1,2,3,4-tetrahydro compound of Compound 101.

$^1$HNMR(CDCl$_3$)∂; 2.30(s, 3H), 2.78(s, 3H), 2.99(m, 1H), 3.27(m, 1H), 3.48(m, 1H), 3.67(s, 3H), 3.74(dd, 1H, J=3.4, 7.6 Hz), 4.45(d, 1H, J=7.6 Hz), 7.09(m, 1H), 7.16–7.35(m, 5H), 7.76(m, 1H), 7.99(m, 1H).

FABMS(m/z); 402(M+1)$^+$

To a solution of 6.97 g (17.32 mmol) of the 1,2,3,4-tetrahydro compound of Compound 101 in 350 ml of toluene was added 7.88 g (34.70 mmol) of DDQ, followed by stirring at room temperature for 10 minutes. The reaction mixture was filtered, and the resulting precipitate was washed with CHCl$_3$. The combined organic layer was washed succesively with an aqueous saturated sodium hydrogencarbonate solution, water and brine, and dried over Na$_2$SO$_4$, and evaporated. The residue was triturated with MeOH to give 6.78 g (98%) of Compound 101.

$^1$HNMR(CDCl$_3$)∂; 1.89(s, 3H), 3.21(s, 3H), 3.91(s, 3H), 7.25(m, 1H), 7.41(m, 2H), 7.46(s, 1H), 7.48(m, 2H), 7.51(dt,

1H, J=1.8, 7.8 Hz), 7.65(ddd, 1H, J=1.2, 7.2, 8.3 Hz), 9.12(d, 1H, J=7.9 Hz).

FABMS(m/z); 399(M+1)$^+$

Example 97

Compound 102 and Compound 103

According to Example 66, 12 mg (26%) of a free base of Compound 102 and 25 mg (58%) of Compound 103 were obtained from 36 mg (0.10 mmol) of Compound 65, 38 mg (0.24 mmol) of 2-dimethylaminoisopropyl chloride hydrochloride and 72 mg (0.52 mmol) of potassium carbonate.

According to Example 13, 1.22 g (94%) of Compound 102 was obtained from 1.20 g (2.72 mmol) of the free base of Compound 102.

Compound 102

$^1$HNMR(DMSO-d$_6$)∂; 1.10(d, 3H, J=4.2 Hz), 2.59(br s, 6H), 3.05(s, 3H), 3.05(m, 1H), 3.18(m, 1H), 3.98(s, 3H), 4.95(m, 1H), 7.12(t, 1H, J=7.7 Hz), 7.27(m, 1H), 7.40(m, 2H), 7.47(m, 1H), 7.67(ddd, 1H, J=1.2, 7.3, 8.3 Hz), 7.75(d, 1H, J=8.3 Hz), 7.81(br s, 1H), 8.96(d, 1H, J=7.9 Hz), 9.97(br, 1H).

FABMS(m/z); 442(M+1)$^+$

Compound 103

$^1$HNMR(CDCl$_3$)∂; 0.88(d, 3H, J=5.6 Hz), 2.15(s, 6H), 2.73(m, 1H), 3.17(s, 3H), 3.87(m, 1H), 3.90(s, 3H), 4.07(dd, 1H, J=5.0, 9.2 Hz), 7.02(dd, 1H, J=0.9, 8.4 Hz), 7.09(dt, 1H, J=0.9, 7.6 Hz), 7.37(dd, 1H, J=1.9, 8.5 Hz), 7.40(ddd, 1H, J=0.9, 7.2, 8.0 Hz), 7.43(ddd, 1H, J=1.9, 7.6, 8.4 Hz), 7.46(d, 1H, J=8.3 Hz), 7.49(s, 1H), 7.62(ddd, 1H, J=1.2, 7.2, 8.3 Hz), 9.11(ddd, 1H, J=0.7, 1.2, 8.0 Hz).

FABMS(m/z); 442(M+1)$^+$

Example 98

Compound 104

According to Example 45, 79 mg (64%) of a free base of Compound 104 was obtained from 100 mg (0.28 mmol) of Compound 65, 89 mg (0.56 mmol) of 3-dimenhylaminopropyl chloride hydrochloride and 155 mg (1.12 mmol) of potassium carbonate.

According to Example 13, 75 mg (99%) of Compound 104 was obtained from 70 mg (0.16 mmol) of the free base of Compound 104.

$^1$HNMR(DMSO-d$_6$)∂; 1.87(m, 2H), 2.58(s, 6H), 2.87(m, 2H), 3.08(s, 3H), 3.99(s, 3H), 4.03(m, 2H), 7.09(m, 1H), 7.14(d, 1H, J=8.3 Hz), 7.35–7.49(m, 3H), 7.66(dt, 1H, J=7.3, 8.3 Hz), 7.76(d, 1H, J=8.3 Hz), 7.82(s, 1H), 8.96(d, 1H, J=7.6 Hz), 9.75(br, 1H).

FABMS(m/z); 442(M+1)$^+$

Example 99

Compound 105

To a solution of 700 mg (1.96 mmol) of Compound 65 in 13 ml of DMF were added 690 mg (7.84 mmol) of ethylene carbonate and 760 mg (2.36 mmol) of tetra-n-butylammonium bromide, followed by stirring at 140° C. for 7 hours. Water was added to the reaction mixture, followed by extraction with CHCl$_3$. The extract was washed with brine, dried over Na$_2$SO$_4$, and evaporated. The residue was purified by silica gel column chromatography (toluene/ AcOEt=4/1) to give 615 mg (78%) of Compound 105.

$^1$HNMR(CDCl$_3$)∂; 2.10(t, 1H, J=6.8 Hz), 3.19(s, 3H), 3.76(m, 2H), 3.91(s, 3H), 4.15(m, 2H), 7.05(dd, 1H, J=0.9, 8.4 Hz), 7.11(dt, 1H, J=0.9, 7.5 Hz), 7.37(dd, 1H, J=1.7, 7.5 Hz), 7.40(ddd, 1H, J=0.9, 7.3, 8.0 Hz), 7.44(m, 1H), 7.46(d, 1H, J=8.3 Hz), 7.48(s, 1H), 7.63(ddd, 1H, J=1.2, 7.3, 8.3 Hz), 9.11(dd, 1H, J=1.2, 8.0 Hz).

FABMS(m/z); 401(M+1)$^+$

Example 100

Compound 106

According to Example 2, 20 mg (19%) of Compound 106 was obtained from 100 mg (0.25 mmol) of Compound 105, 28 mg (0.70 mmol) of 60% sodium hydride and 0.034 ml (0.55 mmol) of methyl iodide.

$^1$HNMR(CDCl$_3$)∂; 3.187(s, 3H), 3.193(s, 3H), 3.51(t, 2H, J=4.9 Hz), 3.91(s, 3H), 4.12(m, 2H), 7.04(d, 1H, J=8.3 Hz), 7.10(dt, 1H, J=1.0, 7.5 Hz), 7.38(dd, 1H, J=1.5, 7.5 Hz), 7.42(m, 2H), 7.46(d, 1H, J=8.3 Hz), 7.53(s, 1H), 7.62(ddd, 1H, J=1.2, 7.3, 8.3 Hz), 9.12(d, 1H, J=7.6Hz).

FABMS(m/z); 415(M+1)$^+$

Example 101

Compound 107

According to Example 66, 106 mg (74%) of Compound 107 was obtained from 120 mg (0.34 mmol) of Compound 65, 0.06 ml (0.50 mmol) of 1-bromo-3-methylbutane and 93 mg (0.67 mmol) of potassium carbonate.

$^1$HNMR(CDCl$_3$)∂; 0.79(d, 6H, J=6.6 Hz), 1.43(q, 2H, J=6.7 Hz), 1.52(m, 1H), 3.18(s, 3H), 3.90(s, 3H), 3.98(t, 2H, J=6.7 Hz), 7.02(d, 1H, J=8.3 Hz), 7.07(dt, 1H, J=1.0, 7.5 Hz), 7.36(dd, 1H, J=1.7, 7.5 Hz), 7.40(m, 1H), 7.42(m, 1H), 7.46(d, 1H, J=8.3 Hz), 7.50(s, 1H), 7.62(ddd, 1H, J=1.2, 7.3, 8.3 Hz), 9.12(d, 1H, J=7.8 Hz).

FABMS(m/z); 427(M+1)$^+$

Example 102

Compound 108

According to Example 66, 177 mg (98%) of Compound 108 was obtained from 150 mg (0.42 mmol) of Compound 65, 0.064 ml (0.63 mmol) of 3-chloro-2-butanone and 290 mg (2.10 mmol) of potassium carbonate.

$^1$HNMR(CDCl$_3$)∂; 1.27(d, 3H, J=6.8 Hz), 1.20(s, 3H), 3.19(s, 3H), 3.92(s, 3H), 4.60(q, 1H, J=6.8 Hz), 6.80(d, 1H, J=8.5 Hz), 6.93–7.75(m, 7H), 9.09(d, 1H, J=7.8 Hz).

FABMS(m/z); 427(M+1)$^+$

Example 103

Compound 109

According to Example 66, 178 mg (95%) of Compound 109 was obtained from 150 mg (0.42 mmol) of Compound 65, 0.07 ml (0.63 mmol) of methyl 2-bromopropionate and 180 mg (1.30 mmol) of potassium carbonate.

$^1$HNMR(CDCl$_3$)∂; 1.36(d, 3H, J=6.9 Hz), 3.19(s, 3H), 3.69(s, 3H), 3.92(s, 3H), 4.75(q, 1H, J=6.9 Hz), 6.89(d, 1H, J=8.3 Hz), 7.12(dt, 1H, J=1.0, 7.5 Hz), 7.39(m, 3H), 7.46(d, 1H, J=8.3 Hz), 7.62(ddd, 1H, J=1.2, 7.3, 8.3 Hz), 7.64(s, 1H), 9.11(d, 1H, J=7.8 Hz).

FABMS(m/z); 443(M+1)$^+$

Example 104

Compound 110

To a solution of 137 mg (0.31 mmol) of Compound 109 in 10 ml of dioxane was added 10 ml of 1N hydrochloric acid, followed by stirring at 100° C. for 7 hours. To the reaction mixture was added 50 ml of water, and the resulting precipitate was collected by filtration, washed with water, and recrystallized from CHCl₃-n-hexane to give 120 mg (91%) of Compound 110.

¹HNMR(CDCl₃)∂; 1.42(d, 3H, J=7.0 Hz), 3.23(s, 3H), 3.94(s, 3H), 4.73(q, 1H, J=7.0 Hz), 6.88(d, 1H, J=8.3 Hz), 7.18(dt, 1H, J=1.0, 7.6 Hz), 7.43(s, 1H), 7.43(m, 3H), 7.48(d, 1H, J=8.3 Hz), 7.65(ddd, 1H, J=1.2, 7.3, 8.3 Hz), 9.11(ddd, 1H, J=0.7, 1.2, 8.1 Hz).

FABMS(m/z); 429(M+1)⁺

Example 105

Compound 111

To a solution of 100 mg (0.23 mmol) of Compound 110 in 3 ml of THF was added 0.17 ml (2.30 mmol) of thionyl chloride, followed by stirring at room temperature for 3 hours. To the mixture, 1.00 ml (9.53 mmol) of 50% aqueous dimethylamine solution and 3 ml of THF were added under an ice-cooled condition, followed by stirring at room temperature for 1 hour. To the reaction mixture, 2N hydrochloric acid was added, followed by extraction with CHCl₃. The extract was washed with water and then brine, dried over Na₂SO₄, and evaporated. The residue was purified by preparatory thin-layer chromatography (CHCl₃/MeOH=10/1) to give 70 mg (66%) of Compound 111.

¹HNMR(CDCl₃)∂; 1.36(d, 3H, J=6.7 Hz), 2.87(br s, 3H), 2.91(br s, 3H), 3.19(s, 3H), 3.92(s, 3H), 4.96(q, 1H, J=6.7 Hz), 6.89(m, 1H), 7.10(dt, 1H, J=1.0, 7.3 Hz), 7.38(s, 1H), 7.39(m, 2H), 7.47(d, 1H, J=8.3 Hz), 7.63(ddd, 1H, J=1.2, 7.1, 8.3 Hz), 7.63(m, 1H), 9.11(ddd, 1H, J=0.7, 1.2, 7.9 Hz).

FABMS(m/z); 443(M+1)⁺

Example 106

Compound 112

According to Example 66, 105 mg (80%) of Compound 112 was obtained from 100 mg (0.28 mmol) of Compound 65, 109 mg (0.56 mmol) of 2-bromo-N,N-dimethyl-n-butyramide and 78 mg (0.56 mmol) of potassium carbonate.

¹HNMR(CDCl₃)∂; 0.83(t, 3H, J=7.3 Hz), 1.71(m, 2H), 2.88(br s, 3H), 2.90(br s, 3H), 3.18(s, 3H), 3.91(s, 3H), 4.76(m, 1H), 6.90(m, 1H), 7.09(dt, 1H, J=0.9, 7.5 Hz), 7.38(m, 2H), 7.40(m, 1H), 7.47(d, 1H, J=8.3 Hz), 7.63(ddd, 1H, J=1.2, 7.2, 8.3 Hz), 7.67(m, 1H), 9.12(dd, 1H, J=1.2, 8.0 Hz).

FABMS(m/z); 470(M+1)⁺

Example 107

Compound 113

To a solution of 104 mg (0.22 mmol) of Compound 112 in 2 ml of methylene chloride was added 41 mg (0.28 mmol) of trimethyloxoniumtetrafluoroborate, followed by stirring at room temperature for 11 hours. The resulting mixture was evaporated under reduced pressure, and the residue was suspended in 2 ml of methanol, and then 28 mg (0.45 mmol) of sodium cyanoborohydride was added thereto under an ice-cooled condition. After stirring at room temperature for 24 hours, 4 ml of THF and 28 mg (0.45 mmol) of sodium cyanoborohydride were added thereto, followed by stirring for 6 hours. An aqueous saturated sodium hydrogencarbonate solution was added to the reaction mixture, followed by extraction with CHCl₃. The extract was washed with brine, dried over Na₂SO₄, and evaporated. The residue was purified by silica gel column chromatograPhY (CHCl₃/MeOH= 20/1) to give 28 mg (28%) of Compound 113.

¹HNMR(CDCl₃)∂; 0.75(t, 3H, J=7.4 Hz), 1.61(m, 2H), 2.12(s, 6H), 2.28(dd, 1H, J=5.6, 12.9 Hz), 2.37(dd, 1H, J=5.4, 12.9 Hz), 3.18(s, 3H), 3.90(s, 3H), 4.30(m, 1H), 7.06(m, 1H), 7.07(d, 1H, J=7.7 Hz), 7.36(dd, 1H, J=1.8, 7.7 Hz), 7.40(m, 2H), 7.46(d, 1H, J=8.3 Hz), 7.52(s, 1H), 7.62(ddd, 1H, J=1.2, 7.2, 8.3 Hz), 9.12(d, 1H, J=7.9 Hz).

FABMS(m/z); 456(M+1)⁺

Example 108

Compound 114

According to Example 45, 505 mg (78%) of Compound 114 was obtained from 553 mg (1.55 mmol) of Compound 65, 93 mg (2.33 mmol) of 60% sodium hydride and 0.56 ml (3.10 mmol) of 2-chloroethyl p-toluenesulfonate.

¹HNMR(CDCl₃)∂; 3.17(s, 3H), 3.59(t, 2H, J=5.6 Hz), 3.89(s, 3H), 4.23(t, 2H, J=5.6 Hz), 6.90–7.80(m, 7H), 7.54 (s, 1H), 9.10(dd, 1H, J=1.0, 7.6 Hz).

FABMS(m/z); 419(M+1)⁺

Example 109

Compound 115

To a solution of 100 mg (0.24 mmol) of Compound 114 in 3 ml of DMF was added 1.43 g (9.54 mmol) of sodium iodide, followed by stirring at 100° C. for 24 hours. After adding water to the reaction mixture, the resulting precipitate was collected by filtration, washed with water and then MeOH, and dried under reduced pressure to give 114 mg (94%) of Compound 115.

¹HNMR(CDCl₃)∂; 3.18(s, 3H), 3.18(m, 2H), 3.92(s, 3H), 4.20(t, 2H, J=6.5 Hz), 6.92(d, 1H, J=8.5 Hz), 7.00–7.80(m, 7H), 9.16(d, 1H, J=7.8 Hz).

FABMS(m/z); 511(M+1)⁺

Example 110

Compound 116

According to Example 20, 41 mg (43%) of a free base of Compound 116 was obtained from 120 mg (0.24 mmol) of Compound 115 and 0.60 ml (4.80 mmol) of 28% aqueous ammonia.

According to Example 13, 77 mg (84%) of Compound 116 was obtained from 85 mg (0.21 mmol) of the free base of Compound 116.

¹HNMR(DMSO-d₆)∂; 3.01(m, 2H), 3.07(s, 3H), 3.99(s, 3H), 4.16(m, 2H), 7.13(dt, 1H, J=0.8, 7.5 Hz), 7.18(dd, 1H, J=0.8, 8.2 Hz), 7.40(ddd, 1H, J=0.9, 7.2, 8.0 Hz), 7.41(dd, 1H, J=1.7, 7.5 Hz), 7.47(ddd, 1H, J=1.7, 7.5, 8.2 Hz), 7.66(ddd, 1H, J=1.1, 7.2, 8.4 Hz), 7.74(br, 3H), 7.75(d, 1H, J=8.4 Hz), 7.84(s, 1H), 8.97(dd, 1H, J=1.1, 8.0 Hz).

FABMS(m/z); 400(M+1)⁺

Example 111

Compound 117

According to Example 20, 64 mg (65%) of a free base of Compound 117 was obtained from 120 mg (0.24 mmol) of Compound 115 and 0.25 ml (2.40 mmol) of 30% methylamine-ethanol solution.

According to Example 13, 58 mg (85%) of Compound 117 was obtained from 60 mg (0.15 mmol) of the free base of Compound 117.

¹HNMR(DMSO-d₆)∂; 2.38(br s, 3H), 3.07(s, 3H), 3.12 (m, 2H), 3.97(s, 3H), 4.23(m, 2H), 7.13(dt, 1H, J=1.0, 7.4 Hz), 7.19(d, 1H, J=8.3 Hz), 7.40(m, 2H), 7.47(m, 1H), 7.67(ddd, 1H, J=1.2, 7.3, 8.4 Hz), 7.76(d, 1H, J=8.4 Hz), 7.84(s, 1H), 8.50(br, 2H), 8.97(d, 1H, J=7.6 Hz).

FABMS(m/z); 414(M+1)⁺

Example 112

Compound 118

According to Example 20, 64 mg (60%) of a free base of Compound 118 was obtained from 120 mg (0.24 mmol) of Compound 115 and 0.20 ml (2.40 mmol) of n-propylamine.

According to Example 13, 53 mg (79%) of Compound 118 was obtained from 60 mg (0.14 mmol) of the free base of Compound 118.

$^1$HNMR(DMSO-d$_6$)∂; 0.51(t, 3H, J=7.5 Hz), 1.30(m, 2H), 2.56(m, 2H), 3.07(s, 3H), 3.12(m, 2H), 3.99(s, 3H), 4.23(m, 2H), 7.13(dt, 1H, J=0.8, 7.5 Hz), 7.18(dd, 1H, J=0.8, 8.2 Hz), 7.40(m, 2H), 7.47(ddd, 1H, J=1.8, 7.5, 8.2 Hz), 7.67(ddd, 1H, J=1.1, 7.1, 8.3 Hz), 7.75(d, 1H, J=8.3 Hz), 7.84(s, 1H), 8.46(br, 2H), 8.96(dd, 1H, J=1.0, 7.9 Hz).

FABMS(m/z); 442(M+1)$^+$

Example 113

Compound 119

According to Example 6, 0.17 g (53%) of a free base of Compound 119 was obtained from 0.30 g (0.67 mmol) of a free base of Compound 118, 0.53 ml (6.70 mmol) of 35% formalin and 1.42 g (6.70 mmol) of sodium triacetoxyborohydride.

According to Example 13, 153 mg (89%) of Compound 119 was obtained from 160 mg (0.35 mmol) of the free base of Compound 119.

$^1$HNMR(DMSO-d$_6$)∂; 0.47(m, 3H), 1.32(m, 2H), 2.54(br s, 3H), 2.68(m, 1H), 2.78(m, 1H), 3.07(s, 3H), 3.30(m, 2H), 3.99(s, 3H), 4.33(m, 2H), 7.13(dt, 1H, J=0.7, 7.3 Hz), 7.18(d, 1H, J=8.1 Hz), 7.40(m, 2H), 7.48(ddd, 1H, J=1.7, 7.4, 8.4 Hz), 7.67(ddd, 1H, J=1.2, 7.4, 8.3 Hz), 7.75(d, 1H, J=8.3 Hz), 7.84(s, 1H), 8.96(dd, 1H, J=1.2, 8.4 Hz), 9.72(br, 1H).

FABMS(m/z); 456(M+1)$^+$

Example 114

Compound 120

According to Example 20, 76 mg (72%) of a free base of Compound 120 was obtained from 120 mg (0.24 mmol) of Compound 115 and 0.20 ml (2.40 mmol) of isopropylamine.

According to Example 13, 69 mg (90%) of Compound 120 was obtained from 70 mg (0.16 mmol) of the free base of Compound 120.

$^1$HNMR(DMSO-d$_6$)∂; 0.93(d, 6H, J=6.5 Hz), 3.04(m, 1H), 3.07(s, 3H), 3.12(m, 2H), 3.99(s, 3H), 4.23(m, 2H), 7.13(dt, 1H, J=0.7, 7.6 Hz), 7.18(dd, 1H, J=0.7, 8.3 Hz), 7.40(m, 2H), 7.48(ddd, 1H, J=1.8, 7.6, 8.3 Hz), 7.67(ddd, 1H, J=1.1, 7.1, 8.3 Hz), 7.76(d, 1H, J=8.3 Hz), 7.86(s, 1H), 8.51(br, 2H), 8.96(ddd, 1H, J=0.6, 1.1, 7.9 Hz).

FABMS(m/z); 442(M+1)$^+$

Example 115

Compound 121

According to Example 6, 0.16 g (51%) of a free base of Compound 121 was obtained from 0.31 g (0.70 mmol) of a free base of Compound 120, 0.55 ml (7.00 mmol) of 35% formalin and 1.48 g (3.30 mmol) of sodium triacenoxyborohydride.

According to Example 13, 128 mg (77%) of Compound 121 was obtained from 155 mg (0.34 mmol) of the free base of Compound 121.

$^1$HNMR(DMSO-d$_6$)∂; 0.85(br s, 3H), 0.99(d, 3H, J=6.6 Hz), 2.46(br s, 3H), 3.07(s, 3H), 3.16(m, 1H), 3.30(m, 2H), 4.00(s, 3H), 4.34(m, 2H), 7.13(dt, 1H, J=1.0, 7.6 Hz), 7.19(d, 1H, J=8.1 Hz), 7.40(m, 2H), 7.48(ddd, 1H, J=1.6, 7.2, 8.0 Hz), 7.67(ddd, 1H, J=1.2, 7.2, 8.3 Hz), 7.76(d, 1H, J=8.3 Hz), 7.85(s, 1H), 8.96(d, 1H, J=8.0 Hz), 9.58(br, 1H).

FABMS(m/z); 456(M+1)$^+$

Example 116

Compound 122

According to Example 20, 67 mg (60%) of a free base of Compound 122 was obtained from 120 mg (0.24 mmol) of Compound 115 and 0.24 ml (2.40 mmol) of cyclopentylamine.

According to Example 13, 49 mg (75%) of Compound 122 was obtained from 60 mg (0.13 mmol) of the free base of Compound 122.

$^1$HNMR(DMSO-d$_6$)∂; 1.07(m, 2H), 1.28(m, 2H), 1.37(m, 2H), 1.54(m, 2H), 3.07(s, 3H), 3.13(m, 2H), 3.36(m, 1H), 3.99(s, 3H), 4.22(m, 2H), 7.14(dt, 1H, J=1.4, 7.6 Hz), 7.18(d, 1H, J=8.0 Hz), 7.40(m, 1H), 7.41(d, 1H, J=7.6 Hz), 7.48(ddd, 1H, J=1.4, 7.6, 8.0 Hz), 7.67(ddd, 1H, J=1.2, 7.3, 8.5 Hz), 7.76(d, 1H, J=8.5 Hz), 7.84(s, 1H), 8.55(m, 2H), 8.96(d, 1H, J=7.8 Hz).

FABMS(m/z); 468(M+1)$^+$

Example 117

Compound 123

According to Example 54, 361 mg (83%) of 2-[2-(2-acetoxy-5-fluorophenyl)vinyl]-1-methylindole was obtained from 378 mg (1.41 mmol) of 2-[2-(5-fluoro-2-hydroxyphenyl)vinyl]-1-methylindole, 12 mg (0.06 mmol) of DMAP, 0.39 ml (2.82 mmol) of triethylamine and 0.20 ml (2.12 mmol) of acetic anhydride.

$^1$HNMR(CDCl$_3$)∂; 2.37(s, 3H), 3.82(s, 3H), 6.80(s, 1H), 6.99(ddd, 1H, J=2.9, 7.8, 9.0 Hz), 7.07(dd, 1H, J=5.0, 9.0Hz), 7.10(m, 3H), 7.22(ddd, 1H, J=1.2, 7.1, 8.0 Hz), 7.31(d, 1H, J=8.3 Hz), 7.37(dd, 1H, J=2.9, 9.5 Hz), 7.59(d, 1H, J=8.0 Hz).

FABMS(m/z); 309(M)$^+$

According to Example 96, 424 mg (88%) of a 1,2,3,4-tetrahydro compound of Compound 123 was obtained from 356 mg (1.15 mmol) of [2-(2-acetoxy-5-fluorophenyl)vinyl]-1-methylindole and 256 mg (2.30 mmol) of N-methylmaleimide.

$^1$HNMR(CDCl$_3$)∂; 2.28(s, 3H), 2.80(s, 3H), 2.98(dd, 1H, J=4.2, 5.5 Hz), 3.20(ddd, 1H, J=2.2, 12.5, 15.5 Hz), 3.41(m, 1H), 3.67(s, 3H), 3.73(dd, 1H, J=3.4, 7.4 Hz), 4.45(d, 1H, J=7.4 Hz), 7.05(m, 2H), 7.17–7.32(m, 3H), 7.51(dd, 1H, J=1.0, 9.0 Hz), 7.99(d, 1H, J=7.3 Hz).

FABMS(m/z); 420(M)$^+$

Then, 366 mg (89%) of Compound 123 was obtained from 418 mg (0.99 mmol) of the 1,2,3,4-tetrahydro compound of Compound 123 and 450 mg (1.98 mmol) of DDQ.

$^1$HNMR(CDCl$_3$)∂; 1.88(s, 3H), 3.21(s, 3H), 3.91(s, 3H), 7.19(m, 3H), 7.43(ddd, 1H, J=0.9, 7.1, 8.0 Hz), 7.44(s, 1H), 7.49(d, 1H, J=8.3 Hz), 7.66(ddd, 1H, J=1.1, 7.1, 8.3 Hz), 9.12(dd, 1H, J=1.1, 8.0 Hz).

FABMS(m/z); 417(M+1)$^+$

Example 118

Compound 124

To a solution of 360 mg (0.86 mmol) of Compound 123 in 63 ml of a mixed solution of ethylene chloride and MeOH (2/1) was added 143 mg (1.03 mmol) of potassium carbonate, followed by stirring at room temperature for 3 hours. To the reaction mixture, 1N hydrochloric acid was added, followed by extraction with ethylene chloride. The extract was dried over $Na_2SO_4$, and evaporated. The residue was triturated with MeOH to give 286 mg (89%) of Compound 124.

$^1$HNMR(DMSO-$d_6$)∂; 3.06(s, 3H), 3.98(s, 3H), 6.91(dd, 1H, J=4.9, 8.9 Hz), 7.10(dt, 1H, J=3.2, 8.9 Hz), 7.14(dd, 1H, J=3.2, 9.1 Hz), 7.39(d, 1H, J=7.5 Hz), 7.66(ddd, 1H, J=1.2, 7.1, 8.3 Hz), 7.74(d, 1H, J=8.3 Hz), 7.83(s, 1H), 8.95(d, 1H, J=7.8 Hz), 9.41(s, 1H).

FABMS(m/z); 375(M+1)$^+$

Example 119

Compound 125

According to Example 45, 71 mg (59%) of a free base of Compound 125 was obtained from 100 mg (0.27 mmol) of Compound 124, 58 mg (0.41 mmol) of 2-dimethylaminoethyl chloride hydrochloride and 138 mg (0.95 mmol) of potassium carbonate.

$^1$HNMR(CDCl$_3$)∂; 2.10(s, 6H), 2.44(t, 2H, J=6.0 Hz), 3.19(s, 3H), 3.92(s, 3H), 4.01(t, 2H, J=6.0 Hz), 6.96(dd, 1H, J=4.4, 9.5 Hz), 7.11(m, 2H), 7.41(ddd, 1H, J=0.9, 7.3, 8.0 Hz), 7.47(d, 1H, J=8.3 Hz), 7.48(s, 1H), 7.63(ddd, 1H, J=1.1, 7.3, 8.3 Hz), 9.12(dd, 1H, J=1.1, 8.0 Hz).

FABMS(m/z); 446(M+1)$^+$

Example 120

Compound 126

According to Example 54, 403 mg (81%) of 2-[2-(2-acetoxy-5-chlorophenyl)vinyl]-1-methylindole was obtained from 432 mg (1.52 mmol) of 2-[2-(5-chloro-2-hydroxyphenyl)vinyl]-1-methylindole, 12 mg (0.06 mmol) of DMAP, 0.43 ml (3.04 mmol) of triethylamine and 0.22 ml (2.28 mmol) of acetic anhydride.

$^1$HNMR(CDCl$_3$)∂; 2.38(s, 3H), 3.82(s, 3H), 6.80(s, 1H), 7.05(d, 1H, J=8.7 Hz), 7.09(d, 1H, J=16.2 Hz), 7.11(ddd, 1H, J=1.0, 7.0, 8.0 Hz), 7.15(d, 1H, J=16.2 Hz), 7.22(ddd, 1H, J=1.1, 7.0, 8.3 Hz), 7.25(dd, 1H, J=2.5, 8.7 Hz), 7.31(dd, 1H, J=1.0, 8.3 Hz), 7.59(dd, 1H, J=1.1, 8.0 Hz), 7.66(d, 1H, J=2.5 Hz).

FABMS(m/z); 325(M)$^+$

According to Example 96, 501 mg (94%) of a 1,2,3,4-tetrahydro compound of Compound 126 was obtained from 398 mg (1.22 mmol) of 2-[2-(2-acetoxy-5-chlorophenyl) vinyl]-1-methylindole and 271 mg (2.44 mmol) of N-methylmaleimide $^1$HNMR(CDCl$_3$)∂; 2.22(s, 3H), 2.74 s, 3H), 2.91(dd, 1H, J=4.2, 15.3 Hz), 3.16(ddd, 1H, J=2.0, 12.8, 15.3 Hz), 3.33 (dt, 1H, J=3.8, 12.8 Hz), 3.60(s, 3H), 3.65(dd, 1H, J=3.8, 7.7 Hz), 4.38(d, 1H, J=7.7 Hz), 6.97(d, 1H, J=8.6 Hz), 7.13(ddd, 1H, J=1.0, 7.2, 8.0 Hz), 7.18(ddd, 1H, J=1.3, 7.2, 8.2 Hz), 7.23(d, 1H, J=8.2 Hz), 7.25(dd, 1H, J=2.5, 8.6 Hz), 7.71(d, 1H, J=2.5 Hz), 7.92(d, 1H, J=8.0 Hz).

FABMS(m/z); 437(M+1)$^+$

Then, 446 mg (90%) of Compound 126 was obtained from 496 mg (1.14 mmol) of the 1,2,3,4-tetrahydro compound of Compound 126 and 518 mg (2.28 mmol) of DDQ.

$^1$HNMR(CDCl$_3$)∂; 1.88(s, 3H), 3.21(s, 3H), 3.92(s, 3H), 7.19(dd, 1H, J=0.8, 8.3 Hz), 7.43(ddd, 1H, J=0.9, 7.3, 8.0 Hz), 7.43(s, 1H), 7.45(dd, 1H, J=0.8, 2.5 Hz), 7.47(dd, 1H, J=2.5, 8.3 Hz), 7.49(dd, 1H, J=0.9, 7.6 Hz), 7.66(ddd, 1H, J=1.3, 7.3, 7.6 Hz), 9.12(ddd, 1H, J=0.7, 1.3, 8.0 Hz).

FABMS(m/z); 433(M+1)$^+$

Example 121

Compound 127

According to Example 118, 370 mg (93%) of Compound 127 was obtained from 441 mg (1.02 mmol) of Compound 126 and 170 mg (1.22 mmol) of potassium carbonate.

$^1$HNMR(DMSO-$d_6$)∂; 3.06(s, 3H), 3.99(s, 3H), 6.94(d, 1H, J=8.6 Hz), 7.30(dd, 1H, J=2.7, 8.6 Hz), 7.32(d, 1H, J=2.7 Hz), 7.39(dt, 1H, J=0.9, 7.5 Hz), 7.66(ddd, 1H, J=1.2, 7.1, 8.3 Hz), 7.74(d, 1H, J=8.3 Hz), 7.83(s, 1H), 8.95(d, 1H, J=7.9 Hz), 9.71(s, 1H).

FABMS(m/z); 391(M+1)$^+$

Example 122

Compound 128

According to Example 45, 83 mg (69%) of Compound 128 was obtained from 100 mg (0.26 mmol) of Compound 127, 56 mg (0.39 mmol) of 2-dimethylaminoethyl chloride hydrochloride and 126 mg (0.91 mmol) of potassium carbonate.

$^1$HNMR(CDCl$_3$)∂; 2.10(s, 6H), 2.45(t, 2H, J=5.9 Hz), 3.19(s, 3H), 3.92(s, 3H), 4.03(t, 2H, J=5.9 Hz), 6.94(d, 1H, J=8.7 Hz), 7.34(d, 1H, J=2.6 Hz), 7.37(dd, 1H, J=2.6, 8.7 Hz), 7.41(ddd, 1H, J=0.9, 7.3, 8.0 Hz), 7.46(s, 1H), 7.47(d, 1H, J=8.4 Hz), 7.64(ddd, 1H, J=1.1, 7.3, 8.4 Hz), 9.12(dd, 1H, J=1.1, 8.0 Hz).

FABMS(m/z); 462(M+1)$^+$

Example 123

Compound 129

According to Example 79, 217 mg (59%) of Compound 129 was obtained from 300 mg (0.84 mmol) of Compound 65 and 445 mg (0.92 mmol) of tetra-n-butylammonium tribromide.

$^1$HNMR(DMSO-$d_6$)∂; 3.06(s, 3H), 3.98(s, 3H), 6.90(d, 1H, J=8.5 Hz), 7.39(ddd, 1H, J=1.0, 7.3, 8.0 Hz), 7.42(dd, 1H, J=2.5, 8.5 Hz), 7.44(d, 1H, J=2.5 Hz), 7.66(ddd, 1H, J=1.0, 7.3, 8.4 Hz), 7.74(d, 1H, J=8.4 Hz), 7.83(s, 1H), 8.95(dd, 1H, J=1.0, 8.0 Hz), 9.76(s, 1H).

FABMS(m/z); 435 (M+1)$^+$

Example 124

Compound 130

According to Example 45, 73 mg (62%) of a free base of Compound 130 was obtained from 100 mg (0.23 mmol) of Compound 129, 66 mg (0.46 mmol) of 2-dimethylaminoethyl chloride hydrochloride and 159 mg (1.15 mmol) of potassium carbonate.

According to Example 13, 39 mg (80%) of Compound 130 was obtained from 45 mg (0.09 mmol) of the free base of Compound 130.

$^1$HNMR(DMSO-$d_6$)∂; 2.55(br s, 6H), 3.07(s, 3H), 3.27 (m, 2H), 3.99(s, 3H), 4.30(m, 2H), 7.18(d, 1H, J=8.9 Hz), 7.41(ddd, 1H, J=0.9, 7.1, 8.0 Hz), 7.56(d, 1H, J=2.6 Hz), 7.66(dd, 1H, J=2.6, 8.9 Hz), 7.68(ddd, 1H, J=1.0, 7.1, 8.4 Hz), 7.76(d, 1H, J=8.4 Hz), 7.90(s, 1H), 8.96(dd, 1H, J=1.0, 8.0 Hz).

FABMS(m/z); 506(M+1)$^+$

Example 125

Compound 131 and Compound 132

According to Example 45, 26 mg (18k) of Compound 131 and 46 mg (33%) of Compound 132 were obtained from 97 mg (0.22 mmol) of Compound 129, 85 mg (0.54 mmol) of 2-dimethylaminoisopropyl chloride hydrochloride and 160 mg (1.16 mmol) of potassium carbonate.

Compound 131

$^1$HNMR(CDCl$_3$)∂; 1.15(d, 3H, J=6.1 Hz), 2.11(s, 6H), 2.23(m, 1H), 2.35(m, 1H), 3.19(s, 3H), 3.92(s, 3H), 4.42(m, 1H), 6.95(d, 1H, J=8.7 Hz), 7.41(ddd, 1H, J=0.9, 7.2, 8.0 Hz), 7.46(s, 1H), 7.48(m, 3H), 7.64(ddd, 1H, J=1.1, 7.2, 8.3 Hz), 9.12(dd, 1H, J=1.1, 8.0 Hz).

FABMS(m/z); 520(M+1)$^+$

Compound 132

$^1$HNMR(CDCl$_3$)∂; 0.85(d, 3H, H=6.6 Hz), 2.13(s, 6H), 2.68(m, 1H), 3.18(s, 3H), 3.82(m, 1H), 3.93(s, 3H), a.02(dd, 1H, J=4.9, 8.8 Hz), 6.89(d, 1H, J=8.8 Hz), 7.42(ddd, 1H, J=0.9, 7.3, 7.9 Hz), 7.46(s, 1H), 7.48(d, 1H, J=2.5 Hz), 7.48(d, 1H, J=8.3 Hz), 7.52(dd, 1H, J=2.5, 8.8 Hz), 7.64 (ddd, 1H, J=1.0, 7.3, 8.3 Hz), 9.11(dd, 1H, J=1.0, 7.9 Hz).

FABMS(m/z); 520(M+1)$^+$

Example 126

Compound 133

According to Example 99, 58 mg (66%) of Compound 133 was obtained from 80 mg (0.18 mmol) of Compound 129, 65 mg (0.74 mmol) of ethylene carbonate and 71 mg (0.22 mmol) of tetra-n-butylammonium bromide.

$^1$HNMR(CDCl$_3$)∂; 2.12(t, 1H, J=6.5 Hz), 3.!9(s, 3H), 3.75(m, 2H), 3.93(s, 3H), 4.13(m, 2H), 6.93(d, 1H, J=8.8 Hz), 7.41(ddd, 1H, J=0.8, 7.3, 8.0 Hz), 7.44(s, 1H), 7.47(d, 1H, J=8.4 Hz), 7.49(d, 1H, J=2.5 Hz), 7.53(dd, 1H, J=2.5, 8.8 Hz), 7.64(ddd, 1H, J=0.9, 7.3, 8.4 Hz), 9.10(dd, 1H, J=0.9, 8.0 Hz).

FABMS(m/z); 479(M+1)$^+$

Example 127

Compound 134

According to Example 54, 381 mg (98%) of 2-[2-(2-acetoxy-5-bromophenyl)vinyl]-5-fluoro-1-methylindole was obtained from 347 mg (1.00 mmol) of 2-[2-(5-bromo-2-hydroxyphenyl)vinyl]-5-fluoro-1-methylindole, 12 mg (0.06 mmol) of DMAP, 3.00 ml (37.09 mmol) of pyridine and 0.10 ml (1.06 mmol) of acetic anhydride.

FABMS(m/z); 388(M+1)$^+$

According to Example 96, 261 mg (56%) of a 1,2,3,4-tetrahydro compound of Compound 134 was obtained from 376 mg (0.97 mmol) of 2-[2-(2-acetoxy-5-bromophenyl)vinyl]-5-fluoro-1-methylindole and 337 mg (3.04 mmol) of N-methylmaleimide.

$^1$HNMR(CDCl$_3$)∂; 2.30(s, 3H), 2.82(s, 3H), 2.96(dd, 1H, J=4.1, 15.5 Hz), 3.21(m, 1H), 3.39(m, 1H), 3.66(s, 3H), 3.71(dd, 1H, J=3.5, 7.5 Hz), 4.38(d, 1H, J=7.5 Hz), 6.98(m, 1H), 6.99(d, 1H, J=8.7 Hz), 7.20(dd, 1H, J=4.2, 8.9 Hz), 7.48(dd, 1H, J=2.4, 8.7 Hz), 7.65(dd, 1H, J=2.5, 9.6 Hz), 7.90(d, 1H, J=2.4 Hz).

FABMS(m/z); 499(M+1)$^+$

Then, 194 mg (76%) of Compound 134 was obtained from 257 mg (0.52 mmol) of the 1,2,3,4-tetrahydro compound of Compound 134 and 238 mg (1.05 mmol) of DDQ.

$^1$HNMR(CDCl$_3$)∂; 1.89(s, 3H), 3.21(s, 3H), 7.14(d, 1H, J=8.5 Hz), 7.39–7.42(m, 2H), 7.43(s, 1H), 7.59(d, 1H, J=2.4 Hz), 7.62(dd, 1H, J=2.4, 8.5 Hz), 8.82(dd, 1H, J=2.4, 9.0 Hz).

FABMS(m/z); 495(M+1)$^+$

Example 128

Compound 135 and Compound 136

According to Example 118, Compound 135 was obtained from 192 mg (0.39 mmol) of Compound 134 and 61 mg (0.44 mmol) of potassium carbonate.

FABMS(m/z); 453(M+1)$^+$

According no Example 45, 168 mg (83% yield from Compound 134) of Compound 136 was obtained by treating Compound 135 with 96 mg (0.66 mmol) of 2-dimethylaminoethyl chloride hydrochloride and 371 mg (2.68 mmol) of potassium carbonate.

$^1$HNMR(CDCl$_3$)∂; 2.11(s, 6H), 2.45(t, 2H, J=6.0 Hz), 3.19(s, 3H), 3.91(s, 3H), 4.03(t, 2H, J=6.0 Hz), 6.90(d, 1H, J=8.8 Hz), 7.35–7.40(m, 2H), 7.45(s, 1H), 7.47(d, 1H, J=2.5 Hz), 7.52(dd, 1H, J=2.5, 8.8 Hz), 8.81(m, 1H).

FABMS(m/z); 524(M+1)$^+$

Example 129

Compound 137

To a solution of 500 mg (1.26 mmol) of Compound 101 in 15 ml of methylene chloride was added 0.11 ml (1.34 mmol) of sulfuryl chloride, followed by stirring at room temperature for 35 minutes. An aqueous saturated sodium hydrogencarbonate solution was added to the reaction mixture, followed by extraction with CHCl$_3$. The extract was washed with brine, dried over Na$_2$SO$_4$, and evaporated. The residue was purified by silica gel column chromatography (toluene/AcOEt=10/1) to give 332 mg (61%) of Compound 137.

$^1$HNMR(CDCl$_3$)∂; 1.90(s, 3H), 3.i9(s, 3H), 3.87(s, 3H), 7.25(dd, 1H, J=1.1, 8.0 Hz), 7.36(d, 1H, J=8.7 Hz), 7.39(dd, 1H, J=1.1, 7.6 Hz), 7.45(s, 1H), 7.46(dd, 1H, J=1.7, 7.6 Hz), 7.51(ddd, 1H, J=1.7, 7.6, 8.0 Hz), 7.56 dd, 1H, J=2.1, 8.7 Hz), 9.06(m, 1H).

FABMS(m/z); 433(M+1)$^+$

Example 130

Compound 138

According to Example 118, 283 mg (94%) of Compound 138 was obtained from 333 mg (0.74 mmol) of Compound 137 and 120 mg (0.87 mmol) of potassium carbonate.

$^1$HNMR(DMSO-d$_6$)∂; 3.04(s, 3H), 3.96(s, 3H), 6.89(m, 1H), 6.92(m, 1H), 7.26(m, 2H), 7.65 dd, 1H, J=2.2, 8.5 Hz), 7.76(d, 1H, J=8.8 Hz), 7.79(s, 1H), 8.91(d, 1H, J=2.2 Hz), 9.41(s, 1H).

FABMS(m/z); 391($^M$+1)$^+$

Example 131

Compound 139

According to Example 45, 113 mg (64%) of a free base of Compound 139 was obtained from 150 mg (0.38 mmol) of Compound 138, 110 mg (0.76 mmol) of 2-dimethylaminoethyl chloride hydrochloride and 212 mg (1.54 mmol) of potassium carbonate.

According to Example 13, 68 mg (62%) of Compound 139 was obtained from 100 mg (0.22 mmol) of the free base of Compound 139.

$^1$HNMR(DMSO-d$_6$)∂; 2.57(br s, 6H), 3.06(s, 3H), 3.23 (m, 2H), 3.99(s, 3H), 4.31(m, 2H), 7.13(dt, 1H, J=1.0, 7.4 Hz), 7.20(d, 1H, J=8.2 Hz), 7.39(dd, 1H, J=1.7, 7.4 Hz), 7.48(ddd, 1H, J=1.7, 7.4, 8.2 Hz), 7.70(dd, 1H, J=2.2, 8.8 Hz), 7.81(d, 1H, J=8.8 Hz), 7.88(s, 1H), 8.95(d, 1H, J=2.2 Hz), 9.80(br, 1H).

FABMS(m/z); 462(M+1)⁺

Example 132

Compound 140

To a solution of 1.00 g (2.51 mmol) of Compound 101 in 25 ml of THF was added 0.49 g (2.76 mmol) of N-bromosuccinimide, followed by stirring at room temperature for 4.5 hours. A 10% aqueous sodium hydrosulfite solution was added to the reaction mixture, followed by extraction with $CHCl_3$. The extract was washed with brine, dried over $Na_2SO_4$, and evaporated. The residue was triturated with MeOH to give 1.13 g (94%) of Compound 140.

¹HNMR($CDCl_3$)∂; 1.90(s, 3H), 3.20(s, 3H), 3.89(s, 3H), 7.25(m, 1H), 7.35(d, 1H, J=8.6 Hz), 7.39(dt, 1H, J=1.2, 7.4 Hz), 7.50(m, 1H), 7.46(s, 1H), 7.52(ddd, 1H, J=2.0, 7.4, 8.1 Hz), 7.72(dd, 1H, J=2.0, 8.6 Hz), 9.27(d, 1H, J=2.0 Hz).

FABMS(m/z); 477(M+1)⁺

Example 133

Compound 141

According to Example 118, 0.99 g (96%) of Compound 141 was obtained from 1.13 g (2.36 mmol) of Compound 140 and 0.39 g (2.82 mmol) of potassium carbonate.

¹HNMR(DMSO-$d_6$)∂; 3.05(s, 3H), 3.96(s, 3H), 6.90(dt, 1H, J=1.0, 7.6 Hz), 6.93(d, 1H, J=8.5 Hz), 7.27(m, 2H), 7.72(d, 1H, J=8.8 Hz), 7.77(dd, 1H, a=2.1, 8.8 Hz), 7.80(s, 1H), 9.07(d, 1H, J=2.1 Hz), 9.43(s, 1H).

FABMS(m/z); 435(M+1)⁺

Example 134

Compound 142

According to Example 45, 94 mg (40%) of Compound 142 was obtained from 200 mg (0.46 mmol) of Compound 141, 299 mg (2.08 mmol) of 2-dimethylaminoethyl chloride hydrochloride and 590 mg (4.27 mmol) of potassium carbonate.

¹HNMR($CDCl_3$)∂; 2.14(s, 6H), 2.50(t, 2H, J=6.0 Hz), 3.20(s, 3H), 3.90(s, 3H), 4.09(t, 2H, J=6.0 Hz), 7.04(d, 1H, J=8.3 Hz), 7.10(dt, 1H, J=1.0, 7.6 Hz), 7.35(d, 1H, J=8.8 Hz), 7.37(dd, 1H, J=1.7, 7.6 Hz), 7.45(ddd, 1H, J=1.7, 7.3, 8.3 Hz), 7.52(s, 1H), 7.72(dd, 1H, J=1.9, 8.8 Hz), 9.28(d, 1H, J=1.9 Hz).

FABMS(m/z); 506(M+1)⁺

Example 135

Compound 143

According to Example 79, 88 mg (94%) of Compound 143 was obtained from 80 mg (0.18 mmol) of Compound 141 and 98 mg (0.20 mmol) of tetra-n-butylammonium tribromide.

¹HNMR(DMSO-$d_6$)∂; 3.06(s, 3H), 3.98(s, 3H), 6.90(dd, 1H, J=0.5, 8.3 Hz), 7.43(dd, 1H, J=2.6, 8.3 Hz), 7.44(d, 1H, J=2.6 Hz), 7.74(d, 1H, J=8.8 Hz), 7.79(dd, 1H, J=2.0, 8.8 Hz), 7.87(s, 1H), 9.08(d, 1H, J=2.0 Hz), 9.79(s, 1H).

FABMS(m/z); 513(M+1)⁺

Example 136

Compound 144

According to Example 45, 56 mg (59%) of Compound 144 was obtained from 83 mg (0.16 mmol) of Compound 14 mg (0.33 mmol) of 2-dimethylaminoethyl chloride hydrochloride and 45 mg (0.33 mmol) of potassium carbonate.

¹HNMR($CDCl_3$)∂; 2.10(s, 6H), 2.45(t, 2H, J=6.0 Hz), 3.19(s, 3H), 3.91(s, 3H), 4.03(t, 2H, J=6.0 Hz), 6.90(d, 1H, J=8.8 Hz), 7.35(d, 1H, J=8.8 Hz), 7.46(s, 1H), 7.47(d, 1H, J=2.4 Hz), 7.52(dd, 1H, J=2.4, 8.8 Hz), 7.71(dd, 1H, J=2.0, 8.8 Hz), 9.27 d, 1H, J=2.0 Hz).

FABMS(m/z); 584(M+1)⁺

Example 137

Compound 145

According to Example 54, 0.84 g (75%) of 2-[2-(2-acetoxy-5-benzyloxyphenyl)vinyl]-1-methylindole was obtained from 1.01 g (2.83 mmol) of 2-[2-(5-benzyloxy-2-hydroxyphenyl)vinyl]-1-methylindole, 12 mg (0.06 mmol) of DMAP, 0.79 ml (5.66 mmol) of triethylamine and 0.40 ml (4.25 mmol) of acetic anhydride.

¹HNMR($CDCl_3$)∂; 2.36(s, 3H), 3.79(s, 3H), 5.11(s, 2H), 6.78(s, 1H), 6.91(dd, 1H, J=2.9, 8.8 Hz), 7.01(d, 1H, J=8.8 Hz), 7.10(m, 2H), 7.21(ddd, 1H, J=1.2, 7.1, 8.3 Hz), 7.23–7.48(m, 8H), 7.58(d, 1H, J=7.8 Hz).

FABMS(m/z); 398(M+1)⁺

According to Example 96, 916 mg (85%) of a 1,2,3,4-tetrahydro compound of Compound 145 was obtained from 838 mg (2.11 mmol) of 2-[2-(2-acetoxy-5-benzyloxyphenyl)vinyl]-1-methylindole and 469 mg (4.22 mmol) of N-methylmaleimide.

¹HNMR($CDCl_3$)∂; 2.27(s, 3H), 2.79(s, 3H), 2.96(dd, 1H, J=4.2, 15.6 Hz), 3.19(ddd, 1H, J=2.0, 12.3, 15.6 Hz), 3.41 (dt, 1H, J=3.9, 12.3 Hz), 3.64(s, 3H), 3.74(dd, 1H, J=3.4, 7.3 Hz), 4.43(d, 1H, J=7.3 Hz), 5.10 (m, 2H), 6.93(dd, 1H, J=2.9, 9.0 Hz), 7.00(d, 1H, J=8.8 Hz), 7.16–7.48(m, 9H), 7.99(d, 1H, J=7.1 Hz).

FABMS(m/z); 509(M+1)⁺

Then, 832 mg (92%) of Compound 145 was obtained from 910 mg (1.79 mmol) of the 1,2,3,4-tetrahydro compound of Compound 145 and 813 mg (3.58 mmol) of DDQ.

¹HNMR($CDCl_3$)∂; 1.87(s, 3H), 3.21(s, 3H), 3.90(s, 3H), 5.10(s, 2H), 7.09(m, 2H), 7.16(dd, 1H, J=0.8, 8.4 Hz), 7.34(m, 1H), 7.39(m, 4H), 7.44(s, 1H), 7.44(m, 1H), 7.49(d, 1H, J=8.3 Hz), 7.65(ddd, 1H, J=1.2, 7.1, 8.3 Hz), 9.11(d, 1H, J=7.9 Hz).

FABMS(m/z); 505(M+1)⁺

Example 138

Compound 146

According to Example 118, 688 mg (91%) of Compound 146 was obtained from 825 mg (1.64 mmol) of Compound 145 and 272 mg (1.97 mmol) of potassium carbonate.

¹HNMR(DMSO-$d_6$)∂; 3.07(s, 3H), 3.98(s, 3H), 5.05(s, 2H), 6.84(d, 1H, J=8.8 Hz), 6.94(dd, 1H, J=2.9, 8.8 Hz), 6.99(d, 1H, J=2.9 Hz), 7.33(m, 1H), 7.39(m, 3H), 7.47(m, 2H), 7.65(ddd, 1H, J=1.2, 7.1, 8.4 Hz), 7.74(d, 1H, J=8.4 Hz), 7.78(s, 1H), 8.95(d, 1H, J=7.8 Hz), 8.95(s, 1H).

FABMS(m/z); 463(M+1)⁺

Example 139

Compound 147

According to Example 45, 463 mg (69%) of Compound 147 was obtained from 582 mg (1.26 mmol) of Compound 146, 272 mg (1.89 mmol) of 2-dimethylaminoethyl chloride hydrochloride and 609 mg (4.41 mmol) of potassium carbonate.

¹HNMR($CDCl_3$)∂; 2.10(s, 6H), 2.44(t, 2H, J=6.0 Hz), 3.20(s, 3H), 3.90(s, 3H), 4.00(t, 2H, J=6.0 Hz), 5.07(s, 2H), 6.96(d, 1H, J=8.9 Hz), 7.03(m, 2H), 7.32(m, 2H), 7.32(m, 1H), 7.38(m, 2H), 7.40(m, 1H), 7.46(m, 3H), 7.48(s, 1H), 7.63(ddd, 1H, J=1.2, 7.1, 8.3 Hz), 9.12(dd, 1H, J=1.2, 7.9 Hz).

FABMS(m/z); 534(M+1)$^+$

Example 140

Compound 148

According to Example 5, 280 mg (80%) of Compound 148 was obtained from 423 mg (0.79 mmol of Compound 147 and 120 mg of 10% Pd/C.

$^1$HNMR(DMSO-d$_6$)∂; 1.98(s, 6H), 2.35(E, 2H, J=5.6 Hz), 3.06(s, 3H), 3.88(t, 2H, J=5.6 Hz), 3.97(s, 3H), 6.79(m, 2H), 6.92(m, 1H), 7.38(dt, 1H, J=1.0, 7.8 Hz), 7.65(ddd, 1H, J=1.2, 7.1, 8.3 Hz), 7.74(d, 1H, J=8.3 Hz), 7.78(s, 1H), 8.94(d, 1H, J=7.8 Hz), 9.02(s, 1H).

FABMS(m/z); 444(M+1)$^+$

Example 141

Compound 149

To a solution of 80 mg (0.18 mmol) of Compound 148 in 6.4 ml of a mixed solvent of THF and MeOH (15/1) were added 188 ml (1.08 mmol) of diisopropylethylamine and 0.56 ml (1.08 mmol) of a 2.0M hexane solution of (trimethylsilyl)diazomethane in 3 portions at 1.5 hours intervals, followed by stirring at room temperature for 32 hours. Water was added to the reaction mixture, followed by extraction with CHCl$_3$. The extract was washed with brine, dried over Na$_2$SO$_4$, and evaporated. The residue was purified by preparative thin-layer chromatograPhY (CHCl$_3$/MeOH=10/1) to give 60 mg (78%) of Compound 149.

$^1$HNMR(CDCl$_3$)∂; 2.16(s, 6H), 2.45(t, 2H, J=5.6 Hz), 3.19(s, 3H), 3.83(s, 3H), 3.91(s, 3H), 4.05(t, 2H, J=5.6 Hz), 6.95(m, 3H), 7.40(dt, 1H, J=0.9, 7.5 Hz), 7.47(d, 1H, J=8.3 Hz), 7.50(s, 1H), 7.63(ddd, 1H, J=1.0, 7.2, 8.3 Hz), 9.11(dd, 1H, J=1.0, 7.9 Hz).

FABMS(m/z); 458(M+1)$^+$

Example 142

Compound 150

According to Example 2, 37 mg (37%) of Compound 150 was obtained from 70 mg (0.16 mmol) of Compound 148, 0.04 ml (0.38 mmol) of isopropyl bromide and 17 mg (0.42 mmol) of 60% sodium hydride.

$^1$HNMR(CDCl$_3$)∂; 1.35(d, 6H, J=6.1 Hz), 2.10(s, 6H), 2.43(t, 2H, J=5.9 Hz), 3.19(s, 3H), 3.90(s, 3H), 3.99(t, 2H, J=5.9 Hz), 4.49(m, 1H), 6.94(m, 3H), 7.40(ddd, 1H, J=0.9, 7.2, 8.0 Hz), 7.46(d, 1H, J=8.3 Hz), 7.50(s, 1H), 7.62(ddd, 1H, J=1.0, 7.2, 8.3 Hz, 9.12(dd, 1H, J=1.0, 8.0 Hz).

FABMS(m/z); 486(M+1)$^+$

Example 143

Compound 151

According to Example 2, 24 mg (23%) of Compound 151 was obtained from 80 mg (0.18 mmol) of Compound 148, 35 mg (0.22 mmol) of 4-chlorobenzyl chloride and 11 mg (0.27 mmol) of 60% sodium hydride.

$^1$HNMR(CDCl$_3$)∂; 2.11(s, 6H), 2.44(t, 2H, J=5.8 Hz), 3.19(s, 3H), 3.90(s, 3H), 4.00(t, 2H, J=5.8 Hz), 5.04(s, 2H), 6.98(m, 3H), 7.38(m, 5H), 7.46(d, 1H, J=8.3 Hz), 7.47(s, 1H), 7.63(ddd, 1H, J=1.2, 7.3, 8.3 Hz), 9.11(d, 1H, J=7.8 Hz).

FABMS(m/z); 568($^M$+1)$^+$

Example 144

Compound 152

According to Example 2, 30 mg (73%) of Compound 152 was obtained from 50 mg (0.11 mmol) of Compound 148, 22 mg (0.13 mmol) of 2-picolyl chloride hydrochloride and 12 mg (0.30 mmol) of 60% sodium hydride.

$^1$HNMR(CDCl$_3$)∂; 2.10(s, 6H), 2.43(t, 2H, J=6.0 Hz), 3.19(s, 3H), 3.91(s, 3H), 3.99(t, 2H, J=6.0 Hz), 5.22(s, 2H), 6.95(d, 1H, J=9.0 Hz), 7.03(dd, 1H, J=3.1, 9.0 Hz), 7.07(d, 1H, J=3.1 Hz), 7.22(m, 1H), 7.40(ddd, 1H, J=1.0, 7.3, 8.3 Hz), 7.47(d, 1H, J=8.3 Hz), 7.49(s, 1H), 7.58(d, 1H, J=7.8 Hz), 7.63(ddd, 1H, J=1.2, 7.3, 8.3 Hz), 7.72(dt, 1H, J=1.7, 7.8 Hz), 8.59(m, 1H), 9.12(m, 1H).

FABMS(m/z); 535(M+1)$^+$

Example 145

Compound 153

According to Example 2, 35 mg (75%) of Compound 153 was obtained from 50 mg (0.11 mmol) of Compound 148, 22 mg (0.13 mmol) of 4-picolyl chloride hydrochloride and 12 mg (0.30 mmol) of 60% sodium hydride.

$^1$HNMR(CDCl$_3$)∂; 2.10(s, 6H), 2.43(t, 2H, J=6.0 Hz), 3.19(s, 3H), 3.91(s, 3H), 3.99(t, 2H, J=6.0Hz), 5.10(s, 2H), 6.96(m, 3H), 7.37(m, 2H), 7.41(m, 1H), 7.46(d, 1H, J=8.3 Hz), 7.48(s, 1H), 7.63(ddd, 1H, J=1.2, 7.1, 8.3 Hz), 8.62(m, 2H), 9.11(d, 1H, J=8.1 Hz).

FABMS(m/z); 535(M+1)$^+$

Example 146

Compound 154

According to Example 2, 1 mg (2%) of Compound 154 was obtained from 50 mg (0.11 mmol) of Compound 148, 27 mg (0.12 mmol) of 2-(bromomethyl)naphthalene and 6 mg (0.15 mmol) of 60% sodium hydride.

$^1$HNMR(CDCl$_3$)∂; 2.14(s, 6H), 2.51(t, 2H, J=5.9 Hz), 3.19(s, 3H), 3.86(s, 3H), 4.04(t, 2H, J=5.9 Hz), 5.24(s, 2H), 6.97(m, 1H), 7.07(m, 2H), 7.40(m, 1H), 7.47(s, 1H), 7.47(m, 3H), 7.56(dd, 1H, J=1.7, 8.3 Hz), 7.62(ddd, 1H, J=1.2, 7.1, 8.3 Hz), 7.87(m, 4H), 9.11(d, 1H, J=7.8 Hz).

FABMS(m/z); 584(M+1)$^+$

Example 147

Compound 155

According to Example 54, 121 mg (100%) a free base of Compound 155 was obtained from 101 mg (0.23 mmol) of Compound 148, 0.10 ml (1.24 mmol) of pyridine and 0.10 ml (1.06 mmol) of acetic anhydride.

According to Example 13, 102 mg (81%) of Compound 155 was obtained from 117 mg (0.24 mmol) of the free base of Compound 155.

$^1$HNMR(DMSO-d$_6$)∂; 2.27(s, 3H), 2.55(s, 6H), 3.07(s, 3H), 3.26(m, 2H), 3.99(s, 3H), 4.32(m, 2H), 7.17(m, 1H), 7.21(m, 1H), 7.22(m, 1H), 7.39(t, 1H, d=7.6 Hz), 7.66(t, 1H, J=7.6 Hz), 7.74(d, 1H, J=7.6 Hz), 7.85(s, 1H), 8.96(d, 1H, J=7.6 Hz).

EIMS(m/z); 485(M)$^+$

Example 148

Compound 156

According to Example 54, 164 mg (92%) of a free base of Compound 156 was obtained from 150 mg (0.34 mmol) of Compound 148, 0.15 ml (1.08 mmol) of triethylamine and 0.06 ml (0.51 mmol) of valeryl chloride.

According to Example 13, 151 mg (88%) of Compound 156 was obtained from 161 mg (0.31 mmol) of the free base of Compound 156.

$^1$HNMR(DMSO-d$_6$)∂; 0.92(t, 3H, J=7.4 Hz), 1.33–1.43 (m, 2H), 1.59–1.70(m, 2H), 2.55(s, 6H), 2.57(t, 2H, J=7.9 Hz), 3.07(s, 3H), 3.26(m, 3H), 3.99(s, 3H), 4.33(m, 2H), 7.15(m, 1H), 7.20(m, 1H), 7.21(m, 1H), 7.39(t, 1H, J=7.4 Hz), 7.66(t, 1H, J=7.9 Hz), 7.74(d, 1H, J=7.9 Hz), 7.85(s, 1H), 8.96(d, 1H, J=7.4 Hz).

EIMS(m/z); 527(M)$^+$

Example 149

Compound 157

To a solution of 300 mg (0.84 mmol) of Compound 65 in 75 ml of DMF containing 20% of water was added a solution of 795 mg (1.85 mmol) of [bis(trifluoroacetoxy)iodo] benzene in 8 ml of acetonitrile containing 50% of water under an ice-cooled condition, followed by stirring at the same temperature for 2 hours. To the reaction mixture, 147 mg (0.84 mmol) of sodium hydrosulfite was added, followed by stirring at the same temperature for 1 hour. After evaporation of the solvent under reduced pressure, the resulting residue was triturated with water and then MeOH to give 261 mg (83%) of Compound 157.

$^1$HNMR(DMSO-d$_6$)∂; 3.06(s, 3H), 3.97(s, 3H), 6.67(dd, 1H, J=2.9, 8.5 Hz), 6.69(d, 1H, J=2.9 Hz), 6.73(d, 1H, J=8.5 Hz), 7.38(ddd, 1H, J=0.9, 7.2, 7.9 Hz), 7.65(ddd, 1H, J=1.1, 7.2, 8.4 Hz), 7.73(d, 1H, J=8.4 Hz), 7.75(s, 1H), 8.62(s, 1H), 8.73(s, 1H), 8.95(dd, 1H, J=1.1, 7.9 Hz).

FABMS(m/z); 373(M+1)$^+$

Example 150

Compound 158

According to Example 80, 585 mg (99%) of Compound 158 was obtained from 505 mg (1.21 mmol) of Compound 114 and 640 mg (1.33 mmol) of tetra-n-butylammonium tribromide.

$^1$HNMR(DMSO-d$_6$)∂; 3.04(s, 3H), 3.73(t, 2H, J=5.0 Hz), 3.98(s, 3H), 4.21(m, 2H), 7.11(dt, 1H, J=1.0, 7.5 Hz), 7.15(d, 1H, J=8.0 Hz), 7.42(dd, 1H, J=1.8, 7.5Hz), 7.44(ddd, 1H, J=1.8, 7.2, 8.0 Hz), 7.75(d, 1H, J=8.8 Hz), 7.79(dd, 1H, J=2.1, 8.8 Hz), 7.86(s, 1H), 9.09(d, 1H, J=2.1 Hz).

FABMS(m/z); 497(M+1)$^+$

Example 151

Compound 159

To a suspension of 585 mg (1.18 mmol) of Compound 158 in 100 ml of methylene chloride were added a solution of 1.29 ml (11.76 mmol) of titanium tetrachloride in 4 ml of methylene chloride and a solution of 1.06 ml (10.17 mmol) of dichloromethyl methyl ether in 4 ml of methylene chloride under an ice-cooled condition, followed by stirring at room temperature for 3 hours. Ice water and 0.7 ml of concentrated hydrochloric acid were added to the reaction mixture, followed by extraction with CHCl$_3$. The extract was washed with water, and evaporated. The residue was triturated with water and then MeOH to give 593 mg (96%) of Compound 159.

$^1$HNMR(DMSO-d$_6$)∂; 3.05(s, 3H), 3.77(t, 2H, J=5.0 Hz), 4.00(s, 3H), 4.34(m, 2H), 7.37(d, 1H, J=8.5 Hz), 7.76(d, 1H, J=8.7 Hz), 7.81(dd, 1H, J=2.0, 8.7 Hz), 7.96(s, 1H), 7.97(d, 1H, J=2.1 Hz), 8.05(dd, 1H, J=2.1, 8.5 Hz), 9.08(d, 1H, J=2.0 Hz), 9.98(s, 1H).

FABMS(m/z); 525(M+1)$^+$

Example 152

Compound 160

To a solution of 224 mg (0.46 mmol) of Compound 159 in 50 ml of DMF were added 1.40 g (9.34 mmol) of sodium iodide and 2.0 ml (18.68 mmol) of 50% aqueous dimethylamine solution in three portions at 1 hour intervals, followed by stirring at 100° C. for 6 hours. Water was added to the reaction mixture, followed by extraction with CHCl$_3$. The extract was washed with brine, dried over Na$_2$SO$_4$, and evaporated. The residue was purified by silica gel column chromatography (CHCl$_3$) to give 165 mg (67%) of Compound 160 .

$^1$HNMR(CDCl$_3$)∂; 2.12(s, 6H), 2.50(t, 2H, J=5.9 Hz), 3.19(s, 3H), 3.92(s, 3H), 4.16(t, 2H, J=5.9 Hz), 7.13(d, 1H, J=8.5 Hz), 7.36(d, 1H, J=8.7 Hz), 7.51(s, 1H), 7.72(dd, 1H, J=2.0, 8.7 Hz), 7.93(d, 1H, J=2.2 Hz), 7.97(dd, 1H, J=2.2, 8.5 Hz), 9.27(d, 1H, J=2.0 Hz), 9.97(s, 1H).

FABMS(m/z); 534(M+1)$^+$

Example 153

Compound 161

To a solution of 300 mg (0.56 mmol) of Compound 160 in 15 ml of DMF were added 90 mg (0.58 mmol) of tetrakis(triphenylphosphine)palladium and 67 mg (0.68 mmol) of potassium acetate, followed by stirring in a stream of hydrogen at 100° C. for 3 hours. Ice water was added to the reaction mixture, followed by extraction with CHCl$_3$. The extract was washed with brine, dried over Na$_2$SO$_4$, and evaporated. The residue was purified by silica gel column chromatography (CHCl$_3$MeOH=30/1) to give 214 mg (84%) of Compound 161.

$^1$HNMR(CDCl$_3$)∂; 2.12(s, 6H), 2.50(t, 2H, J=5.7 Hz), 3.19(s, 3H), 3.94(s, 3H), 4.17(t, 2H, J=5.7 Hz), 7.13(d, 1H, J=8.5 Hz), 7.42(ddd, 1H, J=0.9, 7.3, 8.0 Hz), 7.49(d, 1H, J=8.3 Hz), 7.50(s, 1H), 7.65(ddd, 1H, J=1.1, 7.3, 8.3 Hz), 7.93(d, 1H, J=2.2 Hz), 7.97(dd, 1H, J=2.2, 8.5 Hz), 9.12(dd, 1H, J=1.1, 8.0 Hz), 9.97(s, 1H).

FABMS(m/z); 456(M+1)$^+$

Example 154

Compound 162

According to Example 66, 95 mg (99%) of Compound 162 was obtained from 100 mg (0.23 mmol) of Compound 141, 0.033 ml (0.28 mmol) of benzyl bromide and 48 mg (0.35 mmol) of potassium carbonate.

1HNMR(CDCl$_3$)∂; 3.09(s, 3H), 3.85(s, 3H), 5.06(s, 2H), 7.11(d, 1H, J=7.9 Hz), 7.13–7.28(m, 6H), 7.31(d, 1H, J=8.7 Hz), 7.39(dd, 1H, J=1.7, 7.8 Hz), 7.45(ddd, 1H, J=1.7, 7.6, 7.9 Hz), 7.49(s, 1H), 7.69(dd, 1H, J=1.7, 8.7 Hz), 9.25(d, 1H, J=1.7 Hz).

FABMS(m/z); 525(M+1)$^+$

Example 155

Compound 163

To a suspension of 25 mg (0.19 mmol) of aluminum chloride in 0.5 ml of methylene chloride was added 0.014 ml (0.19 mmol) of acetyl chloride at −78° C., followed by stirring for 20 minutes. At the same temperature, a solution of 20 mg (0.04 mmol) of Compound 62 in 0.5 ml of methylene chloride was added thereto, followed by stirring at −10° C. for 35 minutes. Ice water was added to the reaction mixture, followed by extraction with CHCl$_3$. The extract was washed with brine, dried over Na$_2$SO$_4$, and evaporated. The residue was purified by preparative thin-layer chromatography (toluene/AcOEt=4/1) to give 7 mg (37%) of Compound 163.

¹HNMR(CDCl₃)∂; 1.93(s, 3H), 2.65(s, 3H), 3.20(s, 3H), 3.91(s, 3H), 7.37(d, 1H, J=8.7 Hz), 7.38(d, 1H, J=8.2 Hz), 7.47(s, 1H), 7.74(dd, 1H, J=2.1, 8.7 Hz), 8.09(d, 1H, J=2.1 Hz), 8.11(dd, 1H, J=2.1, 8.2 Hz), 9.25(d, 1H, J=2.1 Hz).

FABMS(m/z); 519(M+1)⁺

Example 156

Compound 164

According to Example 155, 0.24 g (27%) of Compound 164 was obtained from 2.15 g (16.13 mmol) of aluminum chloride, 0.58 ml (8.16 mmol) of acetyl chloride and 0.83 g (1.64 mmol) of Compound 142.

¹HNMR(CDCl₃)∂; 2.13(s, 6H), 2.51(t, 2H, J=5.9 Hz), 2.61(s, 3H), 3.18(s, 3H), 3.91(s, 3H), 4.15(t, 2H, J=5.9 Hz), 7.05(d, 1H, J=8.8 Hz), 7.34(d, 1H, J=8.7 Hz), 7.50(s, 1H), 7.71(dd, 1H, J=2.0, 8.7 Hz), 8.02(d, 1H, J=2.3 Hz), 8.07(dd, 1H, J=2.3, 8.8 Hz , 9.25(m, 1H).

FABMS(m/z); 548(M+1)⁺

Example 157

Compound 165 and Compound 166

According to Example 76, 1.15 g (68%) of Compound 165 and 0.28 g (17%) of Compound 166 were obtained from 1.50 g (4.21 mmol) of Compound 65 and 3.60 ml (85.14 mmol) of fuming nitric acid.

Compound 165

¹HNMR(DMSO-d₆)∂; 3.02(s, 3H), 3.94(s, 3H), 6.11(br s, 1H), 7.14(d, 1H, J=9.8 Hz), 7.43(dt, 1H, J=0.8, 7.9 Hz), 7.47(d, 1H, J=8.3 Hz), 7.52(s, 1H), 7.67(ddd, 1H, J=1.2, 7.2, 8.3 Hz), 8.29(d, 1H, J=2.6 Hz), 8.29(dd, 1H, J=2.6, 9.8 Hz), 9.04(d, 1H, J=7.9 Hz).

FABMS(m/z); 402(M+1)⁺

Compound 166

¹HNMR(DMSO-d₆)∂; 3.20(s, 3H), 3.94(s, 3H), 7.73(dd, 1H, J=7.4, 8.6 Hz), 7.42(ddd 1H, J=0.9, 7.3, 8.0 Hz), 7.48(d, 1H, J=8.3 Hz), 7.52(s, 1H), 7.65(ddd, 1H, J=1.2, 7.3, 8.3 Hz), 7.70(dd, 1H, J=1.7, 7.4 Hz), 8.26(dd, 1H, J=1.7, 8.6 Hz), 9.12(ddd, 1H, J=0.7, 1.2, 8.0 Hz), 11.00(s, 1H).

FABMS(m/z); 402(M+1)⁺

Example 158

Compound 167

According to Example 2, 578 mg (59%) of Compound 167 was obtained from 844 mg (2.10 mmol) of Compound 165, 132 mg (3.30 mmol) of 60% sodium hydride and 0.76 ml (4.19 mmol) of 2-chloroethyl p-toluenesulfonate.

¹HNMR(DMSO-d₆)∂; 3.04(s, 3H), 3.78(t, 2H, J=4.9 Hz), 4.01(s, 3H), 4.39(m, 2H), 7.39(d, 1H, J=9.3 Hz), 7.41(ddd, 1H, J=1.0, 7.1, 8.0 Hz), 7.68(ddd, 1H, J=1.2, 7.1, 8.3 Hz), 7.77(d, 1H, J=8.3 Hz), 7.98(s, 1H), 8.32(d, 1H, J=2.7 Hz), 8.39(dd, 1H, J=2.7, 9.3 Hz), 8.95(d, 1H, J=8.0 Hz).

FABMS(m/z); 464(M+1)⁺

Example 159

Compound 168

According to Example 2, 22 mg (37%) of Compound 168 was obtained from 50 mg (0.13 mmol) of Compound 165, 36 mg (0.25 mmol) of 2-dimethylaminoethyl chloride hydrochloride and 69 mg (0.50 mmol) of potassium carbonate.

¹HNMR(CDCl₃)∂; 2.13(s, 6H), 2.52(t, 2H, J=5.9 Hz), 3.21(s, 3H), 3.97(s, 3H), 4.18(t, 2H, J=5.9 Hz), 7.09(d, 1H, J=9.0 Hz), 7.45(ddd, 1H, J=1.0, 7.2, 8.1 Hz), 7.51(s, 1H), 7.51(d, 1H, J=8.3 Hz), 7.68(ddd, 1H, J=1.2, 7.2, 8.3 Hz), 8.32(d, 1H, g=2.9 Hz), 8.38(dd, 1H, J=2.9, 9.0 Hz), 9.14 (ddd, 1H, J=0.7, 1.2, 8.1 Hz).

FABMS(m/z); 473(M+1)⁺

Example 160

Compound 169

According to Example 5, 1.36 g (92%) of Compound 169 was obtained from 1.58 g (3.34 mmol) of Compound 168 and 0.5 g of 10% Pd/C.

¹HNMR(CDCl₃)∂; 2.09(s, 6H), 2.40(t, 2H, J=6.1 Hz), 3.19(s, 3H), 3.50(br, 2H), 3.90(s, 3H), 3.94(t, 2H, J=6.1 Hz), 6.77(m, 2H), 6.88(m, 1H), 7.40(ddd, 1H, J=1.0, 7.2, 8.1 Hz), 7.46(d, 1H, J=8.4 Hz), 7.50(s, 1H), 7.62(ddd, 1H, J=1.2, 7.2, 8.4 Hz), 9.11(ddd, 1H, J=0.7, 1.2, 8.1 Hz).

FABMS(m/z); 443(M+1)⁺

Example 161

Compound 170

According to Example 6, 66 mg (45%) of Compound 170 was obtained from 135 mg (0.31 mmol) of Compound 169, 0.25 ml (3.10 mmol) of 35% formalin and 657 mg (3.10 mmol) of sodium triacetoxyborohydride.

¹HNMR(CDCl₃)∂; 2.12(s, 6H), 2.45(m, 2H), 2.92(s, 6H), 3.19(s, 3H), 3.91(s, 3H), 3.98(t, 2H, J=5.9 Hz), 6.82(m, 1H), 6.83(m, 1H), 6.96(dd, 1H, J=1.0, 8.3 Hz), 7.40(dt, 1H, J=0.7, 8.0 Hz), 7.46(d, 1H, J=8.2 Hz), 7.53(s, 1H), 7.62(ddd, 1H, J=1.2, 7.3, 8.2 Hz), 9.12(d, 1H, J=8.1 Hz).

FABMS(m/z); 471(M+1)⁺

Example 162

Compound 171

According to Example 54, 93 mg (91%) of Compound 171 was obtained from 100 mg (0.23 mmol) of Compound 169, 0.033 ml (0.46 mmol) of triethylamine and 0.032 ml (0.34 mmol) of acetic anhydride.

¹HNMR(CDCl₃)∂; 2.10(s, 6H), 2.16(s, 3H), 2.44(t, 2H, J=6.0 Hz), 3.18(s, 3H), 3.88(s, 3H), 4.03(t, 2H, J=6.0 Hz), 6.97(d, 1H, J=8.8 Hz), 7.16(s, 1H), 7.40(t, 1H, J=7.5 Hz), 7.44(d, 1H, J=8.3 Hz), 7.50(m, 2H), 7.50(s, 1H), 7.62(ddd, 1H, J=1.2, 7.1, 8.3 Hz), 9.10(d, 1H, J=7.8 Hz).

FABMS(m/z); 485(M+1)⁺

Example 163

Compound 172

According to Example 54, 51 mg (75%) of Compound 172 was obtained from 55 mg (0.12 mmol) of Compound 169, 0.018 ml (0.24 mmol) of triethylamine and 0.022 ml (0.19 mmol) of benzoyl chloride.

¹HNMR(DMSO-d₆)∂; 2.01(s, 6H), 2.37(t, 2H, J=5.7 Hz), 3.08(s, 3H), 4.00(s, 3H), 4.00(m, 2H), 7.12(d, 1H, J=8.7 Hz), 7.40(m, 1H), 7.55(m, 3H), 7.67(ddd, 1H, J=1.2, 7.1, 8.3 Hz), 7.76(d, 1H, J=8.3 Hz), 7.82(m, 2H), 7.83(s, 1H), 7.98(m, 2H), 8.96(d, 1H, J=7.6 Hz), 10.22(s, 1H).

FABMS(m/z); 547(M+1)⁺

Example 164

Compound 173 and Compound 174

According to Example 151, 2.45(76%) of Compound 173 was obtained from 3.00 g (7.51 mmol) of Compound 101, 4.30 ml (39.22 mmol) of titanium tetrachloride and 1.78 ml (19.68 mmol) of dichloromethyl methyl ether.

FABMS(m/z); 427(M+1)⁺

According to Example 118, 2.00 g (91%) of Compound 174 was obtained from 2.45 g (5.75 mmol) of Compound 173 and 0.95 g (6.87 mmol) of potassium carbonate.

¹HNMR(DMSO-d₆)∂; 3.08(s, 3H), 4.03(s, 3H), 6.91(dt, 1H, J=1.0, 7.5 Hz), 6.95(dd, 1H, J=1.0, 8.1 Hz), 7.27(ddd, 1H, J=1.7, 7.5, 8.1 Hz), 7.29(dt, 1H, J=1.7, 7.5 Hz), 7.88(s, 1H), 7.90(d, 1H, J=8.6 Hz), 8.16(dd, 1H, J=1.6, 8.6 Hz), 9.45(d, 1H, J=1.6 Hz), 10.14(s, 1H).

FABMS(m/z); 385(M+1)⁺

Example 165

Compound 175

According to Example 2, 1.91 g (41%) of Compound 175 was obtained from 4.00 g (10.41 mmol) of Compound 174, 0.47 g (11.75 mmol) of 60% sodium hydride and 2.45 ml (13.51 mmol) of 2-chloroethyl p-toluenesulfonate.

¹HNMR(DMSO-d₆)∂; 3.04(s, 3H), 3.73(t, 2H, J=4.8 Hz), 4.00(s, 3H), 4.21(m, 2H), 7.12(t, 1H, J=7.9 Hz), 7.15(d, 1H, J=7.9 Hz), 7.45(m, 2H), 7.88(d, 1H, J=8.3 Hz), 7.91(s, 1H), 8.14(m, 1H), 9.38(s, 1H), 10.11(s, 1H).

FABMS(m/z); 447(M+1)⁺

Example 166

Compound 176

According to Example 109, 1.08 g (89%) of Compound 176 was obtained from 1.00 g (2.24 mmol) of Compound 175 and 7.44 g (44.80 mmol) of potassium iodide.

¹HNMR(DMSO-d₆)∂; 3.08(s, 3H), 3.31(m, 2H), 4.05(s, 3H), 4.22(m, 2H), 7.11(dt, 1H, J=0.7, 7.4 Hz), 7.13(d, 1H, J=8.1 Hz), 7.43(m, 2H), 7.92(d, 1H, J=8.8 Hz), 7.93(s, 1H), 8.17(dd, 1H, J=1.5, 8.8 Hz), 9.45(d, 1H, J=1.5 Hz), 10.14(s, 1H).

FABMS(m/z); 539(M+1)⁺

Example 167

Compound 177

According to Example 2, 0.50 g (25%) of Compound 177 was obtained from 1.67 g (4.33 mmol) of Compound 174, 1.25 g (8.68 mmol) of 2-dimethylaminoethyl chloride hydrochloride and 2.42 g (17.48 mmol) of potassium carbonate.

¹HNMR(CDCl₃)∂; 2.13(s, 6H), 2.48(t, 2H, J=6.0 Hz), 3.21(s, 3H), 3.97(s, 3H), 4.08(t, 2H, J=6.0 Hz), 7.04(dd, 1H, J=0.9, 8.3 Hz), 7.10(dt, 1H, J=0.9, 7.6 Hz), 7.37(dd, 1H, J=1.7, 7.6 Hz), 7.45(ddd, 1H, J=1.7, 7.6, 8.3 Hz), 7.56(d, 1H, J=8.7 Hz), 7.59(s, 1H), 8.23(dd, 1H, J=1.5, 8.7 Hz), 9.58(d, 1H, J=1.5 Hz), 10.22(s, 1H).

FABMS(m/z); 456(M+1)⁺

Example 168

Compound 178

According to Example 155, 372 mg (67%) of Compound 178 was obtained from 500 mg (1.26 mmol) of Compound 101, 836 mg (6.27 mmol) of aluminum chloride add 0.45 ml (6.27 mmol) of acetyl chloride.

¹HNMR(CDCl₃)∂; 1.91(s, 3H), 2.84(s, 3H), 3.23(s, 3H), 3.95(s, 3H), 7.26(dd, 1H, J=1.2, 8.1 Hz), 7.40(dt, 1H, J=1.2, 7.6 Hz), 7.46(dd, 1H, J=1.7, 7.6 Hz), 7.52(s, 1H), 7.53(m, 2H), 8.35(dd, 1H, J=1.5, 8.7 Hz), 9.77(d, 1H, J=1.5 Hz).

FABMS(m/z); 441(M+1)⁺

Example 169

Compound 179

According to Example 118, 33? mg (100%) of Compound 179 was obtained from 372 mg (0.84 mmol) of Compound 178 and 140 mg (1.01 mmol) of potassium carbonate.

¹HNMR(DMSO-d₆)∂; 2.72(s, 3H), 3.08(s, 3H), 4.01(s, 3H), 6.91(t, 1H, J=7.3 Hz), 6.94(d, 1H, J=8.3 Hz), 7.28(m, 2H), 7.81(d, 1H, J=8.8 Hz), 7.85(s, 1H), 8.24(dd, 1H, J=1.7, 8.8 Hz), 9.44(s, 1H), 9.60(d, 1H, J=1.7 Hz).

FABMS(m/z); 399(M+1)⁺

Example 170

Compound 180

According to Example 45, 98 mg (52%) of Compound 180 was obtained from 160 mg (0.40 mmol) of Compound 179, 116 mg (0.81 mmol) of 2-dimethylaminoethyl chloride hydrochloride and 222 mg (1.61 mmol) of potassium carbonate.

¹HNMR(CDCl₃)∂; 2.12(s, 6H), 2.48(t, 2H, J=5.9 Hz), 2.84(s, 3H), 3.21(s, 3H), 3.95(s, 3H), 4.08(t, 2H, J=5.9 Hz), 7.03(d, 1H, J=8.2 Hz), 7.01(dt, 1H, J=1.0, 7.5 Hz), 7.37(dd, 1H, J=1.7, 7.6 Hz), 7.44(ddd, 1H, J=1.7, 7.3, 8.2 Hz), 7.50(d, 1H, J=8.6 Hz), 7.57(s, 1H), 8.34(dd, 1H, J=1.5, 8.6 Hz), 9.77(d, 1H, J=1.5 Hz).

FABMS(m/z); 470(M+1)⁺

Example 171

Compound 181 and Compound 182

According to Example 76, 0.49 g (44%) of Compound 181 and 0.07 g (6%) of Compound 182 were obtained from 1.00 g (2.51 mmol of Compound 101 and 0.18 ml (4.14 mmol) of fuming nitric acid.

Compound 181

¹HNMR(CDCl₃)∂; 1.92(s, 3H), 3.23(s, 3H), 3.98(s, 3H), 7.27(m, 1H), 7.41(t, 1H, J=7.6 Hz), 7.46(dd, 1H, J=1.6, 7.6 Hz), 7.52(d, 1H, J=9.1 Hz), 7.54(ddd, 1H, J=1.6, 7.6, 8.3 Hz), 7.56(s, 1H), 8.54(dd, 1H, J=2.1, 9.1 Hz), 10.01(d, 1H, J=2.1 Hz).

FABMS(m/z); 444(M+1)⁺

Compound 182

¹HNMR(CDCl₃)∂; 1.92(s, 3H), 3.22(s, 3H), 3.90(s, 3H), 7.27(m, 1H), 7.37–7.58(m, 4H), 7.61(s, 1H), 8.13(dd, 1H, J=1.2, 7.9 Hz), 9.49(dd, 1H, J=1.2, 7.9 Hz).

FABMS(m/z); 444(M+1)⁺

Example 172

Compound 183

To a solution of 460 mg (1.04 mmol) of Compound 181 in 46 ml of dioxane was added 4.6 ml of 1N hydrochloric acid, followed by stirring at 100° C. for 7.5 hours. Water and then an aqueous saturated sodium hydrogencarbonate solution were added to the reaction mixture. The resulting precipitate was collected by filtration, washed with water and then MeOH, and dried under reduced pressure to give 416 mg (100%) of Compound 183.

¹HNMR(DMSO-d₆)∂; 3.09(s, 3H), 4.06(s, 3H), 6.92(t, 1H, J=7.3 Hz), 6.95(d, 1H, J=8.1 Hz), 7.29(m, 2H), 7.92(s, 1H), 7.92(d, 1H, J=9.0 Hz), 8.51(dd, 1H, J=2.4, 9.0 Hz), 9.82(d, 1H, J=2.4 Hz).

FABMS(m/z); 402(M+1)⁺

Example 173

Compound 184

According to Example 45, 349 mg (69%) of a free base of Compound 184 was obtained from 430 mg (1.07 mmol) of Compound 183, 301 mg (2.09 mmol) of 2-dimethylaminoethyl chloride hydrochloride and 591 mg (4.28 mmol) of potassium carbonate.

According to Example 13, 47 mg (87%) of Compound 184 was obtained from 50 mg (0.11 mmol) of the free base of Compound 184.

$^1$HNMR(DMSO-d$_6$)∂; 2.57(s, 6H), 3.09(s, 3H), 3.27(m, 2H), 4.07(s, 3H), 4.32(m, 2H), 7.15(t, 1H, J=7.5 Hz), 7.22(d, 1H, J=8.3 Hz), 7.42(dd, 1H, J=1.7, 7.5 Hz), 7.50(ddd, 1H, J=1.7, 7.5, 8.3 Hz), 7.97(d, 1H, J=9.2 Hz), 8.01(s, 1H), 8.54(dd, 1H, J=2.4, 9.2 Hz), 9.83(d, 1H, J=2.4 Hz), 9.93(br, 1H).

FABMS(m/z); 473(M+1)$^+$

Example 174

Compound 185

According to Example 5, 239 mg (75%) of a free base of Compound 185 was obtained from 290 mg (0.72 mmol) of a free base of Compound 184 and 200 mg of 10% Pd/C.

According to Example 13, 57 mg (99%) of Compound 185 was obtained from 50 mg (0.12 mmol) of the free base of Compound 185.

$^1$HNMR(DMSO-d$_6$)∂; 2.55(s, 6H), 3.07(s, 3H), 3.26(m, 2H), 4.01(s, 3H), 4.33(m, 2H), 7.13(t, 1H, J=7.5 Hz), 7.20(d, 1H, J=8.3 Hz), 7.39(m, 1H), 7.49(m, 1H), 7.64(m, 1H), 7.86(d, 1H, J=8.9 Hz), 7.91(s, 1H), 8.94(m, 1H), 10.26(m, 3H).

FABMS(m/z); 443(M+1)$^+$

Example 175

Compound 186

According to Example 6, 56 mg (66%) of a free base of Compound 186 was obtained from 80 mg (0.19 mmol) of a free base of Compound 185, 0.16 ml (1.97 mmol) of 35% formalin and 117 mg (1.86 mmol) of sodium cyanoborohydride.

According to Example 13, 40 mg (77%) of Compound 186 was obtained from 45 mg (0.10 mmol) of the free base of Compound 186.

$^1$HNMR(DMSO-d$_6$)∂; 2.51(s, 6H), 3.07(s, 3H), 3.20(m, 2H), 3.21(s, 6H), 4.00(s, 3H), 4.33(m, 2H), 7.13(:, 1H, J=7.4. Hz), 7.19(d, 1H, J=8.6 Hz), 7.39(dd, 1H, J=1.3, 7.4 Hz), 7.48(m, 1H), 7.88(m, 3H), 8.99(m, 1H), 10.31(m, 1H).

FABMS(m/z); 471(M+1)$^+$

Example 176

Compound 187

According no Example 54, 64 mg (83%) of a free base of Compound 187 was obtained from 70 mg (0.16 mmol) of a free base of Compound 185, 0.024 ml (0.33 mmol) of triethylamine and 0.023 ml (0.24 mmol) of acetic anhydride.

According to Example 13, 54 mg (100%) of Compound 187 was obtained from 50 mg (0.11 mmol) of the free base of Compound 187.

$^1$HNMR(DMSO-d$_6$)∂; 2.06(s, 3H), 2.52(s, 6H), 3.01(s, 3H), 3.23(m, 2H), 3.97(s, 3H), 4.27(m, 2H), 7.09(t, 1H, J=7.5 Hz), 7.15(d, 1H, J=8.3 Hz), 7.35(dd, 1H, J=1.5, 7.5 Hz), 7.44(m, 1H), 7.63(d, 1H, J=9.0 Hz), 7.76(s, 1H), 7.89(dd, 1H, J=2.2, 9.0 Hz), 9.09(d, 1H, J=2.2 Hz), 9.86(br, 1H), 10.11(s, 1H).

FABMS(m/z); 485(M+1)$^+$

Example 177

Compound 188

According to Example 54, 95 mg (96%) of a free base of Compound 188 was obtained from 85 mg (0.20 mmol) of a free base of Compound 185, 0.029 ml (0.40 mmol) of triethylamine and 0.034 ml (0.29 mmol) of benzoyl chloride.

According to Example 13, 61 mg (65%) of Compound 188 was obtained from 85 mg (0.16 mmol) of the free base of Compound 188.

$^1$HNMR(DMSO-d$_6$)∂; 2.57(s, 6H), 3.07(s, 3H), 3.28(m, 2H), 3.99(s, 3H), 4.30 m, 2H), 7.14(dt, 1H, J=1.0, 7.6 Hz), 7.20(d, 1H, J=8.0 Hz), 7.40(dd, 1H, J=1.7, 7.6 Hz), 7.48 (ddd, 1H, J1.7, 7.3, 8.0 Hz), 7.58(m, 3H), 7.74(d, 1H, J=8.8 Hz), 7.81(s, 1H), 7.99(dd, 1H, J=2.2, 8.8 Hz), 8.05(m, 2H), 9.38(d, 1H, J=2.2 Hz), 10.47(s, 1H).

FABMS(m/z); 547(M+1)$^+$

Example 178

Compound 189

According no Example 69, 1.60 g (97%) of Compound 189 was obtained from 1.60 g (3.58 mmol) of Compound 175, 1.04 g (12.32 mmol) of sodium hydrogencarbonate and 1.80 g (8.34 mmol) of 55% m-chloroperbenzoic acid.

$^1$HNMR(CDCl$_3$)∂; 3.17(s, 3H), 3.61(t,.2H, J=5.5 Hz), 3.91(s, 3H), 4.24(t, 2H, J=5.5 Hz), 7.01(d, 1H, J=8.3 Hz), 7.13(dt, 1H, J=1.0, 7.4 Hz), 7.36–7.49(m, 4H), 7.57(s, 1H), 8.44(s, 1H), 8.90(d, 1H, J=2.3 Hz).

FABMS(m/z); 463(M+1)$^+$

Example 179

Compound 190

According to Example 152, 1.24 g (83%) of a free base of Compound 190 was obtained from 1.57 g (3.39 mmol) of Compound 189, 1.02 g (6.78 mmol) of sodium iodide and 6.12 ml (67.80 mmol) of 50% aqueous dimethylamine solution.

According to Example 13, 104 mg (94%) of Compound 190 was obtained from 100 mg (0.23 mmol) of the free base of Compound 190.

$^1$HNMR(DMSO-d$_6$)∂; 2.57(s, 6H), 3.05(s, 3H), 3.28(m, 2H), 3.91(s, 3H), 4.29(m, 2H), 7.12(dt, 1H, J=1.0, 7.5 Hz), 7.15(dd, 1H, J=2.5, 8.6 Hz), 7.18(d, 1H, J=8.0 Hz), 7.37(dd, 1H, J=1.7, 7.6 Hz), 7.47(ddd, 1H, J=1.7, 7.3, 8.0 Hz), 7.54(d, 1H, J=8.6 Hz), 7.72(s, 1H), 8.39(d, 1H, J=2.5 Hz), 9.33(s, 1H), 9.63(br, 1H).

FABMS(m/z); 444(M+1)$^+$

Example 180

Compound 191

According to Example 141, 28 mg (38%) of a free base of Compound 191 was obtained from 70 mg (0.16 mmol) of a free base of Compound 190, 1.40 ml (8.01 mmol) of diisopropylethylamine and 4.00 ml (8.01 mmol) of a 2.0M hexane solution of (trimethylsilyl)diazomethane.

According to Example 13, 63 mg (98%) of Compound 191 was obtained from 60 mg (0.13 mmol) of the free base of Compound 191.

$^1$HNMR(DMSO-d$_6$)∂; 2.51(s, 6H), 3.06(s, 3H), 3.27(m, 2H), 3.91(s, 3H), 3.95(s, 3H), 4.30(m, 2H), 7.13(t, 1H, J=7.6

Hz), 7.19(d, 1H, J=8.3 Hz), 7.31(dd, 1H, J=2.7, 9.0 Hz), 7.39(dd, 1H, J=1.7, 7.6 Hz), 7.47(m, 1H), 7.68(d, 1H, J=9.0 Hz), 7.78(s, 1H), 8.54(d, 1H, J=2.7 Hz), 9.86(br, 1H).

FABMS(m/z); 458(M+1)$^+$

Example 181

Compound 192

According to Example 2, 95 mg (55%) of a free base of Compound 192 was obtained from 160 mg (0.36 mmol) of a free base of Compound 190, 0.065 ml (0.68 mmol) of isopropyl bromide and 33 mg (0.85 mmol) of 60% sodium hydride.

According to Example 13, 77 mg (78%) of Compound 192 was obtained from 90 mg (0.19 mmol) of the free base of Compound 192.

$^1$HNMR(DMSO-d$_6$)∂; 1.37(d, 6H, J=5.9 Hz), 2.57(s, 6H), 3.05(s, 3H), 3.27(m, 2H), 3.94(s, 3H), 4.30(m, 2H), 4.67(m, 1H), 7.13(t, 1H, J=7.6 Hz), 7.19(d, 1H, J=8.1 Hz), 7.29(dd, 1H, J=2.4, 9.0 Hz), 7.38(dd, 1H, J=1.7, 7.6 Hz), 7.47(m, 1H), 7.65(d, 1H, J=9.0 Hz), 7.77(s, 1H), 8.54(d, 1H, J=2.4 Hz), 9.73(br, 1H).

FABMS(m/z); 486(M+1)$^+$

Example 182

Compound 193

According to Example 2, 68 mg (40%) of a free base of Compound 193 was obtained from 140 mg (0.32 mmol) of a free base of Compound 190, 0.057 ml (0.48 mmol) of benzyl bromide and 20 mg (0.51 mmol) of 60% sodium hydride.

According to Example 13, 58 mg (92%) of Compound 193 was obtained from 60 mg (0.11 mmol) of the free base of Compound 193.

$^1$HNMR(DMSO-d$_6$)∂; 2.57(s, 6H), 3.06(s, 3H), 3.27(m, 2H), 3.95(s, 3H), 4.29(m, 2H), 5.25(s, 2H), 7.13(t, 1H, J=7.5 Hz), 7.19(d, 1H, J=8.1 Hz), 7.33–7.49(m, 6H), 7.56(m, 2H), 7.69(d, 1H, J=9.0 Hz), 7.78(s, 1H), 8.62(d, 1H, J=2.7 Hz), 9.65(br, 1H).

FABMS(m/z); 534(M+1)$^+$

Example 183

Compound 194

According to Example 54, 65 mg (74%) of a free base of Compound 194 was obtained from 80 mg (0.18 mmol) of a free base of Compound 190, 0.066 ml (0.92 mmol) of triethylamine and 0.064 ml (0.54 mmol) of acetic anhydride.

According to Example 13, 54 mg (86%) of Compound 194 was obtained from 60 mg (0.12 mmol) of the free base of Compound 194.

$^1$HNMR(DMSO-d$_6$)∂; 2.37(s, 3H), 2.57(s, 6H), 3.04(s, 3H), 3.26(m, 2H), 3.99(s, 3H), 4.30(m, 2H), 7.14(t, 1H, J=7.3 Hz), 7.20(d, 1H, J=7.8 Hz), 7.40(dd, 1H, J=1.7, 7.3 Hz), 7.45(dd, 1H, J=2.2, 8.9 Hz), 7.48(m, 1H), 7.78(d, 1H, J=8.9 Hz), 7.86(s, 1H), 8.64(d, 1H, J=2.2 Hz), 9.69(br, 1H).

FABMS(m/z); 486(M+1)$^+$

Example 184

Compound 195

According to Example 54, 56 mg (62%) of a free base of Compound 195 was obtained from 80 mg (0.18 mmol) of a free base of Compound 190, 0.050 ml (0.36 mmol) of triethylamine and 0.023 ml (0.27 mmol) of propionyl chloride.

According to Example 13, 43 mg (81%) of Compound 195 was obtained from 50 mg (0.10 mmol) of the free base of Compound 195.

$^1$HNMR(DMSO-d$_6$)∂; 1.21(t, 3H, J=7.5 Hz), 2.56(s, 6H), 2.71(q, 2H, J=7.5 Hz), 3.05(s, 3H), 3.26(m, 2H), 3.99(s, 3H), 4.3t(m, 2H), 7.13(t, 1H, J=7.5 Hz), 7.19(d, 1H, J=8.3 Hz), 7.40(dd, 1H, J=1.7, 7.5 Hz), 7.44(dd, 1H, J=2.4, 9.0 Hz), 7.48(m, 1H), 7.78(d, 1H, J=9.0 Hz), 7.86(s, 1H), 8.63(d, 1H, J=2.4 Hz), 9.89(br, 1H).

FABMS(m/z); 500(M+1)$^+$

Example 185

Compound 196

According to Example 54, 58 mg (61%) of a free base of Compound 196 was obtained from 80 mg (0.18 mmol) of a free base of Compound 190, 0.050 ml (0.36 mmol) of triethylamine and 0.032 ml (0.27 mmol) of valeryl chloride.

According to Example 13, 44 mg (77%) of Compound 196 was obtained from 55 mg (0.10 mmol) of the free base of Compound 196.

$^1$HNMR(DMSO-d$_6$)∂; 0.97(t, 3H, J=7.4 Hz), 1.45(m, 2H), 1.70(quint, 2H, J=7.5 Hz), 2.55(s, 6H), 2.68(t, 2H, J=7.5 Hz), 3.05(s, 3H), 3.26(m, 2H), 3.99(s, 3H), 4.31(m, 2H), 7.13(t, 1H, J=7.5 Hz), 7.19(d, 1H, J=8.4 Hz), 7.40(dd, 1H, J=1.7, 7.5 Hz), 7.43(dd, 1H, J=2.4, 8.9 Hz), 7.48(ddd, 1H, J=1.7, 7.5, 8.4 Hz), 7.78(d, 1H, J=8.9 Hz), 7.86(s, 1H), 8.62(d, 1H, J=2.4 Hz), 9.91(br, 1H).

FABMS(m/z); 528(M+1)$^+$

Example 186

Compound 197

According to Example 54, 73 mg (74%) of a free base of Compound 197 was obtained from 80 mg (0.18 mmol) of a free base of Compound 190, 0.033 ml (0.46 mmol) of triethylamine and 0.031 ml (0.27 mmol) of benzoyl chloride.

According to Example 13, 48 mg (69%) of Compound 197 was obtained from 65 mg (0.12 mmol) of the free base of Compound 197.

$^1$HNMR(DMSO-d$_6$)∂; 2.58(s, 6H), 3.04(s, 3H), 3.27(m, 2H), 4.03(s, 3H), 4.31(m, 2H), 7.14(t, 1H, J=7.5 Hz), 7.20(d, 1H, J=8.0 Hz), 7.41(dd, 1H, J=1.7, 7.6 Hz), 7.49(ddd, 1H, J=1.7, 7.3, 8.0 Hz), 7.62(dd, 1H, J=2.5, 8.9 Hz), 7.67(m, 2H), 7.80(m, 1H), 7.85(d, 1H, J=8.9 Hz), 7.88(s, 1H), 8.23(m, 2H), 8.77(dd, 1H, J=0.5, 2.5 Hz), 9.67(br, 1H).

FABMS(m/z); 548(M+1)$^+$

Example 187

Compound 198

According to Example 96, 1.32 g (97%) of a 1,2,3,4-tetrahydro compound of Compound 198 was obtained from 0.96 g (3.61 mmol) of 2-[2-(3-fluoro-2-hydroxyphenyl)vinyl]-1-methylindole and 1.20 g (10.8 mmol) of N-methylmaleimide. Then, 1.00 g (79%) of Compound 198 was obtained from 1.28 g (3.39 mmol) of the 1,2,3,4-tetrahydro compound of Compound 198 and 1.67 g (6.77 mmol) of DDQ.

$^1$HNMR(DMSO-d$_6$)∂; 3.06(s, 3H), 3.97(s, 3H), 6.91(dt, 1H, J=5.0, 7.9 Hz), 7.13(d, 1H, J=7.6 Hz), 7.25(ddd, 1H, J=1.7, 8.3, 10.9 Hz), 7.39(t, 1H, J=6.9 Hz), 7.64(dt, 1H, J=8.3, 1.3 Hz), 7.74(d, 1H, J=8.3 Hz), 7.80(s, 1H), 8.94(d, 1H, J=8.9 Hz), 9.51(s, 1H).

EIMS(m/z); 374(M)$^+$

Example 188

Compound 199

According to Example 2, 105 mg (47%) of a free base of Compound 199 was obtained from 187 mg (0.50 mmol) of Compound 198, 144 mg (1.00 mmol) of 2-dimethylaminoethyl chloride hydrochloride and 207 mg (1.50 mmol) of potassium carbonate.

According to Example 13, 102 mg (100%) of Compound 199 was obtained from 93 mg (0.21 mmol) of the free base of Compound 199.

$^1$HNMR(DMSO-d$_6$)∂; 2.50(s, 6H), 3.07(s, 3H), 3.14(t, 1H, J=5.0 Hz), 4.00(s, 3H), 4.16(t, 1H, J=5.0 Hz), 7.20–7.50 (m, 4H), 7.68(ddd, 1H, J=1.0, 6.9, 7.9 Hz), 7.76(d, 1H, J=8.4 Hz), 7.88(s, 1H), 8.96(d, 1H, J=7.9 Hz), 10.4(br, 1H).

EIMS(m/z); 445(M)$^+$

Example 189

Compound 200

To a suspension of 356 mg (1.00 mmol) of Compound 65 in 30 ml of chloroform were added 0.21 ml (2.00 mmol) of t-butylamine and 964 mg (2.00 mmol) of tetra-n-butylammonium tribromide under an ice-cooled condition, followed by stirring at the same temperature for 15 minutes. An aqueous saturated sodium sulfite solution was added to the reaction mixture, followed by extraction with CHCl$_3$. The extract was washed with brine, dried over Na$_2$SO$_4$, and evaporated. The residue was recrystallized from CHCl$_3$ to give 190 mg (37%) of Compound 200.

$^1$HNMR(DMSO-d$_6$)∂; 3.07(s, 3H), 3.98(s, 3H), 7.39(t, 1H, J=7.9 Hz), 7.46(d, 1H, J=2.5 Hz), 7.67(t, 1H, J=8.4 Hz), 7.74(d, 1H, J=8.4 Hz), 7.81(d, 1H, J=2.5 Hz), 7.86(s, 1H), 8.93(d, 1H, J=7.9 Hz), 9.33(br, 1H).

FABMS(m/z); 513(M+1)$^+$

Example 190

Compound 201

According to Example 45, 109 mg (61%) of a free base of Compound 201 was obtained from 158 mg (0.31 mmol) of Compound 200, 89 mg (0.62 mmol) of 2-dimethylaminoethyl chloride hydrochloride and 127 mg (0.92 mmol) of potassium carbonate.

According to Example 13, 95 mg (90%) of Compound 201 was obtained from 99 mg (0.17 mmol) of the free base of Compound 201.

$^1$HNMR(DMSO-d$_6$)∂; 2.48(s, 6H), 3.08(s, 3H), 3.10(m, 2H), 3.90(m, 2H), 4.01(s, 3H), 7.40(m, 1H), 7.65(m, 1H), 7.67(d, 1H, J=2.6 Hz), 7.78(d, 1H, J=8.6 Hz), 7.96(s, 1H), 8.04(d, 1H, J=2.3 Hz), 8.97(d, 1H, J=7.9 Hz), 9.95(br, 1H).

FABMS(m/z); 584(M+1)$^+$

Example 191

Compound 202

According to Example 45, 175 mg (62%) of Compound 202 was obtained from 240 mg (0.60 mmol) of Compound 166, 260 mg (1.80 mmol) of 2-dimethylaminoethyl chloride hydrochloride and 580 mg (4.20 mmol) of potassium carbonate.

$^1$HNMR(CDCl$_3$)∂; 1.91(s, 6H), 2.27(m, 2H), 3.22(s, 3H), 3.64(m, 1H), 3.81(m, 1H), 3.93(s, 3H), 7.31(t, 1H, J=8.0 Hz), 7.44(dt, 1H, J=1.0, 7.5 Hz), 7.51(d, 1H, J=8.3 Hz), 7.66(m, 2H), 7.67(s, 1H), 7.91(dd, 1H, J=1.7, 8.0 Hz), 9.13(m, 1H).

FABMS(m/z); 473(M+1)$^+$

Example 192

Compound 203

According to Example 5, 0.97 g (90%) of Compound 203 was obtained from 1.15 g (2.43 mmol) of Compound 202 and 0.30 g of 10% Pd/C.

$^1$HNMR(CDCl$_3$)∂; 2.11(s, 6H), 2.28(t, 2H, J=5.0 Hz), 3.20(s, 3H), 3.48(m, 2H), 3.91(s, 3H), 6.73(dd, 1H, J=1.6, 7.5 Hz), 6.83(dd, 1H, J=1.6, 7.9 Hz), 7.01(t, 1H, J=7.8 Hz), 7.40(ddd, 1H, J=0.9, 7.4, 7.9 Hz), 7.47(d, 1H, J=8.3 Hz), 7.62 s, 1H), 7.63(ddd, 1H, J=1.1, 7.4, 8.3 Hz), 9.12(dd, 1H, J=1.1, 7.9 Hz).

FABMS(m/z); 443(M+1)$^+$

Example 193

Compound 204

According to Example 6, 51 mg (47%) of Compound 204 was obtained from 100 mg (0.23 mmol) of Compound 203, 0.18 ml (2.30 mmol) of 35% formalin and 487 mg (2.30 mmol) of sodium triacetoxyborohydride.

$^1$HNMR(CDCl$_3$)∂; 1.94(s, 6H), 2.23(t, 2H, J=6.1 Hz), 2.89(s, 6H), 3.18(s, 3H), 3.81(t, 2H, J=6.1 Hz), 3.91(s, 3H), 6.95(dd, 1H, J=1.7, 7.3 Hz), 7.03(dd, 1H, J=1.7, 8.0 Hz), 7.13(t, 1H, J=7.7 Hz), 7.40(ddd, 1H, J=1.0, 7.2, 8.1 Hz), 7.46(d, 1H, J=8.2 Hz), 7.54(s, 1H), 7.63(ddd, 1H, J=1.1, 7.2, 8.2 Hz), 9.13(dd, 1H, J=1.1, 8.1 Hz).

FABMS(m/z); 471(M+1)$^+$

Example 194

Compound 205

According to Example 54, 93 mg (70%) of a free base of Compound 205 was obtained from 122 mg (0.28 mmol) of Compound 203, 0.115 ml (0.83 mmol) of triethylamine and 0.052 ml (0.55 mmol) of acetic anhydride.

According to Example 13, 86 mg (97%) of Compound 205 was obtained from 82 mg of the free base of Compound 205.

$^1$HNMR(DMSO-d$_6$)∂; 2.20(s, 3H), 2.55(s, 6H), 3.05(m, 2H), 3.06(s, 3H), 3.70(m, 2H), 4.00(s, 3H), 7.14(d, 1H, J=7.6 Hz), 7.22(d, 1H, J=7.6 Hz), 7.41(t, 1H, J=7.6 Hz), 7.68(t, 1H, J=8.2 Hz), 7.77(d, 1H, J=8.3 Hz), 7.87(s, 1H), 8.02(d, 1H, J=7.3 Hz), 8.97(d, 1H, J=7.9 Hz), 9.47(br, 1H).

EIMS(m/z); 484(M)$^+$

Example 195

Compound 206

To a solution of 138 mg (0.31 mmol) of Compound 203 in 10 ml of acetonitrile was added 0.029 ml (0.38 mmol) of methyl chloroformate, followed by stirring at room temperature for 30 minutes. Water was added to the reaction mixture, followed by extraction with AcOEt. The extract was washed with brine, dried over Na$_2$SO$_4$, and evaporated. The residue was purified by silica gel column chromatography (CHCl$_3$/MeOH=60/1) and recrystallized from methylene chloride-n-hexane to give 112 mg (72%) of a free base of Compound 206.

According to Example 13, 106 mg (99%) of Compound 206 was obtained from 100 mg (0.20 mmol) of the free base of Compound 206.

$^1$HNMR(DMSO-d$_6$)∂; 2.50(s, 6H), 3.05(m, 2H), 3.06(s, 3H), 3.75(m, 2H), 3.73(s, 3H), 4.00(s, 3H), 7.11(dd, 1H, J=1.7, 7.6 Hz), 7.23(t, 1H, J=7.6 Hz), 7.40(m, 1H), 7.65(m, 1H), 7.77(d, 1H, J=8.6 Hz), 7.86(s, 1H), 7.88(dd, 1H, J=1.7, 7.6 Hz), 8.97(d, 1H, J=7.9 Hz), 8.98(s, 1H), 9.89(br, 1H).

FABMS(m/z); 501(M+1)⁺

Example 196

Compound 207

According to Example 96, a 1,2,3,4-tetrahydro compound of Compound 207 was obtained from 2.45 g (6.90 mmol) of 2-[2-(3-benzyloxy-2-hydroxyphenyl)vinyl]-1-methylindole and 2.30 g (20.7 mmol) of N-methylmaleimide, followed by a treatment with 2.88 g (13.80 mmol) of DDQ to give 2.48 g (78%) of Compound 207.

¹HNMR(DMSO-$d_6$)∂; 3.06(s, 3H), 3.97(s, 3H), 5.23(s, 2H), 6.82(t, 1H, J=7.9 Hz), 6.90(dd, 1H, J=1.3, 7.9 Hz), 7.08(dd, 1H, J=1.3, 7.9 Hz), 7.30–7.60(m, 6H), 7.64(t, 1H, J=7.9 Hz), 7.73(d, 1H, J=7.9 Hz), 7.77(s, 1H), 8.56(s, 1H), 8.95(d, 1H, J=7.9 Hz).

FABMS(m/z); 463(M+1)⁺

Example 197

Compound 208

According to Example 45, 1.17 g (50%) of a free base of Compound 208 was obtained from 2.03 g (4.39 mmol) of Compound 207, 1.27 g (8.78 mmol) of 2-dimethylaminoethyl chloride hydrochloride and 1.82 g (13.2 mmol) of potassium carbonate.

According to Example 13, 98 mg (92%) of Compound 208 was obtained from 100 mg (0.19 mmol) of the free base of Compound 208.

¹HNMR(DMSO-$d_6$)∂; 2.41(s, 6H), 3.05(m, 2H), 3.06(s, 3H), 3.99(s, 3H), 4.05(m, 2H), 5.26(s, 2H), 7.00(dd, 1H, J=1.3, 7.6 Hz), 7.20(t, 1H, J=7.9 Hz), 7.30(dd, 1H, J=1.3, 8.2 Hz), 7.30–7.60(m, 6H), 7.67(t, 1H, J=7.9 Hz), 7.76(d, 1H, J=8.3 Hz), 7.82(s, 1H), 8.97(d, 1H, J=7.9 Hz), 9.85(br, 1H).

FABMS(m/z); 534(M+1)⁺

Example 198

Compound 209

According to Example 5, 0.82 g (78%) of a free base of Compound 209 was obtained from 1.27 g (2.38 mmol) of a free base of Compound 208 and 0.40 g of 10% Pd/C (50 wt %).

According to Example 13, 98 mg (91%) of Compound 209 was obtained from 100 mg (0.23 mmol) of the free base of Compound 209.

¹HNMR(DMSO-$d_6$)∂; 2.56(s, 6H), 3 05(m, 2H), 3.06(S, 3H), 3.95(m, 2H), 3.99(s, 3H), 6.81(t, 1H, J=4.6 Hz), 7.05(d, 1H, J=4.6 Hz), 7.39 (t, 1H, J=7.9 Hz), 7.66(t, 1H, J=7.9 Hz), 7.75(d, 1H, J=8.3 Hz), 7.80(s, 1H), 8.97(d, 1H, J=7.9 Hz), 9.82(br, 2H).

FABMS(m/z); 444(M+1)⁺

Example 199

Compound 210

According to Example 45, 56 mg (32%,) of a free base of Compound 210 was obtained from 150 mg (0.34 mmol) of a free base of Compound 209, 100 mg (0.68 mmol) of 2-dimethylaminoethyl chloride hydrochloride and 140 mg (1.02 mmol) of potassium carbonate.

According to Example 13, 57 mg (95%) of Compound 210 was obtained from 53 mg (0.10 mmol) of the free base of Compound 210.

¹HNMR(DMSO-$d_6$)∂; 2.53(s, 6H), 2.92(s, 6H), 3.05(m, 2H), 3.06(s, 3H), 3.75(m, 2H), 4.00(s, 3H), 4.10(m, 2H), 4.55(m, 2H), 7.04(dd, 1H, J=2.0, 7.0 Hz), 7.25(m, 2H), 7.41(t, 1H, J=7.3 Hz), 7.68(t, 1H, J=7.3 Hz), 7.77(d, 1H, J=8.6 Hz), 7.81(s, 1H), 8.97(d, 1H, J=7.3 Hz), 10.5(br, 1H), 10.6(br, 1H).

FABMS(m/z); 515(M+1)⁺

Example 200

Compound 211

According to Example 54, 101 mg (61%) of a free base of Compound 211 was obtained from 150 mg (0.34 mmol) of a free base of Compound 209, 0.24 ml (1.70 mmol) of triethylamine, 12 mg (0.06 mmol) of DMAP and 0.13 ml (1.36 mmol) of acetic anhydride.

According to Example 13, 85 mg (91%) of Compound 211 was obtained from 87 mg (0.18 mmol) of the free base of Compound 211.

¹HNMR(DMSO-$d_6$)∂; 2.41(s, 3H), 2.50(s, 6H), 3.05(m, 2H), 3.07(s, 3H), 3.87(t, 1H, J=5.0 Hz), 4.00(s, 3H), 7.25(m, 3H), 7.41(t, 1H, J=7.9 Hz), 7.68(t, 1H, J=7.9 Hz), 7.76(d, 1H, J=7.9 Hz), 7.87(s, 1H), 8.97(d, 1H, J=7.9 Hz), 10.0(br, 1H).

FABMS(m/z); 486(M+1)⁺

Example 201

Compound 212

To a solution of 100 mg (0.23 mmol) of a free base of Compound 209 in 2 ml of DMF was added 0.028 ml (0.45 mmol) of methyl iodide, followed by stirring at room temperature for 1.5 hours. After evaporation of the solvent under reduced pressure, the resulting residue was triturated with AcOEt to give 128 mg (97%) of Compound 212.

¹HNMR(DMSO-$d_6$)∂; 2.92(s, 9H), 3.05(s, 3H), 3.38(t, 1H, J=4.6 Hz), 3.99(s, 3H), 4.10(m, 2H), 6.84(dd, 1H, J=2.3, 6.9 Hz), 7.05(m, 2H), 7.40(t, 1H, J=7.6 Hz), 7.67(t, 1H, J=7.6 Hz), 7.76(d, 1H, J=8.3 Hz), 7.84(s, 1H), 8.97(d, 1H, J=7.9 Hz), 9.91(s, 1H).

FABMS(m/z); 459(M+1)⁺

Example 202

Compound 213

According to Example 96, a 1,2,3,4-tetrahydro compound of Compound 213 was obtained from 520 mg (1.86 mmol) of 2-[2-(2-hydroxy-3-methoxyphenyl)vinyl]-1-methylindole and 621 mg (5.59 mmol) of N-methylmaleimide, followed by a treatment with 837 mg (3.48 mmol) of DDQ to give 529 mg (74%) of Compound 213.

¹HNMR(DMSO-$d_6$)∂; 3.19(s, 3H), 3.90(s, 3H), 3.97(s, 3H), 5.85(s, 1H), 6.99(s, 3H), 7.39(ddd, 1H, J=1.0, 6.9, 7.9 Hz), 7.45(d, 1H, J=8.3 Hz), 7.54(s, 1H), 7.62(ddd, 1H, J=1.3, 7.3, 8.6 Hz), 9.10(d, 1H, J=7.9 Hz).

FABMS(m/z); 387(M+1)⁺

Example 203

Compound 214

According to Example 45, 64 mg (36%) of a free base of Compound 214 was obtained from 150 mg (0.39 mmol)of Compound 213, 84 mg (0.58 mmol) of 2-dimethylaminoethyl chloride hydrochloride and 135 mg (0.98 mmol) of potassium carbonate.

According to Example 13, 59 mg (98%) of Compound 214 was obtained from 56 mg (0.12 mmol) of the free base of Compound 214.

¹HNMR(DMSO-$d_6$)∂; 2.57(s, 6H), 3.05(m, 2H), 3.06(s, 3H), 3.90(m, 2H), 3.93(s, 3H), 3.99(s, 3H), 6.97(t, 1H, J=4.9

Hz), 7.22(d, 1H, J=4.9 Hz), 7.40(t, 1H, J=6.9 Hz,), 7.67(t, 1H, J=6.9 Hz), 7.76(d, 1H, J=8.4 Hz), 7.81(s, 1H), 8.97(d, 1H, J=7.9 Hz), 9.89(br, 1H).

FABMS(m/z); 458(M+1)$^+$

Example 204

Compound 215

To a solution of 1.50 g (6.02 mmol) of 2-[2-(2-hydroxyphenyl)vinyl]-1-methylindole, 1.89 g (7.21 mmol) of triphenylphosphine and 0.69 ml (7.22 mmol) of R-(+)-methyl lactate in 15 ml of THF was added 1.14 ml (7.24 mmol) of diethylazodicarboxylate under an ice-cooled condition, followed by stirring at room temperature for 2 hours. Brine was added to the reaction mixture, followed by extraction with methylene chloride. The extract was dried over $Na_2SO_4$, and evaporated. $CHCl_3$-n-hexane was added to the residue and, after filtration, the organic layer was purified by silica gel column chromatography ($CHCl_3$/n-hexane/AcOEt=10/10/1) to give 1.82 g (90%) of (S)-2-{2 [2-(1-methoxycarbonylethoxy)phenyl]vinyl}-1-methylindole.

$^1$HNMR(CDCl$_3$)∂; 1.69(d, 3H, J=6.8 Hz), 3.77(s, 3H), 3.83(s, 3H), 4.84(q, 1H, J=6.8 Hz), 6.78(dd, 1H, J=0.7, 8.3 Hz), 6.82(m, 1H), 7.01(dt, 1H, J=0.7, 7.6 Hz), 7.09(ddd, 1H, J=1.2, 7.1, 8.1 Hz), 7.18(m, 2H), 7.29(dd, 1H, J=1.0, 7.6 Hz), 7.29(d, 1H, J=16.4 Hz), 7.54(d, 1H, J=16.4 Hz), 7.59(m, 2H).

FABMS(m/z); 336(M+1)$^+$

To a solution of 1.78 g (5.31 mmol) of (S)-2-{2[2-(1-methoxycarbonylethoxy)phenyl]vinyl}-1-methylindole in 100 ml of THF was added 12 ml of a 0.98M n-hexane solution of diisobutylalminum hydride (11.76 mmol), followed by stirring at 0° C. for 30 minutes. Ice water and 2N hydrochloric acid were added to the reaction mixture, followed by extraction with methylene chloride. The extract was washed with 2N hydrochloric acid and then with brine, dried over $Na_2SO_4$, and evaporated. The residue was purified by silica gel column chromatography ($CHCl_3$/MeOH= 100/1) to give 1.52 g (93%) of (S)-2-{2-[2-(2-hydroxyisopropoxy)phenyl]vinyl}-1-methylindole.

$^1$HNMR(CDCl$_3$)∂; 1.34(d, 3H, J=6.4 Hz), 3.16-3.72(m, 2H), 3.82(s, 3H), 4.58(m, 1H), 7.00(m, 2H), 7.09(m, 2H), 7.17-7.32(m, 4H), 7.49(d, 1H, J=6.4 Hz), 7.58(m, 2H).

FABMS(m/z); 308(M+1)$^+$

According to Example 96, a 1,2,3,4-tetrahydro compound of Compound 215 was obtained from 1.50 g (4.87 mmol) of (S)-2-{2-[2-(2-hydroxyisopropoxy)phenyl]vinyl}-1-methylindole and 1.08 g (9.72 mmol) of N-methylmaleimide, followed by a treatment with 2.20 g (9.69 mmol) of DDQ to give 0.57 g (28%) of Compound 215.

$^1$HNMR(CDCl$_3$)∂; 1.12(d, 3H, J=6.3 Hz), 3.19(s, 3H), 3.42(m, 1H), 3.68(m, 1H), 3.91(s, 3H), 4.60(m, 1H), 7.08(d, 1H, J=8.1 Hz), 7.08(t, 1H, J=7.6 Hz), 7.36(dd, 1H, J=1.7, 7.6 Hz), 7.41(m, 2H), 7.46(s, 1H), 7.46(d, 1H, J=8.3 Hz), 7.63(ddd, 1H, J=1.5, 7.3, 8.3 Hz), 9.11(d, 1H, J=7.2 Hz).

FABMS(m/z); 415(M+1)$^+$

Example 205

Compound 216 and Compound 217

To a solution of 0.40 g (0.97 mmol) of Compound 215 in 10 ml of 1,2-dichloroethane were added 0.64 ml (7.91 mmol) of pyridine and 1.12 g (5.87 mmol) of p-toluenesulfonyl chloride, followed by stirring at 60° C. for 39 hours. An aqueous saturated sodium hydrogencarbonate solution was added to the reaction mixture, followed by extraction with $CHCl_3$. The extract was washed with the aqueous saturated sodium hydrogencarbonate solution and then brine, dried over $Na_2SO_4$, and evaporated. The residue was purified by silica gel column chromatography ($CHCl_3$) to give 418 mg (76%) of Compound 216 and 103 mg (19%) of Compound 217.

Compound 216

$^1$HNMR(CDCl$_3$)∂; 1.16(d, 3H, J=6.4 Hz), 2.30(s, 3H), 3.15(s, 3H), 3.90(s, 3H), 3.90(m, 2H), 4.50(q, 1H, J=6.4 Hz), 6.85-7.76(m, 12H), 9.12(d, 1H, J=7.8 Hz).

FABMS(m/z); 569(M+1)$^+$

Compound 217

$^1$HNMR(CDCl$_3$)∂; 1.27(d, 3H, J=6.2 Hz), 3.21(s, 3H), 3.43(m, 1H), 3.54(dd, 1H, J=4.8, 11.2 Hz), 3.93(s, 3H), 4.53(m, 1H), 7.05(dd, 1H, J=1.0, 7.9 Hz), 7.14(dt, 1H, J=1.1, 7.5 Hz), 7.43(m, 3H), 7.48(d, 1H, J=8.3 Hz), 7.58(br s, 1H), 7.64(ddd, 1H, J=1.1, 7.1, 8.3 Hz), 9.14(dt, 1H, J=1.0, 7.9 Hz).

FABMS(m/z); 433(M+1)$^+$

Example 206

Compound 218

According to Example 20, 220 mg (71%) of a free base of Compound 218 was obtained from 440 mg (0.77 mmol) of Compound 216 and 7.0 ml (77.61 mmol) of 50% aqueous dimethylamine solution.

According to Example 13, 220 mg (95%) of Compound 218 was obtained from 215 mg (0.49 mmol) of the free base of Compound 218.

$^1$HNMR(DMSO-d$_6$)∂; 1.10(d, 3H, J=4.5 Hz), 2.59(br s, 6H), 3.05(s, 3H), 3.05(m, 1H), 3.19(m, 1H), 3.98(s, 3H), 4.93(m, 1H), 7.12(t, 1H, J=7.5 Hz), 7.27(m, 1H), 7.40(m, 2H), 7.47(ddd, 1H, J=1.2, 7.2, 7.9 Hz), 7.67(ddd, 1H, J=1.1, 7.2, 8.3 Hz), 7.75(d, 1H, J=8.3 Hz), 7.81(s, 1H), 8.96(ddd, 1H, J=0.6, 1.1, 7.9 Hz), 9.96(br s, 1H).

FABMS(m/z); 442(M+1)$^+$

Example 207

Compound 219

According to Example 204, 1.85 g (92%) of (R)-2-{2-[2-(1-methoxycarbonylethoxy)phenyl]vinyl}-1-methylindole was obtained from 1.50 g (6.02 mmol of 2-[2-(2-hydroxyphenyl)vinyl]-1-methylindole, 1.89 g (7.21 mmol) of triphenylphosphine, 0.69 ml (7.22 mmol) of S-(−)-methyl lactate and 1.14 ml (7.24 mmol) of diethylazodicarboxylate.

$^1$HNMR(CDCl$_3$)∂; 1.70(d, 3H, J=6.8 Hz), 3.78(s, 3H), 3.83(s, 3H), 4.84(q, 1H, J=6.8 Hz), 6.79(dd, 1H, J=0.7, 7.9 Hz), 6.83(m, 1H), 7.02(m, 1H), 7.09(ddd, 1H, J=0.9, 7.1, 7.9 Hz), 7.19(m, 2H), 7.29(dd, 1H, J=0.8, 7.9 Hz), 7.30(d, 1H, J=16.3 Hz), 7.54(d, 1H, J=16.3 Hz), 7.59(m, 2H).

FABMS(m/z); 336(M+1)$^+$

Then, 1.64 g 98%) of (R)-2-{2-[2-(2-hydroxyisopropoxy)phenyl]vinyl}-1-methylindole was obtained from 1.83 g (5.46 mmol) of (R)-2-{2-[2-(1-methoxycarbonylethoxy)phenyl]vinyl}-1-methylindole and 12.34 ml (12.09 mmol) of a 0.98M n-hexane solution of diisobutylalminum hydride.

FABMS(m/z); 308(M+1)$^+$

According to Example 96, a 1,2,3,4-tetrahydro compound of Compound 219 was obtained from 1.62 g (5.27 mmol) of (R)-2-{2-[2-(2-hydroxyisopropoxy)phenyl]vinyl}-1-methylindole and 1.17 g (10.54 mmol) of N-methylmaleimide, followed by a treatment with 2.03 g (8.96 mmol) of DDQ to give 0.66 g (33%) of Compound 219.

¹HNMR(CDCl₃)∂; 1.12(d, 3H, J=6.2 Hz), 3.20(s, 3H), 3.42(m, 1H), 3.71(m, 1H), 3.92(s, 3H), 4.61(m, 1H), 7.08(d, 1H, J=8.3 Hz), 7.08(m, 1H), 7.36(dd, 1H, J=1.8, 7.7 Hz), 7.42(m, 2H), 7.47(s, 1H), 7.47(d, 1H, J=7.4 Hz), 7.63(ddd, 1H, J=1.1, 7.4, 8.4 Hz), 9.12(dd, 1H, J=1.1, 8.0 Hz).

FABMS(m/z); 415(M+1)⁺

Example 208

Compound 220, Compound 221 and Compound 222

According to Example 205, Compound 220 and Compound 221 were obtained from 0.45 g (1.08 mmol) of Compound 219, 0.70 ml (8.66 mmol) of pyridine and 1.23 g (6.45 mmol) of p-toluenesulfonyl chloride.
Compound 220

FABMS(m/z); 569(M+1)⁺
Compound 221

FABMS(m/z); 433(M+1)⁺

Then, according to Example 20, 0.31 g (64%) of a free base of Compound 222 was obtained by treating 0.61 g (1.07 mmol) of Compound 220 with 10.0 ml (110.87 mmol) of 50% aqueous dimethylamine solution.

According to Example 13, 307 mg (94%) of Compound 222 was obtained from 301 mg (0.69 mmol) of the free base of Compound 222.

¹HNMR(DMSO-d₆)∂; 1.11(d, 3H, J=4.9 Hz), 2.59(br s, 6H), 3.06(s, 3H), 3.06(m, 1H), 3.18(m, 1H), 3.98(s, 3H), 4.92(m, 1H), 7.12(t, 1H, J=7.4 Hz), 7.27(m, 1H), 7.40(m, 2H), 7.47(dt, 1H, J=1.7, 7.5 Hz), 7.67(ddd, 1H, J=1.1, 7.2, 8.3 Hz), 7.75(d, 1H, J=8.3 Hz), 7.81(s, 1H), 8.96(d, 1H, J=7.9 Hz), 9.74(br, 1H).

FABMS(m/z); 442(M+1)⁺

Example 209

Compound 223

According to Example 54, 137 mg (92%) of a free base of Compound 223 was obtained from 121 mg (0.27 mmol) of Compound 148, 0.10 ml (0.12 mmol) of triethylamine and 0.04 ml (0.34 mmol) of benzoyl chloride.

According to Example 13, 117 mg (85%) of Compound 223 was obtained from 130 mg (0.24 mmol) of the free base of Compound 223.

¹HNMR(DMSO-d₆)∂; 2.55(s, 6H), 3.08(s, 3H), 3.25(m, 2H), 3.99(s, 3H), 4.35(m, 2H), 7.28(d, 1H, J=8.0 Hz), 7.30–7.40(m, 3H), 7.60–7.80(m, 5H), 7.89(s, 1H), 8.15(d, 2H, J=8.0 Hz), 8.96(d, 1H, J=8.0 Hz).

FABMS(m/z); 548(M+1)⁺

Example 210

Compound 224 and Compound 225

According to Example 45, 10 mg (15%) of Compound 224 and 26 mg (41%) of Compound 225 were obtained from 50 mg (0.13 mmol) of Compound 179, 82 mg (0.52 mmol) of 2-dimethylaminoisopropyl chloride hydrochloride and 144 mg (1.04 mmol) of potassium carbonate.
Compound 224

¹HNMR(CDCl₃)∂; 1.18(d, 3H, J=6.1 Hz), 2.12(br s, 6H), 2.22(m, 1H), 2.38(m, 1H), 2.84(s, 3H), 3.21(s, 3H), 3.95(s, 3H), 4.46(m, 1H), 7.08(m, 2H), 7.36(dd, 1H, J=1.7, 7.8 Hz), 7.42(ddd, 1H, J=1.7, 7.6, 8.0 Hz), 7.51(d, 1H, J=8.6 Hz), 7.59(s, 1H), 8.34(dd, 1H, J=1.9, 8.6 Hz), 9.77(d, 1H, J=1.9 Hz).

FABMS(m/z); 484(M+1)⁺
Compound 225

¹HNMR(CDCl₃)∂; 0.88(d, 3H, J=5.9 Hz), 2.16(br s, 6H), 2.72(m, 1H), 2.84(s, 3H), 3.20(s, 3H), 3.87(m, 1H), 3.95(s, 3H), 4.08(dd, 1H, J=5.0, 8.9 Hz), 7.03(d, 1H, J=8.3 Hz), 7.10(dt, 1H, J=1.0, 7.5 Hz), 7.37(dd, 1H, J=1.7, 7.5 Hz), 7.45(ddd, 1H, J=1.7, 7.5, 8.3 Hz), 7.51(d, 1H, J=8.8 Hz), 7.56(s, 1H), 8.35(dd, 1H, J=1.8, 8.8 Hz), 9.77(dd, 1H, J=0.5, 1.8 Hz).

FABMS(m/z); 484(M+1)⁺

Example 211

Compound 226

To a solution of 4.25 g (9.91 mmol) of Compound 110 in 45 ml of THF was added 14 ml (14.98 mmol) of a 1.07M THF solution of borane-THF complex at 0° C., followed by stirring at room temperature for 30 minutes. Further, 14 ml (14.98 mmol) of the 1.07M THF solution of borane-THF complex was added thereto, followed by stirring at the same temperature for 45 minutes. Ice water was added to the reaction mixture, followed by extraction with CHCl₃. The extract was washed with an aqueous saturated sodium hydrogencarbonate solution and then brine, dried over Na₂SO₄, and evaporated. The residue was triturated with AcOEt to give 3.50 g (85%) of Compound 226.

FABMS(m/z); 415(M+1)⁺

Example 212

Compound 227 and Compound 228

According to Example 205, 0.61 g (99%) of Compound 227 was obtained from 0.45 g (1.08 mmol) of Compound 226, 0.70 ml (8.66 mmol) of pyridine and 1.23 g (6.45 mmol) of p-toluenesulfonyl chloride.

FABMS(m/z); 569(M+1)⁺

According to Example 20, 0.31 g (61%) of a free base of Compound 228 was obtained by treating 0.61 g of Compound 227 with 5.6 ml (54.13 mmol) of diethylamine.

According to Example 13, 293 mg (91%) of Compound 228 was obtained from 300 mg (0.64 mmol) of the free base of Compound 228.

¹HNMR(DMSO-d₆)∂; 0.43–1.20(m, 9H), 2.60–2.98(m, 4H), 3.02(m, 1H), 3.06(s, 3H), 3.15(m, 1H), 3.98(s, 3H), 4.93(m, 1H), 7.12(t, 1H, J=7.4 Hz), 7.19(m, 1H), 7.40(m, 2H), 7.47(m, 1H), 7.67(m, 1H), 7.76(d, 1H, J=8.3 Hz), 7.78(s, 1H), 8.95(d, 1H, J=7.9 Hz), 9.49(br, 1H).

FABMS(m/z); 470(M+1)⁺

Example 213

Compound 229

According to Example 54, 2.20 g (92%) of 2-[2-(2-acetoxyphenyl)vinyl]-7-dibutoxymethyl-1-methylindole was obtained from 2.08 g (5.29 mmol) of 7-dibutoxymethyl-2-[2-(2-hydroxyphenyl)vinyl]-1-methylindote, 0.29 g (2.35 mmol) of DMAP, 5.00 ml (61.82 mmol) of pyridine and 0.53 ml (5.62 mmol) of acetic anhydride.

¹HNMR(DMSO-d₆)∂; 0.85(t, 6H, J=7.3 Hz), 1.29–1.57 (m, 8H), 2.39(s, 3H), 3.40–3.64(m, 4H), 4.08(s, 3H), 5.89(s, 1H), 6.95(s, 1H), 6.97–7.53(m, 7H), 7.98(dd, 1H, J=2.1, 7.4 Hz).

FABMS(m/z); 449(M+1)⁺

According to Example 96, 1.33 g (52%) of N-methyl-2-(2-acetoxyphenyl)-8-dibutoxymethyl-9-methyl-1,2,3,4-tetrahydrocarbazole-3,4-dicarboxyimide was obtained from 2.07 g (4.60 mmol) of 2-[2-(2-acetoxyphenyl)vinyl]-7-dibutoxymethyl-1-methylindole and 2.16 g (19.40 mmol) of N-methylmaleimide.

FABMS(m/z); 560(M)⁺

Then, 228 mg (0.41 mmol) of N-methyl-2-(2-acetoxyphenyl)-8-dibutoxymethyl-9-methyl-1,2,3,4,-tetrahydrocarbazole-3,4-dicarboxyimide and 197 mg (0.87 mmol) of DDQ were added to 10 ml of ethylene chloride, followed by stirring at room temperature for 2 hours. After removing the resulting precipitate by filtration, the filtrate was washed with an aqueous saturated sodium hydrogencarbonate solution, dried over MgSO$_4$ and evaporated. The residue was triturated with MeOH to give 48 mg (27%) of Compound 229.

$^1$HNMR(CDCl$_3$)∂; 1.91(s, 3H), 3.21(s, 3H), 4.22(s, 3H), 7.26(dd, 1H, J=1.2, 8.1 Hz), 7.40(dt, 1H, J=1.2, 7.6 Hz), 7.46(dd, 1H, J=1.8, 7.6 Hz), 7.53(ddd, 1H, J=1.8, 7.6, 8.1 Hz), 7.54(t, 1H, J=7.7 Hz), 7.58(s, 1H), 8.08(dd, 1H, J=1.2, 7.7 Hz), 9.51(dd, 1H, J=1.2, 7.7 Hz), 10.36(s, 1H).

FABMS(m/z); 427(M+1)$^+$

Example 214

Compound 230 and Compound 231

According to Example 118, Compound 230 was obtained from 151 mg (0.35 mmol) of Compound 229 and 44 mg (0.32 mmol) of potassium carbonate.

FABMS(m/z); 385(M+1)$^+$

Then, according to Example 45, 156 mg (96% yield from Compound 229) of a free base of Compound 231 was obtained by treating the above-mentioned Compound 230 with 66 mg (0.46 mmol) of 2-dimethylaminoethyl chloride hydrochloride and 185 mg (1.34 mmol) of potassium carbonate.

According to Example 13, 26 mg (87%) of Compound 231 was obtained from 27 mg (0.06 mmol) of the free base of Compound 231.

$^1$HNMR(DMSO-d$_6$)∂; 2.57(s, 6H), 3.07(s, 3H), 3.29(br s, 2H), 4.25(s, 3H), 4.32(br s, 2H), 7.14(t, 1H, J=7.3 Hz), 7.21(d, 1H, J=7.8 Hz), 7.41(dd, 1H, J=1.7, 7.3 Hz), 7.49 (ddd, 1H, J=1.7, 7.3, 7.8 Hz), 7.58(t, 1H, J=7.7 Hz), 7.99(s, 1H), 8.21(dd, 1H, J=1.4, 7.7 Hz), 9.37(dd, 1H, J=1.4, 7.7 Hz), 10.62(s, 1H).

FABMS(m/z); 456(M+1)$^+$

INDUSTRIAL APPLICABILITY

Novel pyrrolocarbazole derivatives and pharmaceutically acceptable salts thereof useful as a therapeutic agent for thrombocytopenia are provided according to the present invention.

We claim:

1. A pyrrolocarbazole derivative having the following formula:

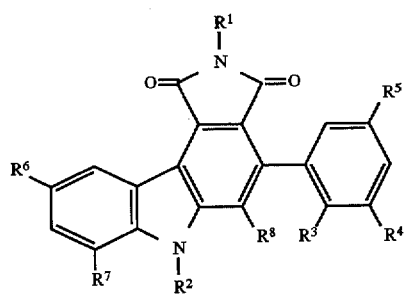

[(I)]

wherein

R$^1$ is lower alkyl or aralykyl;

R$^2$ is hydrogen, substituted or unsubstituted lower alkyl, lower alkenyl, or substituted or unsubstituted aralkyl;

R$^3$, R$^4$, R$^5$, R$^6$ and R$^7$ are independently hydrogen, halogen, nitro, substituted or unsubstituted lower alkanoyl, NR$^9$R$^{10}$ (wherein R$^9$ and R$^{10}$ are independently hydrogen, substituted or unsubstituted lower alkyl, substituted or unsubstituted lower alkanoyl, aroyl, lower alkoxycarbonyl, aralkyloxycarbonyl, or an amino acid residue in which a hydroxyl group in a carboxylic acid is removed and an amino group of the amino acid is optionally protected by a protective group, or OR$^{11}$ (wherein R$^{11}$ is hydrogen, substituted or unsubstituted lower alkyl, substituted or unsubstituted lower alkanoyl, aroyl, substituted or unsubstituted aralkyl, or heteroaralkyl);

R$^8$ is hydrogen or is combined with R$^3$ to form —CONR$^{12}$— (wherein R$^{12}$ is hydrogen, or substituted or unsubstituted lower alkyl), with the proviso that when R$^1$ is benzyl, R$^2$, R$^3$, R$^4$, R$^5$, R$^6$, R$^7$ and R$^8$ are not simultaneously hydrogen;

and with the proviso that R$^1$ is not benzyl when two of R$^3$, R$^4$ and R$^5$ are chloro and the remainder is hydrogen or a pharmaceutically acceptable salt thereof.

2. A compound according to claim 1, wherein R$^1$ is lower alkyl.

3. A compound according to claim 2, wherein R$^1$ is methyl.

4. A compound according to claim 1, wherein R$^1$ is benzyl.

5. A compound according to claim 1, wherein R$^2$ is lower alkyl.

6. A compound according to claim 5, wherein R$^2$ is methyl.

7. A compound according to claim 1, in which R$^3$ is NR$^9$R$^{10}$ wherein R$^9$ and R$^{10}$ are independently hydrogen, substituted or unsubstituted lower alkyl, substituted or unsubstituted lower alkanoyl, aroyl, lower alkoxycarbonyl, aralkyloxycarbonyl or said amino acid residue having an amino group which is optionally protected by a protective group.

8. A compound according to claim 1, in which R$^3$ is OR$^{11}$ wherein R$^{11}$ is hydrogen, substituted or unsubstituted lower alkyl, substituted or unsubstituted lower alkanoyl, aroyl, substituted or unsubstituted aralkyl, or heteroaralkyl.

9. A compound according to claim 1, in which R$^8$ is combined with R$^3$ to form —CONR$^{12}$— wherein R$^{12}$ is hydrogen, or substituted or unsubstituted lower alkyl.

10. A compound according to claim 7, wherein R$^1$ and R$^2$ are methyl.

11. A compound according to claim 8, wherein R$^1$ and R$^2$ are methyl.

12. A medical composition comprising at least one of the compounds according to claim 1 and a pharmaceutically acceptable carrier thereof.

13. A method of treating thrombocytopenia which comprises administering an effective amount of a compound according to claim 1 to a patient in need thereof.

* * * * *

UNITED STATES PATENT AND TRADEMARK OFFICE
CERTIFICATE OF CORRECTION

PATENT NO. : 5,728,709

DATED : March 17, 1998

INVENTOR(S): YOJI IKUINA ET AL.

It is certified that error appears in the above-identified patent and that said Letters Patent is hereby corrected as shown below:

COLUMN 1

Line 26, "unknown" should read --unknown whether--;
Line 54, "amine" should read --amino--;
Line 56, "amine" should read --amino--.

COLUMN 2

Line 9, "the" should read --the same--;
Line 28, "M-containing" should read --N-containing--.

COLUMN 7

Line 63, "amine" should read --amino--;
Line 67, "etoxyborohidrido." should read --etoxyborohidride.--

COLUMN 10

Line 51, "none--" should read --mono---.

COLUMN 12

Line 27, "amine" should read --amino--;
Line 32, "amine" should read --amino--.

UNITED STATES PATENT AND TRADEMARK OFFICE
CERTIFICATE OF CORRECTION

PATENT NO. : 5,728,709

DATED : March 17, 1998

INVENTOR(S): YOJI IKUINA ET AL.

It is certified that error appears in the above-identified patent and that said Letters Patent is hereby corrected as shown below:

COLUMN 14

Line 39, "(XIII" should read --(XIII)--.

COLUMN 32

Line 61, "redfaced" should read --reduced--.

COLUMN 34

Line 2, "(m, 7H" should read (m, 7H),--;
Line 63 "(S, 2H," should read (S, 2H),--.

COLUMN 35

Line 15, "8,3" should read --8.3--;
Line 22, "to" should be deleted;
Line 45, "8,3" should read --8.3--;
Line 51, "was dissolved" should be deleted.

COLUMN 37

Line 34, "Hz," should read --Hz),--;
Line 44, "(274)" should read --(27%)--;
Line 52, "1H," should --1H),--
Line 59, "0.31" should read --(0.31--.
Column 35, line 22, "10" should read --110--.

UNITED STATES PATENT AND TRADEMARK OFFICE
CERTIFICATE OF CORRECTION

PATENT NO. : 5,728,709

DATED : March 17, 1998

INVENTOR(S): YOJI IKUINA ET AL.

It is certified that error appears in the above-identified patent and that said Letters Patent is hereby corrected as shown below:

COLUMN 42

Line 13, "( s 1H)," should read --(S, 1H),--.

COLUMN 43

Line 62, "7.4 Hz" should read --7.4 Hz), 7.13--

COLUMN 44

Line 45, "dr," should read --dt,--.

COLUMN 45

Line 8, "no" should read --to--.

COLUMN 52

Line 40, "mmol" should read --mmol)--.

COLUMN 55

Line 4, "trimethylsilylethoxymethyl" should read --trimethylsilylethoxymethylindole--;
Line 31, "no" should read --to--;
Line 35, "472(M+1)$^{30}$" should read --(472(M+1)$^{+}$--.

UNITED STATES PATENT AND TRADEMARK OFFICE
CERTIFICATE OF CORRECTION

PATENT NO. : 5,728,709

DATED : March 17, 1998

INVENTOR(S): YOJI IKUINA ET AL.

It is certified that error appears in the above-identified patent and that said Letters Patent is hereby corrected as shown below:

COLUMN 64

Line 65, "(18k)" should read --(18%)--.

COLUMN 65

Line 13, "a.02(dd," should read --4.02(dd,--;
Line 27, "3.! 9" should read --3.19--.

COLUMN 66

Line 7, "no" should read --to--.
Line 32, "3.i9(s," should read --3.19(s,--;
Line 35, "dd," should read --(dd,--;
Line 46, "dd," should read --(dd,--.

COLUMN 68

Line 5, "d," should --(d,--.

COLUMN 69

Line 10, "mmol" should read --mmol)--.

COLUMN 76

Line 4, "33?" should read --337--.

UNITED STATES PATENT AND TRADEMARK OFFICE
CERTIFICATE OF CORRECTION

PATENT NO. : 5,728,709

DATED : March 17, 1998

INVENTOR(S): YOJI IKUINA ET AL.

It is certified that error appears in the above-identified patent and that said Letters Patent is hereby corrected as shown below:

COLUMN 77

Line 48, "7.13(:," should read --7.13(t,--;
Line 56, "no" should read --to--.

COLUMN 78

Line 16, "m," should read --(m,--.

COLUMN 80

Line 6, "4.3t" should read --4.31--.

COLUMN 83

Line 44, "mmol" should read --mmol)--.

COLUMN 86

Line 54, "98%) should read --(98%)--.

COLUMN 88

Line 52, "--1--methylindote, should read ----1--methylindole,--.

UNITED STATES PATENT AND TRADEMARK OFFICE
CERTIFICATE OF CORRECTION

PATENT NO. : 5,728,709

DATED : March 17, 1998

INVENTOR(S): YOJI IKUINA ET AL.

It is certified that error appears in the above-identified patent and that said Letters Patent is hereby corrected as shown below:

<u>COLUMN 89</u>

Line 53, "[(I)]" should be deleted.

<u>COLUMN 90</u>

Line 14, "group," should read --group),--;
Line 25, "hydrogen" should read --hydrogen;--.

Signed and Sealed this

Fifth Day of January, 1999

Attest:

*Attesting Officer*

*Acting Commissioner of Patents and Trademarks*